US009056904B2

(12) United States Patent
Clarke et al.

(10) Patent No.: US 9,056,904 B2
(45) Date of Patent: Jun. 16, 2015

(54) PEPTIDE ANALOGUES OF PA-IL AND THEIR UTILITY FOR GLYCAN AND GLYCOCONJUGATE ANALYSIS AND PURIFICATION

(71) Applicant: Dublin City University, Dublin (IE)

(72) Inventors: Paul Clarke, Dublin (IE); Roisin Thompson, Dublin (IE); Brendan O'Connor, Dublin (IE); Michael O'Connell, Dublin (IE); Kenneth McMahon, County Meath (IE)

(73) Assignee: Dublin City University, Dublin (IE)

( * ) Notice: Subject to any disclaimer, the term of this patent is extended or adjusted under 35 U.S.C. 154(b) by 0 days.

(21) Appl. No.: 13/933,195

(22) Filed: Jul. 2, 2013

(65) Prior Publication Data

US 2014/0106371 A1 Apr. 17, 2014

(30) Foreign Application Priority Data

Oct. 16, 2012 (EP) .................................... 12188702

(51) Int. Cl.
*C07K 14/00* (2006.01)
*C07K 14/195* (2006.01)
*C07K 14/21* (2006.01)
*C07K 14/435* (2006.01)

(52) U.S. Cl.
CPC ............... *C07K 14/21* (2013.01); *C07K 14/435* (2013.01)

(58) Field of Classification Search
CPC ............................ C07K 14/21; C07K 14/435
See application file for complete search history.

(56) References Cited

PUBLICATIONS

Qiagen, N-Terminus pQE Vector Set, Sample & Assay Technologies, Product Information, pp. 1-4, also available at http://www.qiagen.com/products/catalog/sample-technologies/protein-sample-technologies/expression-kits-and-vectors/n-terminus-pqe-vector-set?productdetails=1&print=1#productdetails, last visited May 22, 2014.*

Dublin City University Academic Regulations for Postgraduate Degrees by Research and Thesis, Dublin City Univeristy, Archives Dec. 2007 to Sep. 2011, 1-29.*

Capitadiscovery.co.uk/DCU, attached as pdf, also available at http://capitadiscovery.co.uk/dcu/items?query=Structural+and+Functional+Characterisation+of+lectins (last visited Nov. 19, 2014).*

(Continued)

*Primary Examiner* — Christina Bradley
*Assistant Examiner* — Randall L Beane
(74) *Attorney, Agent, or Firm* — Hodgson Russ LLP

(57) ABSTRACT

Provided are peptide analogs of PA-IL and compositions containing them. The PA-IL peptide analogs have altered carbohydrate binding specificity relative to a PA-IL of SEQ ID NO:1, and thus the analogs contain amino acid substitutions in SEQ ID NO:1. The substitutions can be at positions 50, 52 and 53 of SEQ ID NO:1 and can include combinations of amino acid substitutions at those positions. Also included are methods for detecting changes in the glycosylation of carbohydrates and for separating biomolecules which contain glycoproteins or glycoconjugates.

3 Claims, 24 Drawing Sheets

Identification of Amino Acid Substitutions Present in Isolated rPA-ILNm Proteins.

| | | 45 | 50 | | 52 | 53 | | 58 |
|---|---|---|---|---|---|---|---|---|
| **rPA-ILN** | : | QGDRE- | H | P | D | Q | -GLIC | H |
| **rPA-ILNmE12** | : | QGDRE- | G | P | C | R | -GLIC | H |
| **rPA-ILNmF3** | : | QGDRE- | V | P | C | R | -GLIC | H |
| **rPA-ILNmB10** | : | QGDRE- | V | P | C | E | -GLIC | H |
| **rPA-ILNmG3** | : | QGDRE- | V | P | N | N | -GLIC | H |
| **rPA-ILNmB4** | : | QGDRE- | T | P | N | R | -GLIC | H |
| **rPA-ILNmE6** | : | QGDRE- | N | P | N | G | -GLIC | H |
| **rPA-ILNmC5** | : | QGDRE- | N | P | T | S | -GLIC | H |
| **rPA-ILNmA8** | : | QGDRE- | L | P | H | R | -GLIC | H |
| **rPA-ILNmF6** | : | QGDRE- | P | P | R | L | -GLIC | H |

(56) References Cited

PUBLICATIONS

R. Hill, DORAS-Increasing the Visibility and Impact of DCU Research, International Symposium for Engineering Education, ISEE-08, Dublin City University (2008), 207-212, also available at http://doras.dcu.ie/2189/1/hill_rachel_isee08.pdf (last visited Nov. 19, 2014).*

Thompson, R., et al., ProLegere, Recombinant Prokaryotic Lectins: Enhanced Tools for Glycoprotein Analysis & Purification, Glycoscience Ireland Poster, Oct. 2012, 1 page.

McMahon, K., Structural and Functional Characterisation of Lectins from the PA-IL Superfamily, Sep. 2009, Ph.D. Thesis, pp. 1-260.

Dwek, R. A., Glycobiology: Toward Understanding the Function of Sugars, Chemical Reviews, 1996, vol. 96, No. 2, pp. 683-720.

Hearty, S., et al., Production, characterisation and potential application of a novel monoclonal antibody for rapid identification of virulent *Listeria monocytogenes*, Journal of Microbiological Methods, Feb. 2, 2006, vol. 66, pp. 294-312.

Katrlik, J., et al., Glycan and lectin microarrays for glycomics and medicinal applications, Medicinal Research Reviews, Jan. 22, 2010, vol. 30, pp. 394-418.

Mislovičová, D., et al., Lectinomics I. Relevance of exogenous plant lectins in biomedical diagnostics, Biologia. 2009, vol. 64, No. 1, pp. 1-19.

Gemeiner, P., et al., Lectinomics: II. A highway to biomedical/clinical diagnostics, Biotechnology Advances, Jul. 23, 2008, vol. 27, pp. 1-15.

Ohtsubo, K, et al., Glycosylation in cellular mechanisms of health and disease, Cell, Sep. 8, 2006, vol. 126, pp. 855-867.

Chen, S., et al., Analysis of cell surface carbohydrate expression patterns in normal and tumorigenic human breast cell lines using lectin arrays, Analytical Chemistry, Aug. 1, 2007, vol. 79, No. 15, pp. 5698-5702.

Dwek, M. V., et al., Breast cancer progression is associated with a reduction in the diversity of sialylated and neutral oligosaccharides, Clinica Chimica Acta., 1998, vol. 271, pp. 191-202.

Zhao, J., et al., Glycoprotein microarrays with multi-lectin detection: unique lectin binding patterns as a tool for classifying normal, chronic pancreatitis and pancreatic cancer sera, Journal of Proteome Research, Apr. 12, 2007, vol. 6, pp. 1864-1874.

Dwek, M. V., et al., A sensitive assay to measure biomarker glycosylation demonstrates increased fucosylation of prostate specific antigen (PSA) in patients with prostate cancer compared with benign prostatic hyperplasia, Clinica Chimica Acta, Aug. 12, 2010, vol. 411, pp. 1935-1939.

Jefferis, R. Glycosylation as a strategy to improve antibody-based therapeutics, Nat Rev Drug Discov., Mar. 2009, vol. 8, pp. 226-234.

Raju, T. S. Terminal sugars of Fc glycans influence antibody effector functions of IgGs, Current Opinion in Immunology, Jul. 17, 2008, vol. 20, pp. 471-478.

Burton, D. R., et al., Sugar determines antibody activity, Science, Aug. 4, 2006, vol. 313, pp. 627-628.

Marth, J. D., et al., Mammalian glycosylation in immunity, Nat Rev Immunol., Oct. 10, 2008, vol. 8, pp. 874-887.

Stancombe, P. R., et al., Isolation of the gene and large-scale expression and purification of recombinant *Erythrina cristagalli* lectin, Protein Expression and Purification, 2003, vol. 30, pp. 283-292.

Imberty, A., et al., Structural basis of high-affinity glycan recognition by bacterial and fungal lectins, Current Opinions in Structural Biology, Sep. 2, 2005, vol. 15, pp. 525-534.

Hu, D., et al., Directed evolution of lectins with sugar-binding specificity for 6-sulfo-galactose, Journal of Biological Chemistry, Apr. 5, 2012, vol. 287, pp. 20313-20320.

Yabe, R., et al., Tailoring a novel sialic acid-binding lectin from a ricin-B chain-like galactose-binding protein by natural evolution-mimicry, J. Biochem., Jan. 18, 2007, vol. 141, pp. 389-399.

Romano, P. R., et al., Development of recombinant *Aleuria aurantia* lectins with altered binding specificities to fucosylated glycans, Biochemical and Biophysical Research Communications, Sep. 14, 2011, vol. 414, pp. 84-89.

Gilboa-Garber, N., et al.,*Pseudomonas aeruginosa* lectins, In. Methods in Enzymology, 1982, Academic Press, pp. 378-385.

Imberty, A., et al., Structures of the lectins from *Pseudomonas aeruginosa*: insights into the molecular basis for host glycan recognition, Microbes and Infection, 2004, vol. 6, pp. 221-228.

Blanchard, B., et al., Structural basis of the preferential binding for globo-series glycosphingolipids displayed by *Pseudomonas aeruginosa* Lectin I, Journal of Molecular Biology, Aug. 22, 2008, vol. 383, pp. 837-853.

Beck, A., et al., Trends in glycosylation, glycoanalysis and glycoengineering of therapeutic antibodies and Fc-fusion proteins, Current Pharmaceutical Biotechnology, 2008, vol. 9, pp. 482-501.

Arnold, K., et al., The Swiss-Model workspace: a web-based environment for protein structure homology modelling, Bioinformatics, Nov. 13, 2005, vol. 22, pp. 195-201.

McNicholas, S., et al., Presenting your structures: the CCP4mg molecular-graphics software, Acta Crystallographica Section D, 2011, vol. 67, pp. 386-394.

Kirkeby, S., et al., Lectin interactions with a-galactosylated xenoantigens, Xenotransplantation, 2001, vol. 9, pp. 260-267.

Chen, C. P., et al., Studies on the binding site of the galactose-specific agglutinin PA-IL from *Pseudomonas aeruginosa*, Glycobiology, 1998, vol. 8, No. 1, pp. 7-16.

Cioci, G., et al., Structural basis of calcium and galactose recognition by the lectin PA-IL of *Pseudomonas aeruginosa*, FEBS Letters, Nov. 12, 2003, vol. 555, pp. 297-301.

Litterer, L., et al., Protein expression in less time: a short induction protocol for KRX, Promega Notes, May 2007, No. 96, pp. 20-21.

Gilboa-Garber, N., et al., The hemagglutinating activities of *Pseudomonas aeruginosa* lectins PA-IL and PA-IIL exhibit opposite temperature profiles due to different receptor types, FEMS Immunol. Med. Microbiol., 1999, vol. 25, pp. 365-369.

Thompson, R., et al., Optimization of the enzyme-linked lectin assay for enhanced glycoprotein and glycoconjugate analysis, Analytical Biochemistry, Feb. 12, 2011, vol. 413, pp. 114-122.

Gilboa-Garber, N., et al., Purification of the galactose-binding hemagglutinin of *Pseudomonas aeruginosa* by affinity column chromatography using sepharose, FEBS Letters, Nov. 1972, vol. 28, No. 1, pp. 93-95.

Wu, A. M. et al. Affinity of Bandeiraea (*Griffonia*) simplicifolia Lectin-I, Isolectin-B4 (BSI-B4) for Gala1-4Gal Ligand, Biochemical and Biophysical Research Communications, Nov. 22, 1995, vol. 216, No. 3, pp. 814-820.

Iskratsch, T., et al., Specificity analysis of lectins and antibodies using remodeled glycoproteins, Analytical Biochemistry, Dec. 14, 2008, vol. 386, pp. 133-146.

Trimble, R. B., et al., Structural heterogeneity in the Man8-13GlcNAc oligosaccharides from log-phase *Saccharomyces* yeast: a one- and two-dimensional 1H NMR spectroscopic study, Glycobiology, 1992, vol. 2, No. 1, pp. 57-75.

Wu, A., et al., Differential affinities of *Erythrina cristagalli* lectin (ECL) toward monosaccharides and polyvalent mammalian structural units, Glycoconjugate Journal, Sep. 6, 2007, vol. 24, pp. 591-604.

Wu, A., et al., Lectins as tools in glycoconjugate research, Glycoconjugate Journal, 2008, vol. 26, pp. 899-913.

Shields, R. L, et al., Lack of fucose on human IgG1 N-linked oligosaccharide improves binding to human FcgRIII and antibody-dependent cellular toxicity, Journal of Biological Chemistry, May 1, 2002, vol. 277, No. 30pp. 26733-26740.

Qiu, R., et al., Use of multidimensional lectin affinity chromatography in differential glycoproteomics, Anal. Chem., May 1, 2005, vol. 77, No. 9., pp. 2802-2809.

Geyer, H., et al. Strategies for analysis of glycoprotein glycosylation, Biochimica et Biophysica Acta (BBA)—Proteins & Proteomics, Oct. 24, 2006, vol. 1764, pp. 1853-1869.

Yang, Z., et al. Monitoring glycosylation pattern changes of glycoproteins using multi-lectin affinity chromatography, Journal of Chromatography A, Mary 7, 2005, vol. 1070, pp. 57-64.

(56) References Cited

OTHER PUBLICATIONS

Walsh, G., et al. Post-translational modifications in the context of therapeutic proteins, Nat. Biotech, Oct. 10, 2006, vol. 24, pp. 1241-1252.

Walsh, G. Biopharmaceutical benchmarks 2006, Nat. Biotech., Jul. 2006, vol. 24, No. 7, pp. 769-776.

Sinclair, A. M., et al., Glycoengineering: The effect of glycosylation on the properties of therapeutic proteins, Journal of Pharmaceutical Sciences, Aug. 2005, vol. 94, No. 8, pp. 1626-1635.

Werner, R. G., et al., Glycosylation of therapeutic proteins in different production systems, Acta Pmdiatrica, 2007, vol. 96, pp. 17-22.

Kim, H. J., et al. Antibody-based enzyme-linked lectin assay (ABELLA) for the sialylated recombinant human erythropoietin present in culture supernatant, Journal of Pharmaceutical and Biomedical Analysis, 2008, vol. 48, pp. 716-721.

Kobata, A., A journey to the world of glycobiology, Glycoconjugate Journal, 2000, vol. 17, pp. 443-464.

Xu, W., et al., Lectin Binding Assays for In-Process Monitoring of Sialylation in Protein Production, Molecular Biotechnology, Apr. 9, 2010, vol. 45, pp. 248-256.

Scallon, B. J., et al., Higher levels of sialylated Fc glycans in immunoglobulin G molecules can adversely impact functionality, Molecular Immunology, Oct. 11, 2006, vol. 44, pp. 1524-1534.

Oliveira, C., et al., Recombinant lectins: an array of tailor-made glycan-interaction biosynthetic tools, Critical Reviews in Biotechnology, Apr. 24, 2012, pp. 1-15.

McMAHON, K., Structural and Functional Characterisation of Lectins from the PA-IL Superfamily, Sep. 2, 2012, Ph.D. Thesis, pp. 1-260.

* cited by examiner

Figure 1: Structure of the PA-IL Protein.
(A) (B)
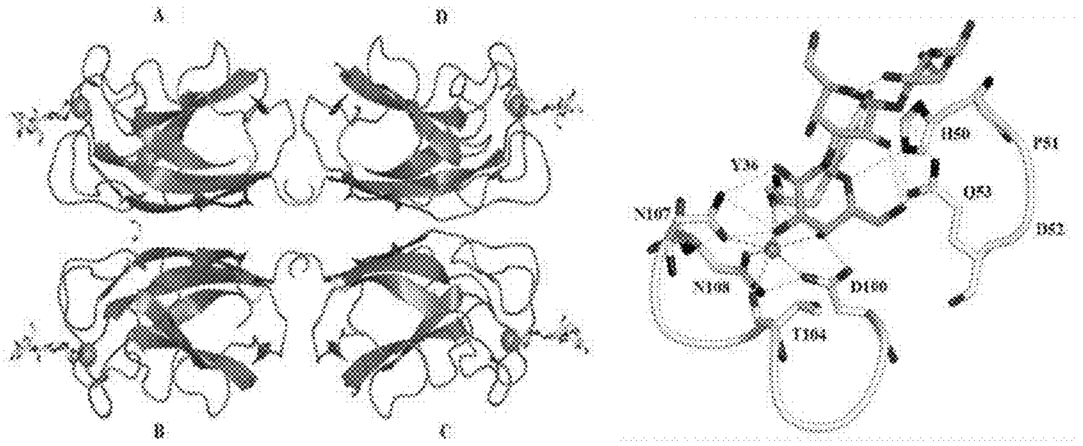
Figure 2: Qualitative ELLA Screening of Random rPA-ILNm Proteins:
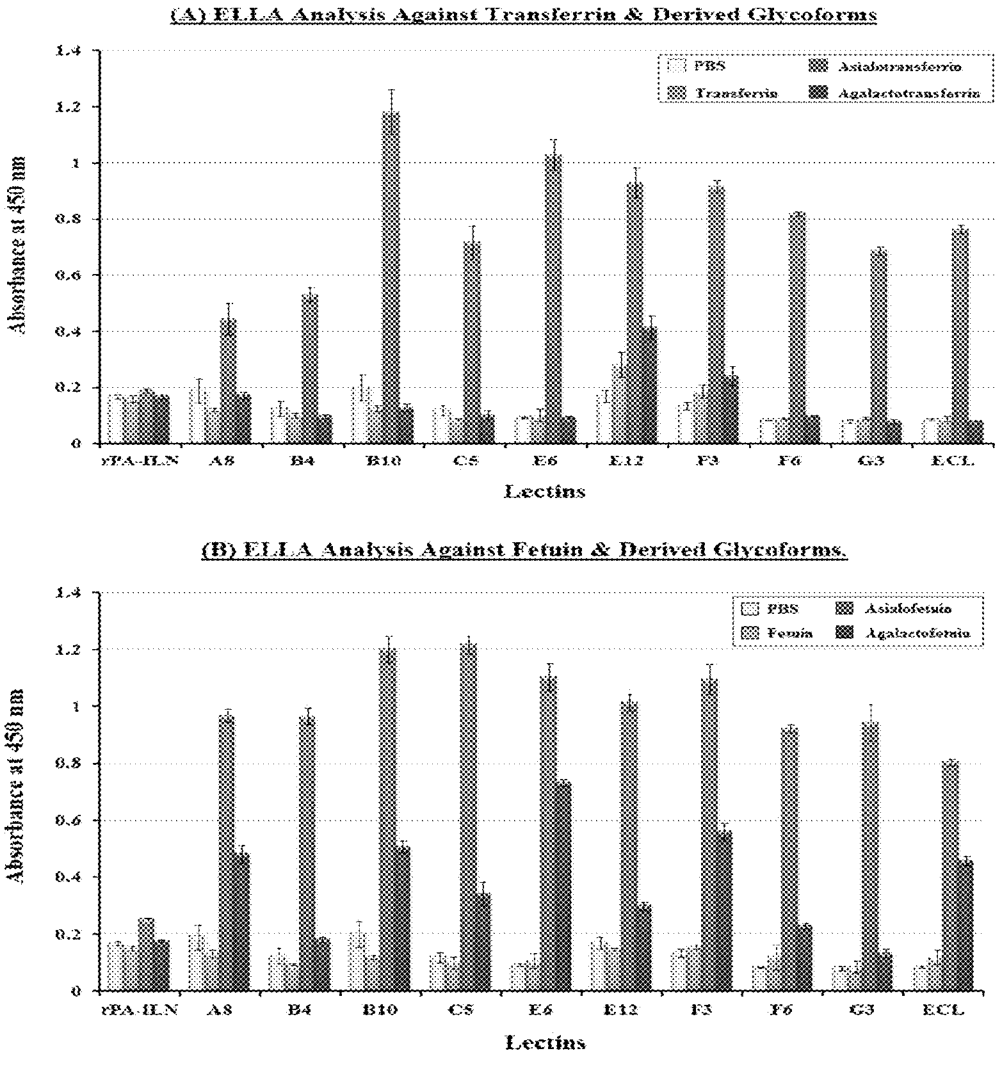

Figure 3: Identification of Amino Acid Substitutions Present in Isolated rPA-ILNm Proteins.

| | | 45 | 50 | | 52 | 53 | | 58 |
|---|---|---|---|---|---|---|---|---|
| rPA-ILN | : | QGDRE- | H | F | D | Q | -GLIC | H |
| rPA-ILNmE12 | : | QGDRE- | G | F | C | R | -GLIC | H |
| rPA-ILNmF3 | : | QGDRE- | V | F | C | R | -GLIC | H |
| rPA-ILNmB10 | : | QGDRE- | V | F | C | E | -GLIC | H |
| rPA-ILNmG3 | : | QGDRE- | V | F | N | N | -GLIC | H |
| rPA-ILNmB4 | : | QGDRE- | T | P | N | R | -GLIC | H |
| rPA-ILNmE6 | : | QGDRE- | N | F | N | G | -GLIC | H |
| rPA-ILNmC5 | : | QGDRE- | N | P | T | S | -GLIC | H |
| rPA-ILNmA8 | : | QGDRE- | L | F | H | R | -GLIC | H |
| rPA-ILNmF6 | : | QGDRE- | P | P | R | L | -GLIC | H |

Figure 4: Lectin Dilution Response Curves for Defined BSA Glycoconjugates.

(A) BSA-LacNAc Response Curves

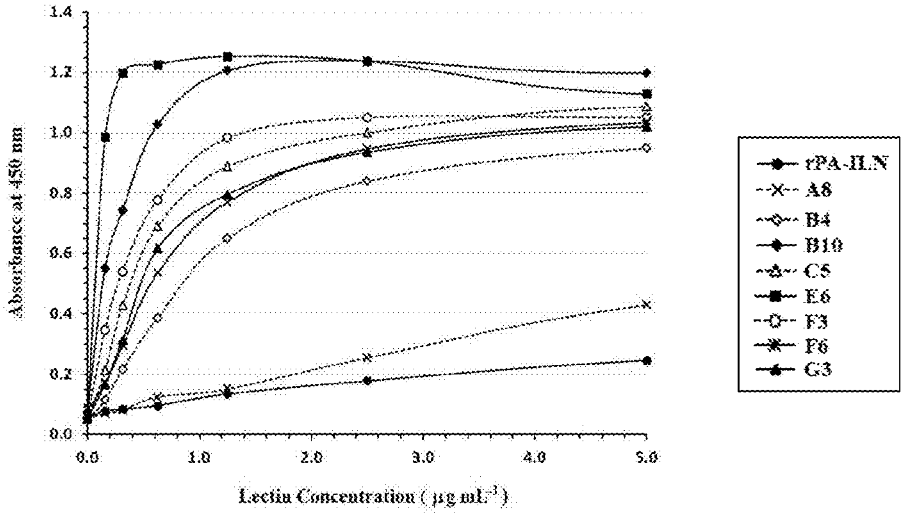

(B) BSA-αGal Response Curves

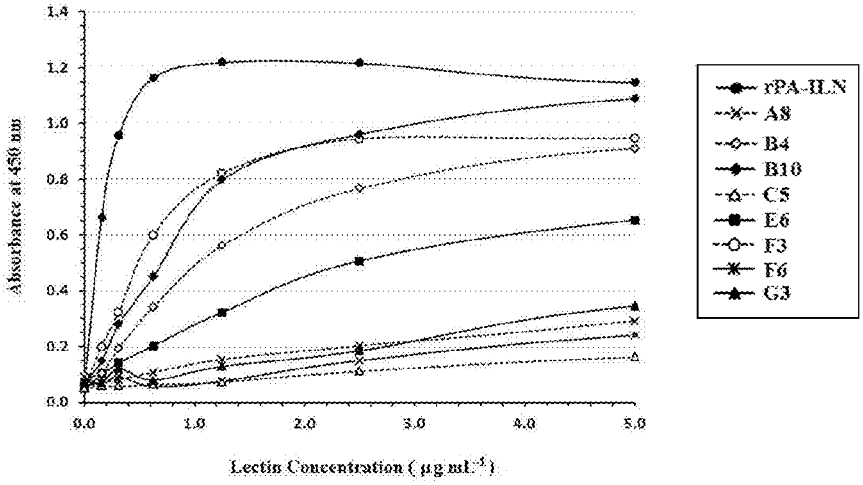

Figure 4 (contd): Lectin Dilution Response Curves for Defined BSA Glycoconjugates.
(C) BSA-αGal versus BSA-LacNAc
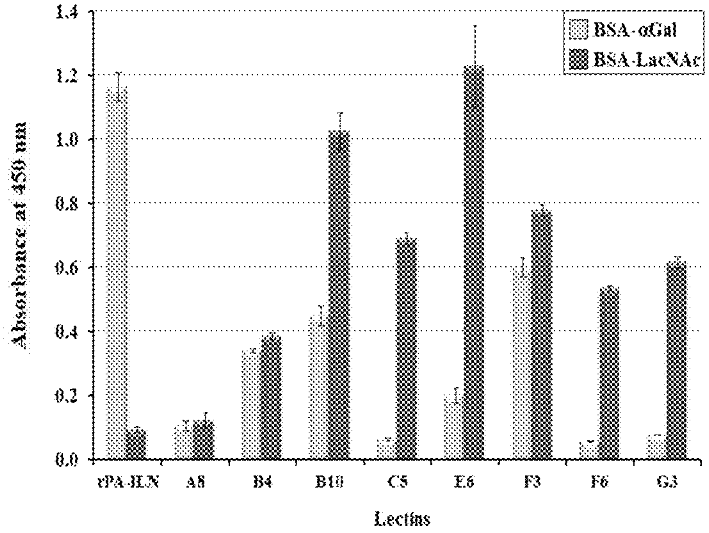

Figure 5: Evaluation of rPA-ILNm Binding to Natural Glycoprotein Targets:
(A) Asialotransferrin Response Curves
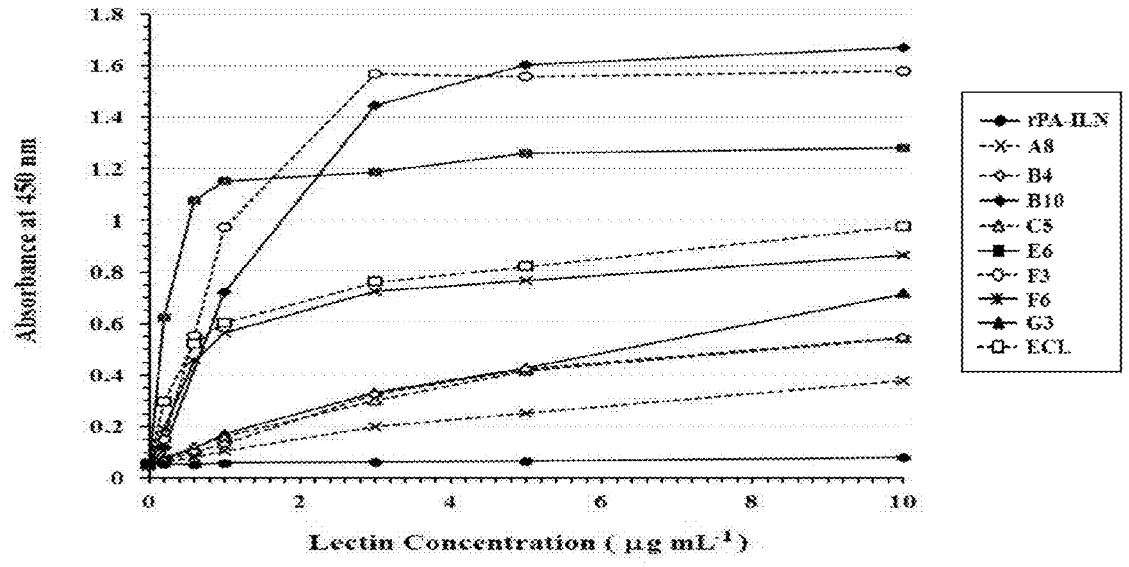
(B) Asialofetuin Response Curves
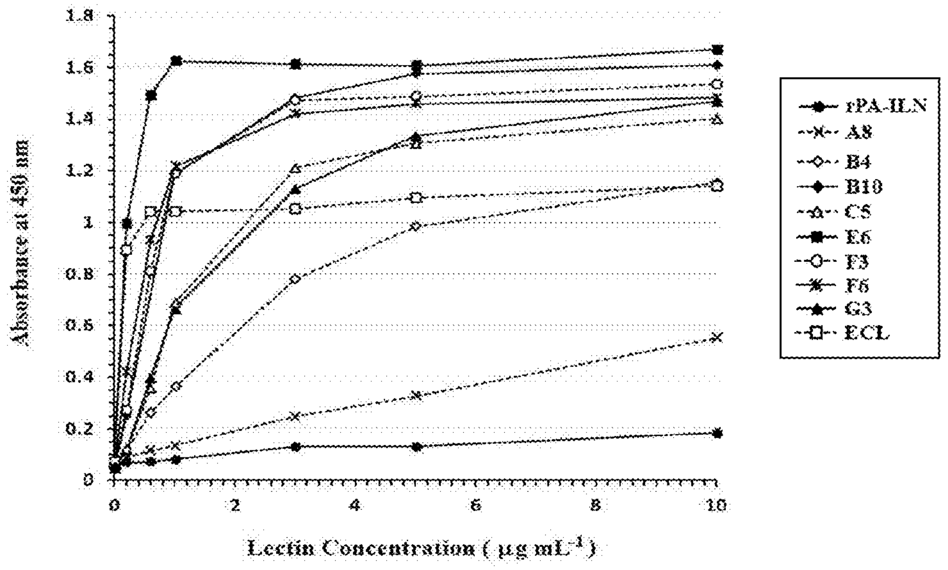

Figure 6: Determination of Affinity Constants for rPA-ILNm Proteins against BSA-LacNAc
| Lectin | Conc. µg mL$^{-1}$ | $B_{max}$ (au) | ½ $B_{max}$ (au) | $K_D$ ng |
|---|---|---|---|---|
| rPA-ILN | 2 | N.D. | - | - |
| rPA-ILNmA8 | N.D | N.D. | - | - |
| rPA-ILNmB4 | 2 | 0.53 | 0.27 | 47.5 |
| rPA-ILNmB10 | 2 | 1.01 | 0.51 | 15 |
| rPA-ILNmC5 | 2 | 1.07 | 0.53 | 51 |
| rPA-ILNmE6 | 2 | 1.41 | 0.71 | 4 |
| rPA-ILNmF3 | 2 | 1.27 | 0.63 | 6.3 |
| rPA-ILNmF6 | 2 | 0.98 | 0.49 | 52.2 |
| rPA-ILNmG3 | 2 | 0.72 | 0.36 | 62 |
| ECL | 4 | 0.70 | 0.35 | 21 |
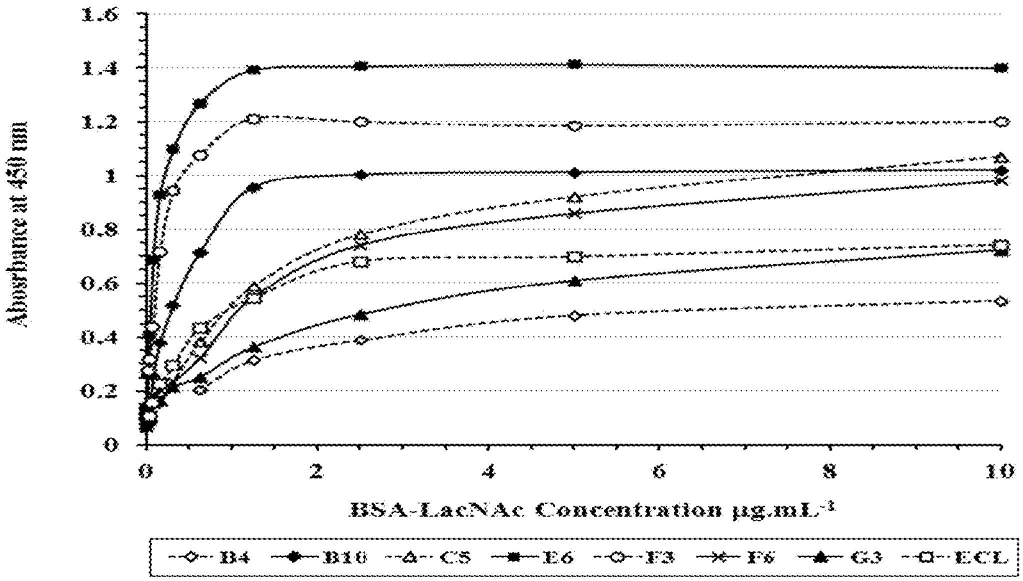

Figure 7: The Application of rPA-ILNmE6 for the Separation and Selective Purification of Glycoproteins and Glycoforms Displaying Terminal β1,4-Linked Galactose
(A)
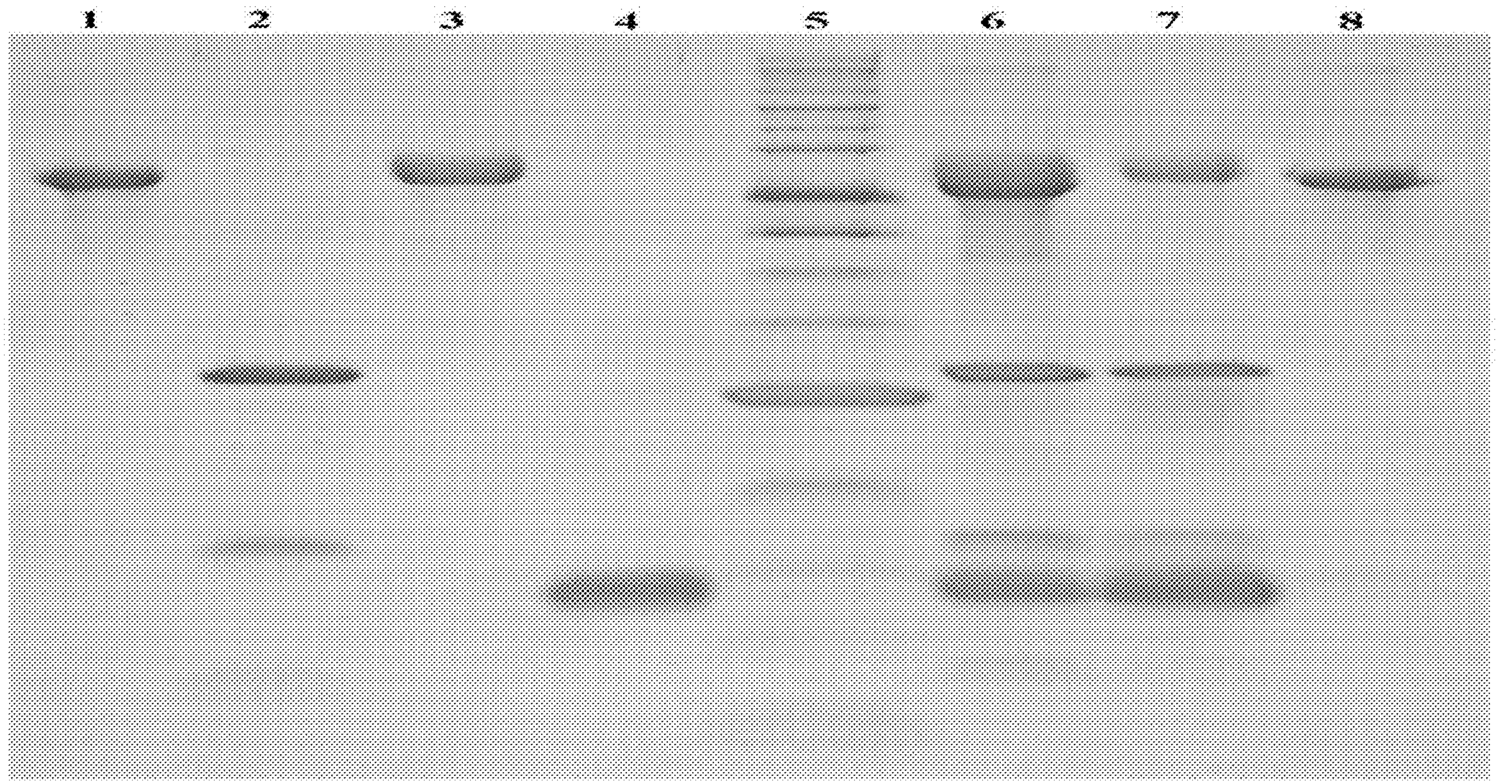

Figure 7: contd.
(B)
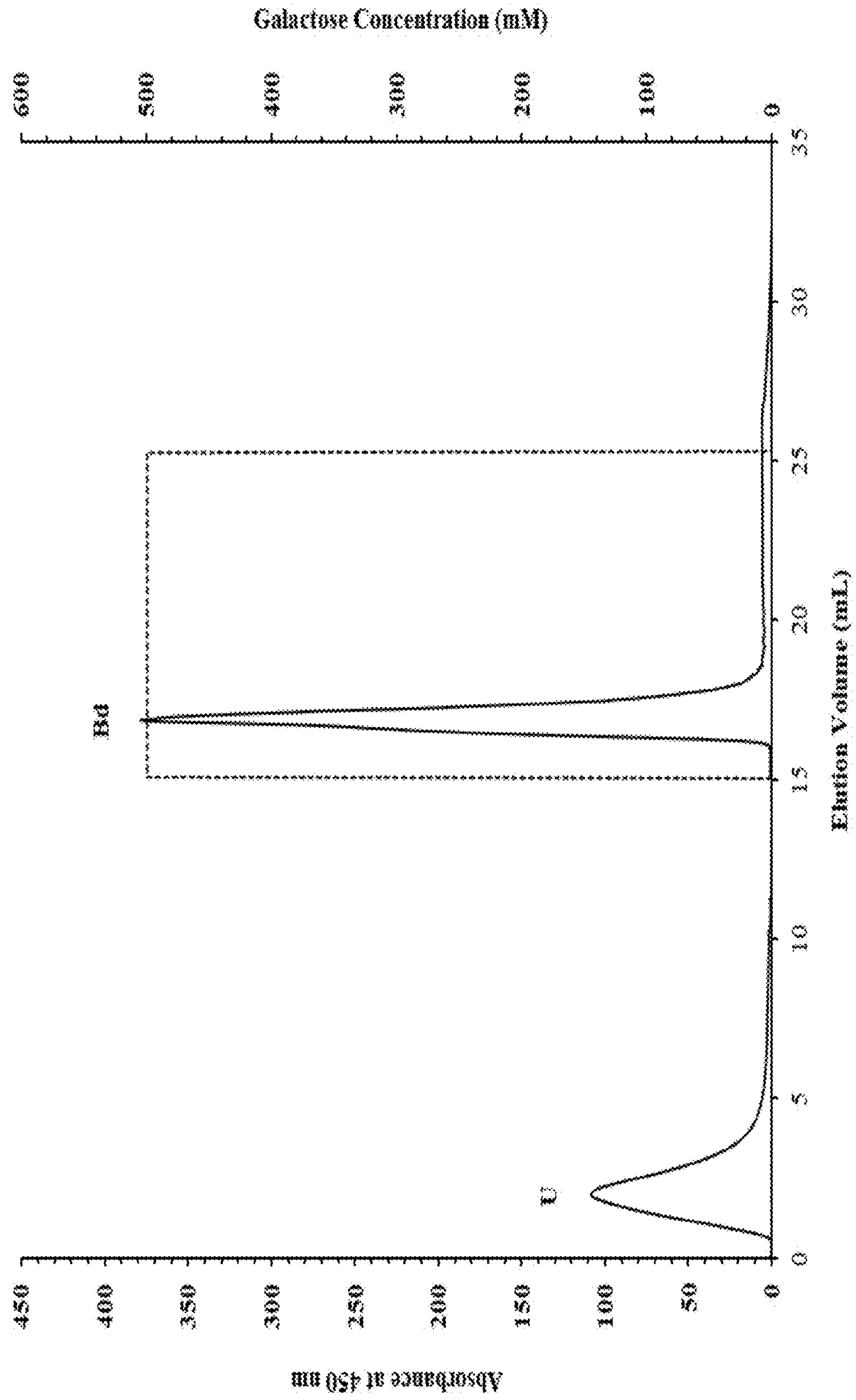

Figure 7: contd.
(C)
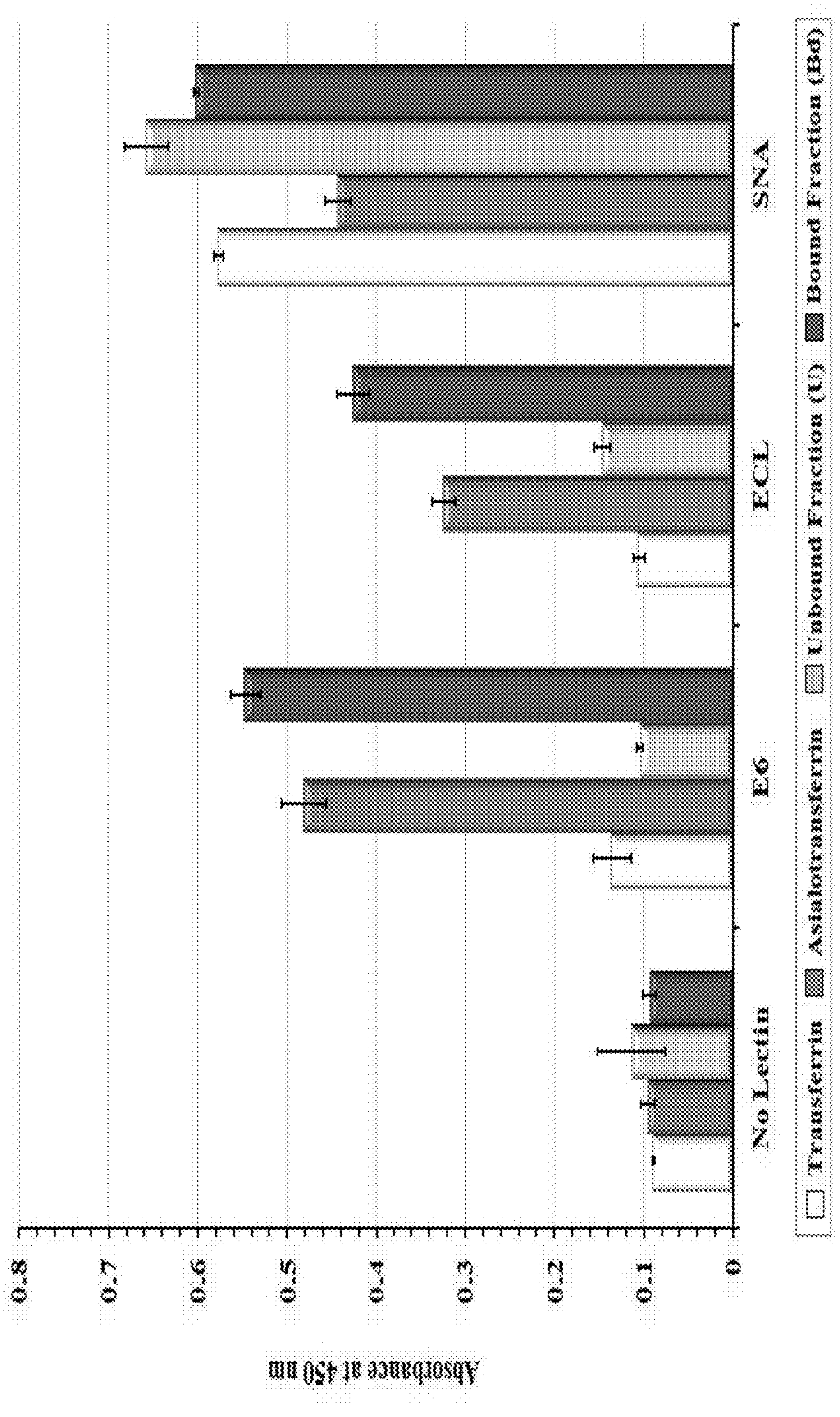

Figure 8: Expression Vectors Constructed for Expression of rPA-IL Proteins.
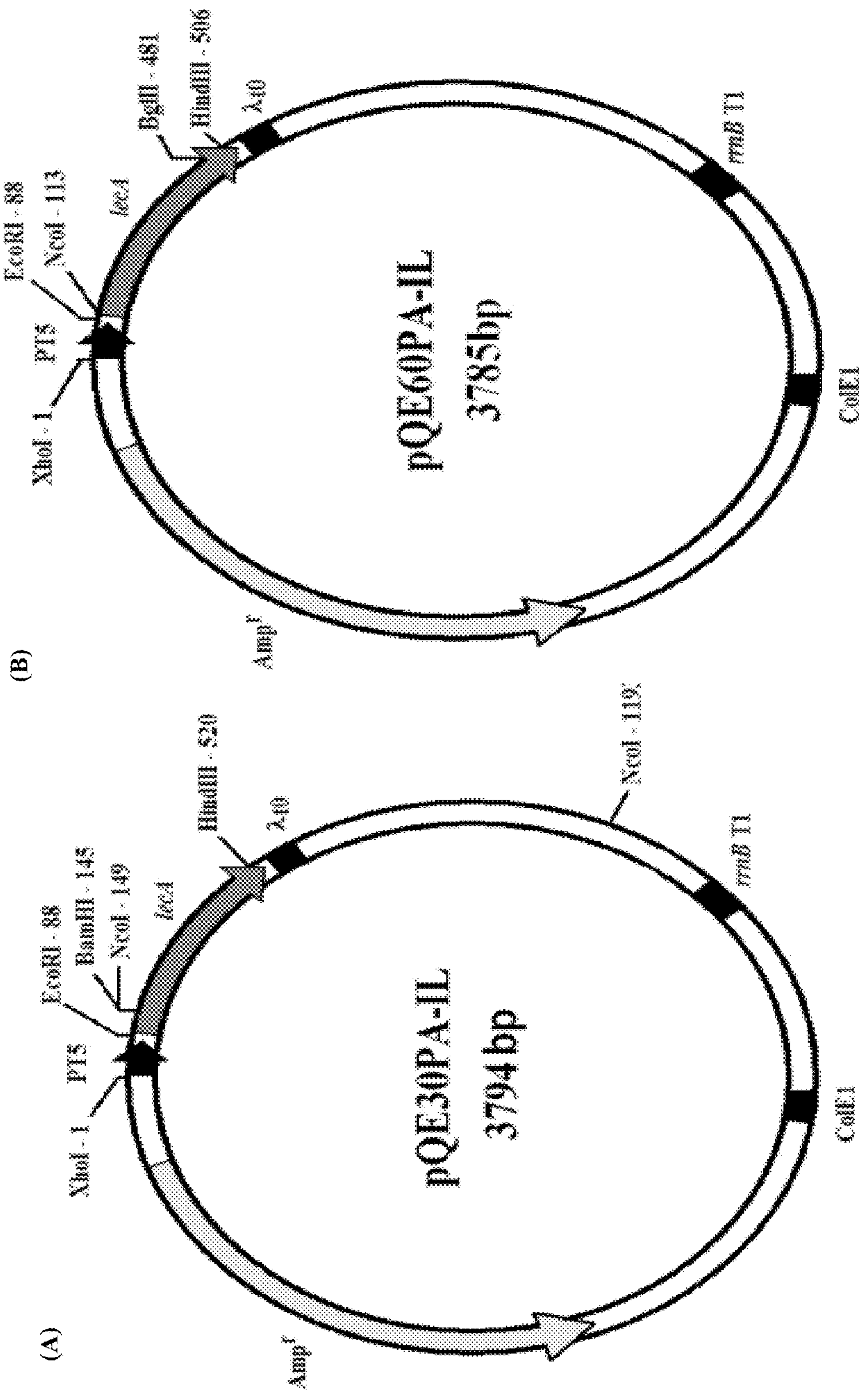

Figure 8: contd. (C) The Coding Region of pQE30PA-IL.

RBS RGS-6HIS Affinity Tag BamHI

GAATTCATTAAAGAGGAGAAATTAACTATGAGAGGATCGCATCACCATCACCATCACGGATCCATGGCTTGGAAA

PA-ILmutR

---------------AGAAATGGGGGCCGCAGGGCGATCGGGAG*CAT*CCG*GACCAA*GGGCTGATCTGCCACGATG

PA-ILmutF

CGTTTTGTGGTGCGCTGGTCATGAAGATTGGCAACAGCGGAACCATTCCGGTCAATACCGGGTTGTTCCGTTGGG

HindIII

-------------------------------GCTCGTTCAGTGTCAATATTGGAAAGGATCAGTCCTGAAAGCTT

(D) The Coding Region of pQE60PA-IL.

GAATTCATTAAAGAGGAGAAATTAACCATGGCTTGGAAAGGTGAGGTTCTGGCTAATAACGAAGCAGGGCAGGTA

BglII 6HIS Tag HindIII

-------------ATCAGTCCAGATCTCATCACCATCACCATCACTAAGCTTAATTAGCT

(E) Amino Acid Sequences of rPA-IL Proteins.

rPA-ILN
MRGSHHHHHHGSMAWKGEVLANNEAGQVTSIIYNPGDVITIVAAGWASYGPTQKWGPQGDREHPDQGLICHDAFCGALVMKIG
NSGTIPVNTGLFRWVAPNNVQGAITLIYNDVPGTYGNNSGSFSVNIGKDQS rPA-ILC
MAWKGEVLANNEAGQVTSIIYNPGDVITIVAAGWASYGPTQKWGPQGDREHPDQGLICHDAFCGALVMKIGNSGTIPVNTGLF
RWVAPNNVQGAITLIYNDVPGTYGNNSGSFSVNIGKDQSRSHHHHHH

Figure 9: SDS-PAGE Analysis of PA-IL Proteins.

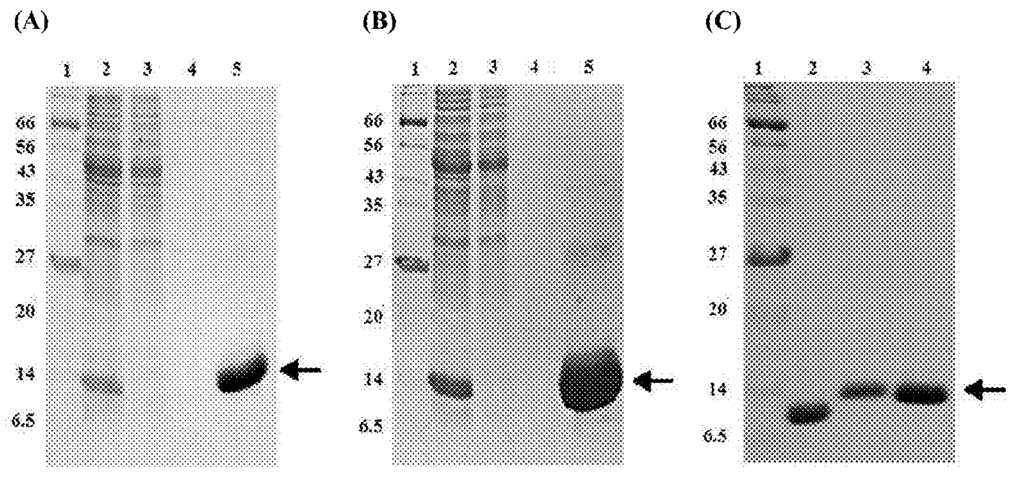

Figure 10: GPC Analysis of PA-ILU, rPA-ILC and rPA-ILN.
| Standards | $V_e$ (mL) | $K_{av}$ | MW(kDa) |
|---|---|---|---|
| BSA | 9.87 | 0.8242 | 67 |
| Ovalbumin | 10.58 | 0.7658 | 45 |
| Carbonic Anhydrase | 11.78 | 0.6672 | 27 |
| Myoglobin | 12.52 | 0.6064 | 17 |
| Cytochrome C | 13.2 | 0.5505 | 12.3 |
| **Test Proteins** | | | $MW_e$ |
| PA-ILU | 10.81 | 0.7469 | 41.5 |
| rPA-ILC | 10.87 | 0.7420 | 40.3 |
| rPA-ILN | 12.29 | 0.6253 | 19.6 |
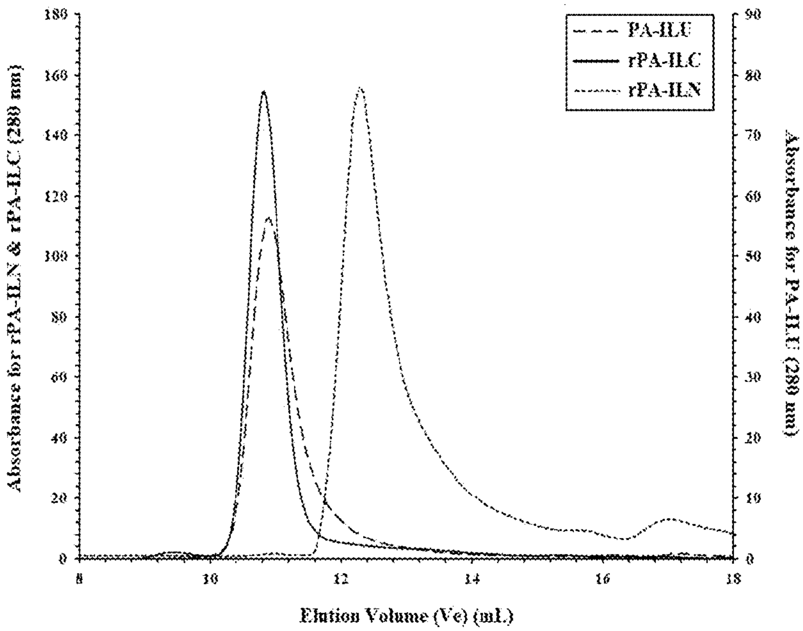
Figure 11: Functional Analysis of the rPA-IL Proteins Using the Hemagglutination Assay:
(A) Hemagglutination Assay (B) Hemagglutination Inhibition Assay
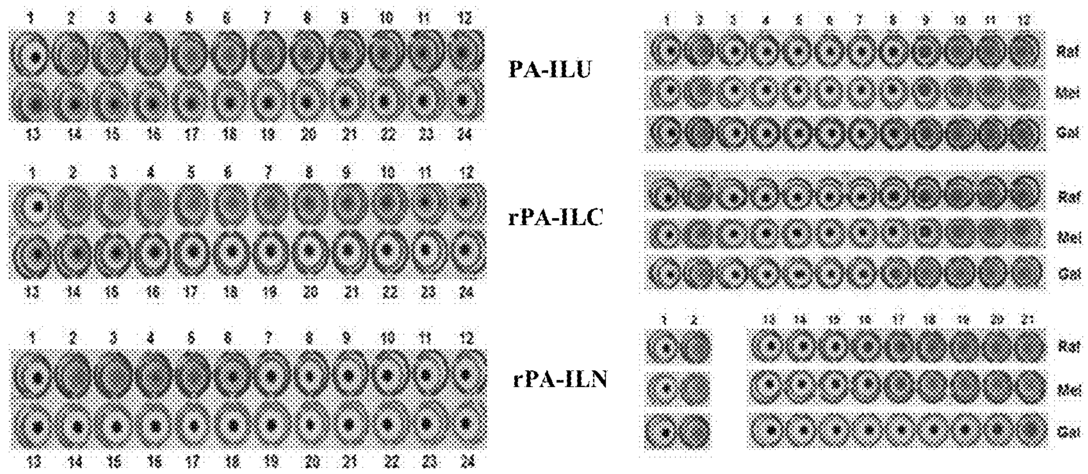

Figure 12: Functional Analysis of rPA-IL Proteins by ELLA.
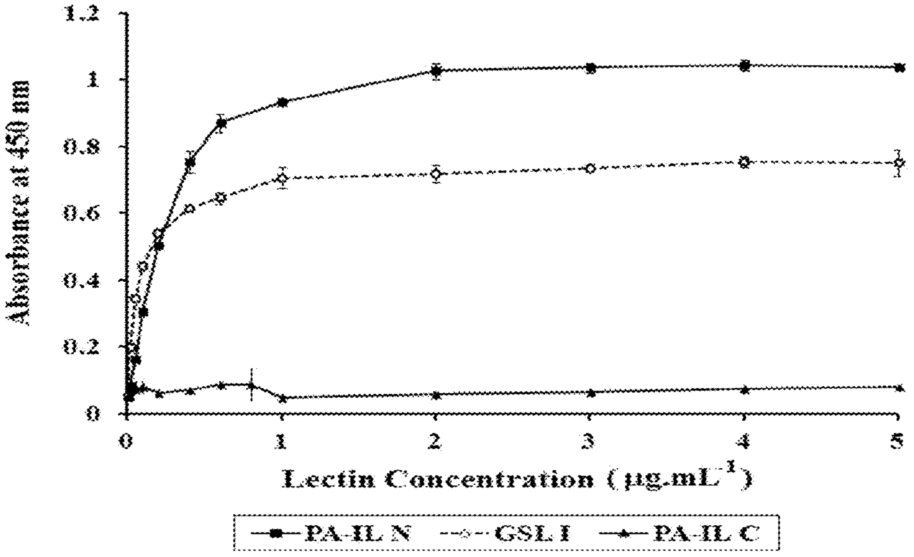
Figure 13: Qualitative ELLA analysis of rPA-ILNm proteins carrying His50 substitutions.
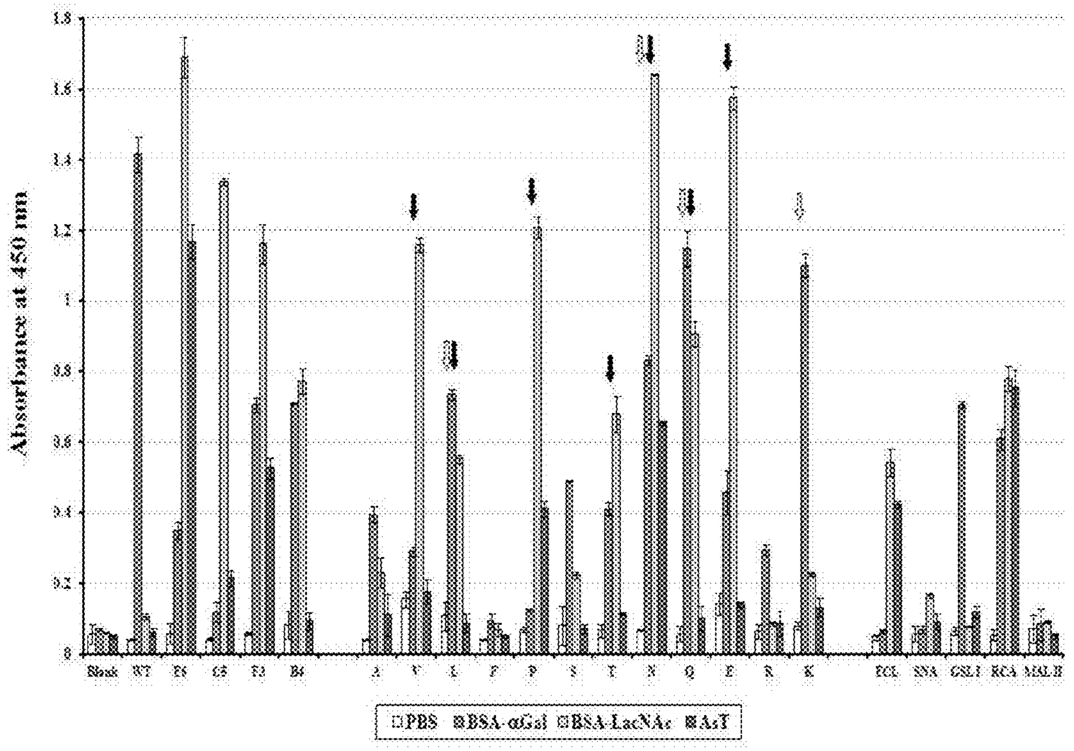

Figure 14: Lectin dose response curves for selected His50 substituted rPA-ILNm proteins.
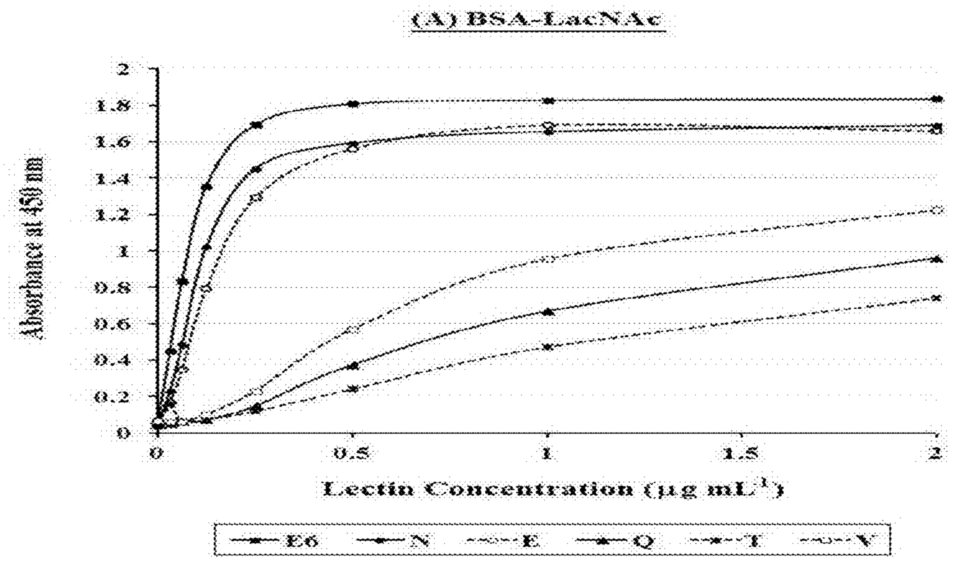
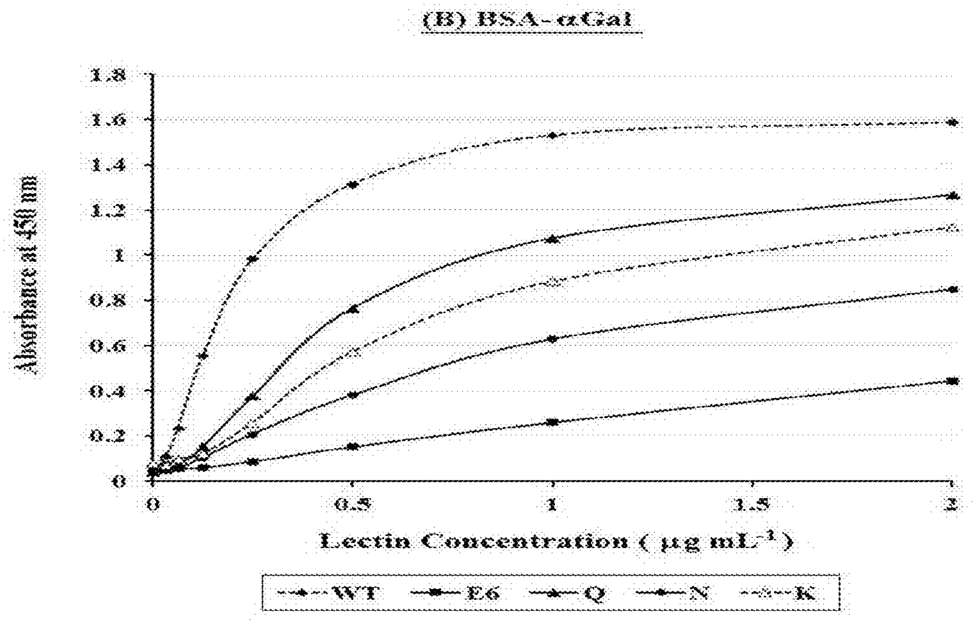

Figure 15: Qualitative ELLA analysis of H50N proteins with additional Gln53 substitutions.
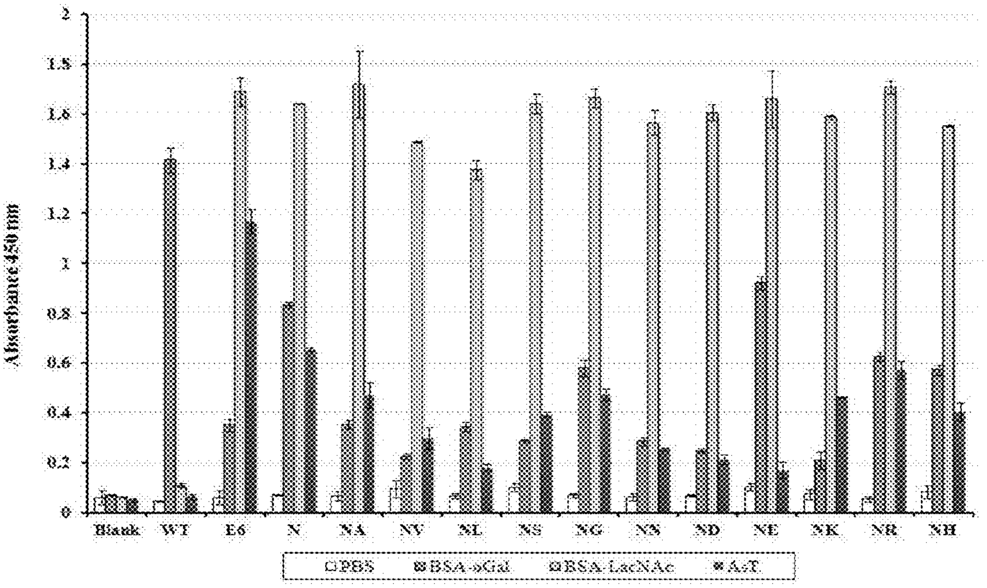
Figure 16: The role of a Q53R substitution in promoting binding to α-linked galactose:
(A)
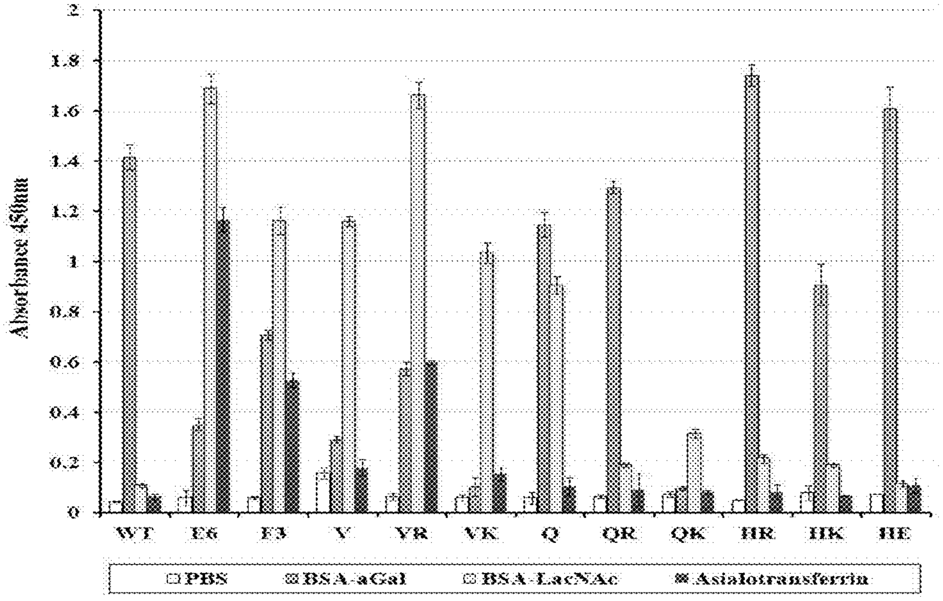

Figure 16 (contd): The role of a Q53R substitution in promoting binding to α-linked galactose:
(B)
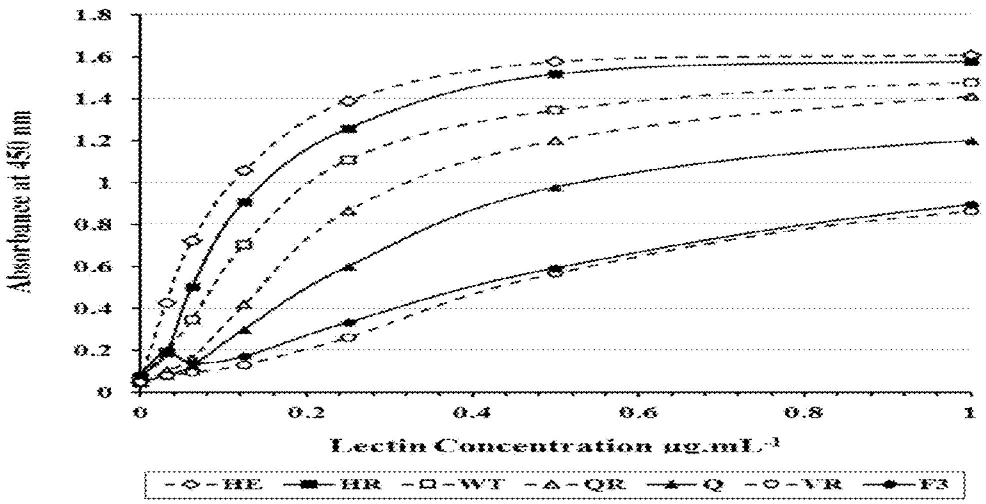
Figure 17: Structural models depicting the probable steric role played by the amino acid at position 50 in determining the linkage specificity of PA-IL proteins.
(A)
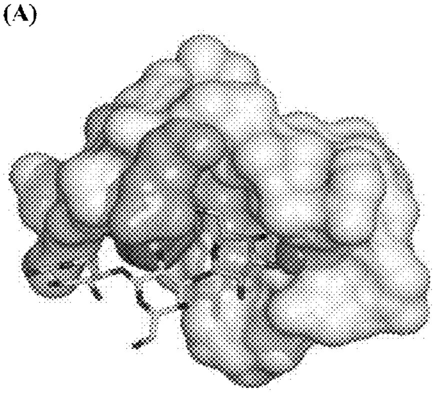
(B)
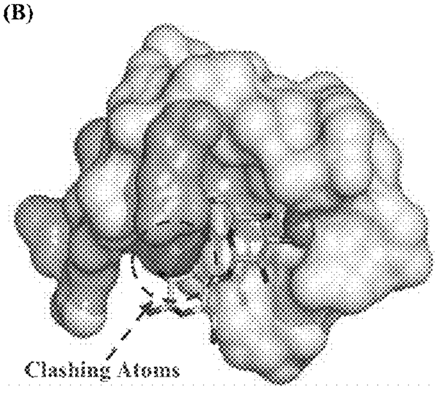
(C)
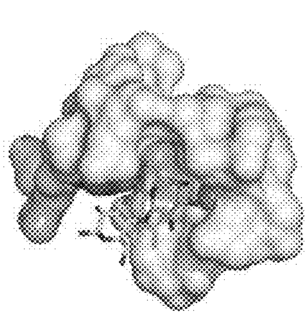
(D)
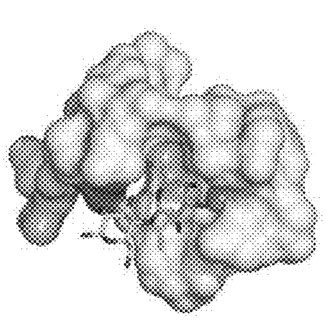
(E)
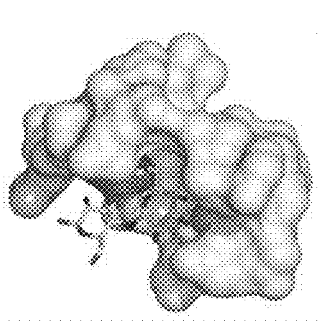

Figure 18: Structural models of rPA-ILNm mutants with bound lactose (Gal-β1,4-Glc).
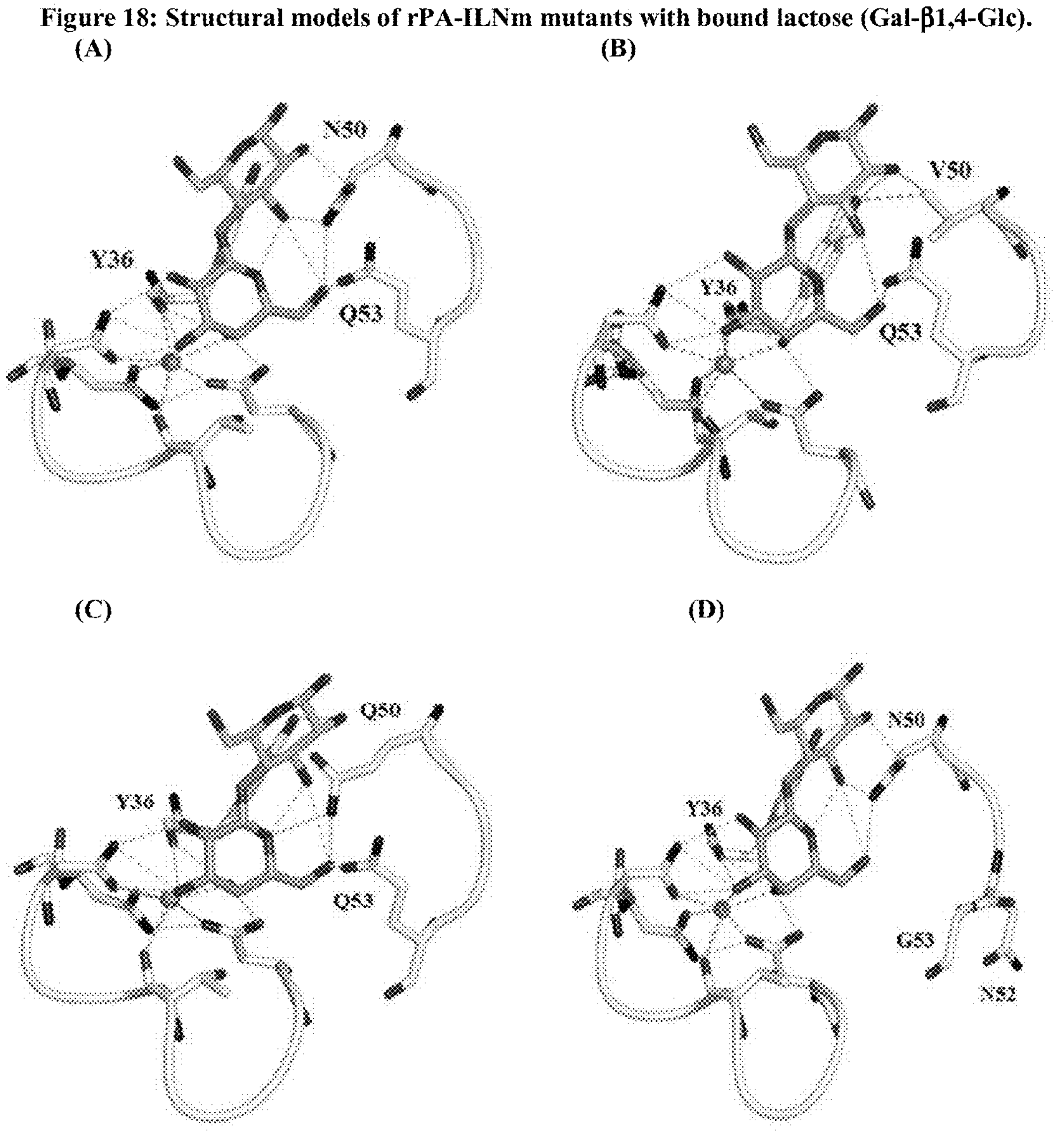

Figure 19: Structural models of rPA-ILNm mutants with bound iGb3 (Gal-α1,3-Gal-β1,4-Glc).

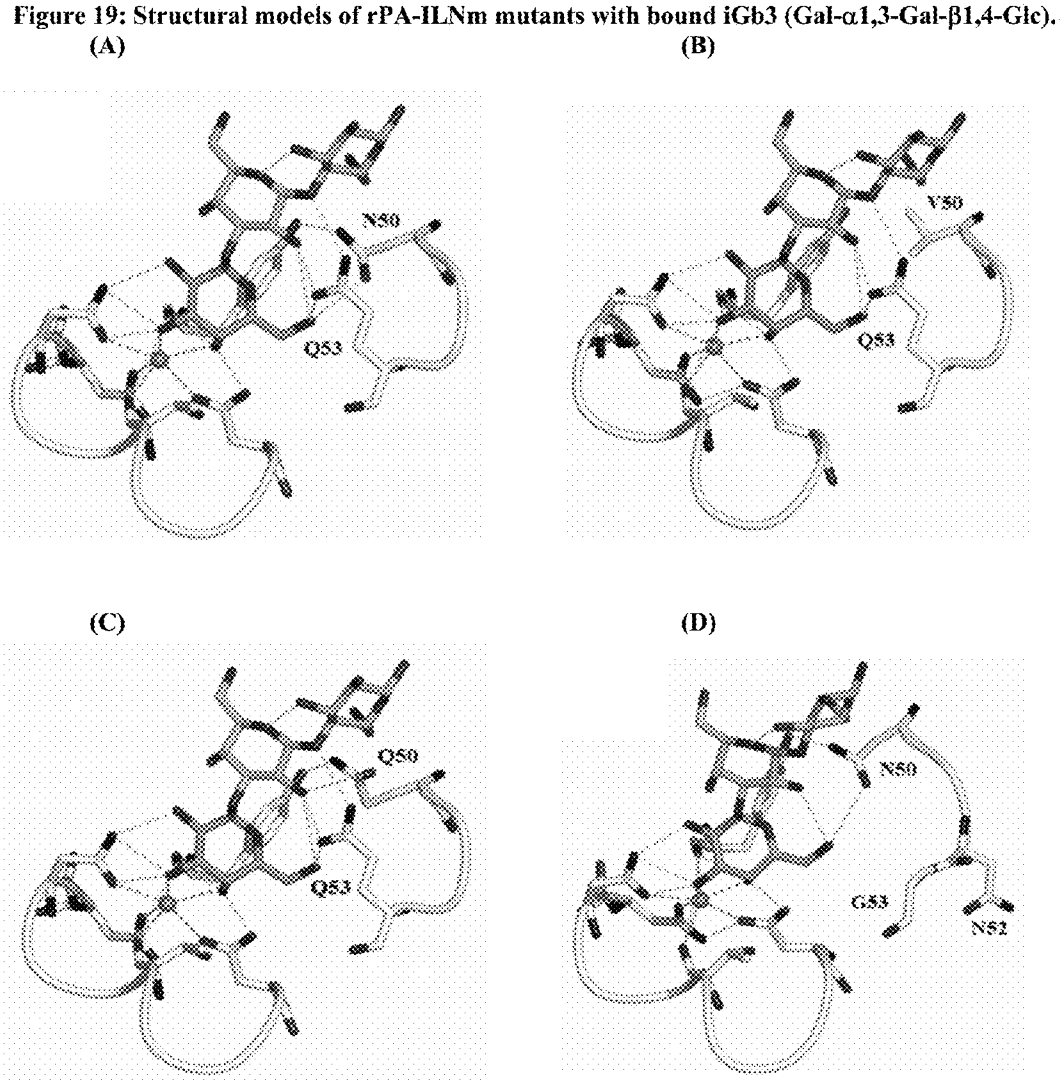

Figure 20: Amino Acid Sequences of the rPA-ILN Protein and Derived Mutants (rPA-ILNm)

>rPA-ILN - SEQ ID NO: 1
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu <u>His</u>Pro <u>Asp Gln</u> Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

Figure 20: contd.

Three Simultaneous Substitutions at His50, Asp52 and Gln53 (Example A)

>rPA-ILNmA8(H50L:D52H:Q53R) - SEQ ID NO: 2
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Leu Pro His Arg Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>rPA-ILNmB4(H50T:D52N:Q53R) - SEQ ID NO: 3
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Thr Pro Asn Arg Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>rPA-ILNmB10(H50V:D52C:Q53E) - SEQ ID NO: 4
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Val Pro Cys Glu Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>rPA-ILNmC5 (H50N:D52T:Q53S) - SEQ ID NO: 5
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Thr Ser Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>rPA-ILNmE6 (H50N:D52N:Q53G) - SEQ ID NO: 6
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asn Gly Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>rPA-ILNmE12 (H50G:D52C:Q53R) - SEQ ID NO: 7
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Gly Pro Cys Arg Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val

Figure 20: contd.

Pro Gly Thr Tyr Gly Asn Asn Ser Gly Ser Phe Ser Val Asn Ile Gly Lys Asp Gln
Ser

>rPA-ILNmF3(H50V:D52C:Q53R) - SEQ ID NO: 8
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Val Pro Cys Arg Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>rPA-ILNmF6(H50P:D52R:Q53L) - SEQ ID NO: 9
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Pro Pro Arg Leu Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>rPA-ILNmG3(H50V:D52N:Q53N) - SEQ ID NO: 10
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Val Pro Asn Asn Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

Mutants with Single H50 Substitutions (Example B)

>H50A - SEQ ID NO: 11
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Ala Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50V - SEQ ID NO: 12
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Val Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50L - SEQ ID NO: 13
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val

Figure 20: contd.

Ile Thr Ile Val Ala Ala Gly Trp Ala Ser Tyr Gly Pro Thr Gln Lys Trp Gly Pro
Gln Gly Asp Arg Glu Leu Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50F - SEQ ID NO: 14
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Phe Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50P - SEQ ID NO: 15
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Pro Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50S - SEQ ID NO: 16
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Ser Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50T - SEQ ID NO: 17
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Thr Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50N - SEQ ID NO: 18
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50Q - SEQ ID NO: 19

Figure 20: contd.

Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Gln Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50D - SEQ ID NO: 20
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asp Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50E - SEQ ID NO: 21
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Glu Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50K - SEQ ID NO: 22
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Lys Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50R - SEQ ID NO: 23
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Arg Pro Asp Gln Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

Mutants with a H50N Substitution in Combination withAlternative Q53 Substitutions (Example B).

>H50N:Q53A - SEQ ID NO: 24
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp Ala Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val

Figure 20: contd.

Pro Gly Thr Tyr Gly Asn Asn Ser Gly Ser Phe Ser Val Asn Ile Gly Lys Asp Gln
Ser

>H50N:Q53V - SEQ ID NO: 25
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp Val Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50N:Q53L - SEQ ID NO: 26
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp Leu Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50N:Q53G - SEQ ID NO: 27
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp Gly Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50N:Q53Y - SEQ ID NO: 28
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp Tyr Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50N:Q53N - SEQ ID NO: 29
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp Asn Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50N:Q53D - SEQ ID NO: 30
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp Asp Gly Leu Ile Cys His Asp Ala Phe Cys Gly

Figure 20: contd.

Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50N:Q53E - SEQ ID NO: 31
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp Glu Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50N:Q53K - SEQ ID NO: 32
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp Lys Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50N:Q53R - SEQ ID NO: 33
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp Arg Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50N:Q53H - SEQ ID NO: 34
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Asn Pro Asp His Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

Additional Mutants Made with Double His50 and Gln53 Substitutions (Example B).

>H50V:Q53R - SEQ ID NO: 35
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Val Pro Asp Arg Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50V:Q53K - SEQ ID NO: 36

Figure 20: contd.

Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Val Pro Asp Lys Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50Q:Q53R - SEQ ID NO: 37
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Gln Pro Asp Arg Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>H50Q:Q53K - SEQ ID NO: 38
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu Gln Pro Asp Lys Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

Additional Mutants with Single Gln53 Substitutions (Example B).

>Q53R - SEQ ID NO: 39
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu His Pro Asp Arg Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>Q53K - SEQ ID NO: 40
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu His Pro Asp Lys Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

>Q53E - SEQ ID NO: 41
Met Arg Gly Ser His His His His His His Gly Ser Met Ala Trp Lys Gly Glu Val
Leu Ala Asn Asn Glu Ala Gly Gln Val Thr Ser Ile Ile Tyr Asn Pro Gly Asp Val
Ile Thr Ile Val Ala Ala Gly Trp Ala Ser Tyr Gly Pro Thr Gln Lys Trp Gly Pro
Gln Gly Asp Arg Glu His Pro Asp Glu Gly Leu Ile Cys His Asp Ala Phe Cys Gly
Ala Leu Val Met Lys Ile Gly Asn Ser Gly Thr Ile Pro Val Asn Thr Gly Leu Phe
Arg Trp Val Ala Pro Asn Asn Val Gln Gly Ala Ile Thr Leu Ile Tyr Asn Asp Val
Pro Gly Thr Tyr Gly Asn Asn Ser Gly Ser Phe Ser Val Asn Ile Gly Lys Asp Gln
Ser

PEPTIDE ANALOGUES OF PA-IL AND THEIR UTILITY FOR GLYCAN AND GLYCOCONJUGATE ANALYSIS AND PURIFICATION

INTRODUCTION

Glycosylation is one of the most abundant and biologically significant post-translational modifications to occur in cells. It is a highly complex non-template driven process that results in the addition of oligosaccharide moieties to a variety of biomolecules. Cell surfaces, both prokaryotic and eukaryotic, are covered in a dense layer of complex oligosaccharide structures that are attached to proteins and lipids. This layer is called the "glycocalyx" and the nature of the glycans displayed can be organism and cell type specific. As the interface between a cell and its environment it is not surprising that interactions between these glycans with carbohydrate binding proteins, called lectins, mediate a vast array of biological processes, play a central role in the orchestration of the immune system and mediate interactions between cells and various infectious agents such as prions, viruses and microorganisms. The glycans present on proteins also have a very significant impact on their physiochemical properties and biological activity. Changes in the glycans presented on glycoproteins or cell surfaces can result in, or be indicative of, changes in the physiological status of a cell or signify the development of a disease state (1-6) including many types of cancer (7-10) and autoimmune disorders such as rheumatoid arthritis (11-14). Many biopharmaceutical molecules are also glycosylated proteins and the glycans attached to these products can have a significant impact on their safety and efficacy. Given the biological significance of glycosylation, there is a requirement for methods that enable efficient isolation of glycosylated biomolecules and informative glycoanalysis of biomolecules and cell surfaces.

Lectins are carbohydrate proteins that are capable of recognizing and binding reversibly to specific carbohydrate structures. They display exquisite specificity for their cognate glycans and their ability to discriminate between different glycan structures has been exploited for many years for glycoanalytical applications. Their ability to bind to glycans in situ on proteins and cell surfaces, without the need for prior release and derivatization, makes them particularly attractive when compared to alternative MS and HPLC based approaches as these treatments can often result in the loss of significant biological data. When immobilized to solid support matrices, lectins can be used to effect the separation and purification of glycosylated molecules. Lectin affinity chromatography is often used as a preliminary step to isolate or separate oligosaccharides, glycopeptides, glycoproteins and glycoprotein glycoforms to facilitate their identification and characterisation.

The most commonly used lectins are plant lectins and these have traditionally exhibited significant problems, particularly with respect to product quality and performance. Many plant lectins are purified from source material, due to incompatibility with recombinant production methods, and this results in batch to batch variations and variability from one supplier to another (5,15,16). Production methods usually generate relatively low yields and final products are expensive which has meant that lectins have been restricted to analytical scale applications where only small quantities are required (16).

Prokaryotic lectins offer new opportunities for the development of superior glycoselective bioaffinity tools but, to date, they have been relatively underexploited. They usually exhibit greater affinities for their glycan targets and less structural complexity than plant lectins (17). They are also more amenable to recombinant production, particularly in *Escherichia coli*, which simplifies production but also opens up opportunities for the development of novel enhanced recombinant prokaryotic lectins (RPL's) with diversified and optimized binding properties (18-20).

We will demonstrate herein how the carbohydrate binding properties of the α-galactophilic PA-IL protein, from the opportunistic pathogen *Pseudomonas aeruginosa* (21-23), were significantly altered through random mutagenesis of specific amino acid residues in the proteins carbohydrate binding site. We will generate a series of novel RPL's that exhibit specificity and high affinity for glycoprotein targets displaying lactosamine (LacNAc) and demonstrate that binding was dependent on terminal β1,4-linked galactose. Lactosamine is commonly displayed as part of glycan structures found on cell surfaces and as part of the antenna of N-linked glycans displayed on glycoproteins including serum IgG's where it is important for the ability of these molecules to elicit CDC (complement dependent cytotoxicity) and ADCC (antibody dependent cellular cytotoxicity) effector functions (11, 12,14,24). RPL's with specificity for LacNAc therefore represent potentially valuable tools for glycoselective applications throughout the life sciences.

These novel RPL's carried multiple simultaneous substitutions in the carbohydrate binding site of the PA-IL (*Pseudomonas aeruginosa* lectin 1 or *Pseudomonas aeruginosa* lectin I) protein. As a result, it was difficult to fully determine the specific contribution of individual substitutions to the observed carbohydrate binding properties of the mutant PA-IL proteins. In this work, we also undertook a progressive site directed mutagenesis approach to assess the significance of specific amino acid residues in dictating binding specificity and affinity and, through in silico modelling, we explored the potential structural basis for the observed carbohydrate binding properties. In doing so, we identified optimal amino acid substitutions that promote specific carbohydrate binding activities and produced an array of novel RPL's with diverse carbohydrate binding activities that will be of use for a broad spectrum of glycoselective applications.

STATEMENTS OF INVENTION

In a first embodiment, there is provided a peptide analogue of PA-IL of SEQ ID NO: 1, wherein the peptide analogue has altered carbohydrate binding specificity, and wherein the peptide analogue comprises an amino acid substitution at one, two or three of positions 50, 52 and 53, wherein the amino acid substitution at position 50 is selected from the group consisting of Ala, Val, Leu, Ile, Met, Phe, Trp, Pro, Ser, Thr, Cys, Tyr, Gly, Asn, Asp, Gln, Glu, Lys, and Arg; optionally from the group consisting of Ala, Val, Leu, Phe, Pro, Ser, Thr, Gly, Asn, Asp, Gln, Glu, Lys, and Arg; and further optionally from the group consisting of Ala, Val, Leu, Ser, Thr, Gly, Asn, Gln, Glu, Lys and Arg; wherein the amino acid substitution at position 52 is selected from the group consisting of Ser, Thr, Cys, Asn, Gln, Asp, Glu, Lys, Arg and His; optionally from the group consisting of Thr, Cys, Asn, Arg and His; and further optionally from the group consisting of Asn, Thr, Arg and His; and wherein the amino acid substitution at position 53 is selected from the group consisting of Ala, Val, Leu, Ile, Met, Phe, Trp, Pro, Gly, Ser, Thr, Cys, Tyr, Asn, Asp, Glu, Lys, Arg and His; optionally from the group consisting of Ala, Val, Leu, Gly, Ser, Tyr, Asn, Asp, Glu, Lys, Arg and His; and further optionally from the group consisting of Ala, Val, Leu, Gly, Ser, Asn, Asp, Glu, Lys, Arg and His.

Optionally, the peptide analogue has improved binding to a carbohydrate having a terminal β galactose, optionally a terminal β1,4-linked galactose, over PA-IL of SEQ ID NO: 1 and wherein the peptide analogue comprises an amino acid substitution at position 50 selected from Ala, Val, Leu, Ile, Met, Pro, Ser, Thr, Cys, Asn, Gln, Glu, Lys and Arg; optionally from the group consisting of Ala, Val, Leu, Pro, Ser, Thr, Asn, Gln, Glu, and Lys; and further optionally from the group consisting of Asn, Gln, Glu, and Val. Further optionally, the peptide analogue comprises Asn at position 50 and an amino acid substitution at position 53 selected from the group consisting of Ala, Val, Leu, Ile, Met, Gly, Ser, Thr, Asn, Asp, Glu, Lys, Arg and His; optionally from the group consisting of Ala, Val, Leu, Gly, Ser, Asn, Asp, Glu, Lys, Arg and His; and further optionally from the group consisting of Ala, Val, Gly, Ser, Lys, Arg and His. Alternatively, the peptide analogue comprises Asn at position 50 and Gly at position 53; the peptide analogue optionally comprising Gln, Asp, Glu or Asn at position 52; the peptide analogue further optionally comprising Asn at position 52. Further alternatively, the peptide analogue comprises Val at position 50 and an amino acid substitution at position 53 selected from the group consisting of Ala, Val, Leu, Ile, Met, Gly, Ser, Thr, Asn, Asp, Glu, Lys, Arg and His; optionally from the group consisting of Ala, Val, Leu, Gly, Ser, Asn, Asp, Glu, Lys, Arg and His; and further optionally from the group consisting of Ala, Val, Gly, Ser, Lys, Arg and His.

Optionally, the peptide analogue has altered carbohydrate binding specificity for a carbohydrate having a terminal α-linked galactose over PA-IL of SEQ ID NO: 1 and wherein the peptide analogue comprises an amino acid substitution at position 50 selected from Ala, Val, Leu, Ile, Met, Ser, Thr, Cys, Asn, Gln, Glu, Lys and Arg; optionally from the group consisting of Ala, Val, Leu, Ser, Thr, Asn, Gln, Glu, Lys and Arg; and further optionally from the group consisting of Val, Leu, Asn, Gln and Lys. Further optionally, the peptide analogue comprises Asn at position 50 and an amino acid substitution at position 53 selected from the group consisting of Ala, Val, Leu, Ile, Met, Gly, Ser, Thr, Cys, Asn, Asp, Glu, Arg, Lys and His; optionally from the group consisting of Ala, Val, Leu, Gly, Ser, Asn, Asp, Glu, Arg, Lys and His; and further optionally from the group consisting of Ala, Ser, Gly, Arg, Lys and His.

Optionally, the peptide analogue has enhanced carbohydrate binding specificity for a carbohydrate having a terminal α-linked galactose over PA-IL of SEQ ID NO: 1 and wherein the amino acid substitution at position 53 is selected from the group consisting of Asn, Asp, Glu, Arg and His; and optionally from the group consisting of Glu and Arg.

Optionally, the peptide analogue has altered carbohydrate binding specificity for a carbohydrate having a terminal α-linked galactose over PA-IL of SEQ ID NO: 1 and wherein the peptide analogue comprises Val at position 50 and an amino acid substitution at position 53 selected from the group consisting of Ala, Val, Leu, Ile, Met, Phe, Trp, Pro, Gly, Ser, Thr, Cys, Tyr, Asn, Asp, Glu, Lys, Arg and His; wherein optionally the peptide analogue comprises Val at position 50 and an amino acid substitution at position 53 selected from the group consisting of Ala, Val, Leu, Gly, Ser, Tyr, Asn, Asp, Glu, Lys, Arg and His and further optionally, the peptide analogue comprises Val at position 50 and an amino acid substitution at position 53 selected from the group consisting of Arg and Lys.

Optionally, the peptide analogue has altered carbohydrate binding specificity for a carbohydrate having a terminal α-linked galactose over PA-IL of SEQ ID NO: 1 and wherein the peptide analogue comprises Gln at position 50 and an amino acid substitution at position 53 selected from the group consisting of Ala, Val, Leu, Ile, Met, Phe, Trp, Pro, Gly, Ser, Thr, Cys, Tyr, Asn, Asp, Glu, Lys, Arg and His; wherein optionally the peptide analogue comprises Gln at position 50 and an amino acid substitution at position 53 selected from the group consisting of Ala, Val, Leu, Gly, Ser, Tyr, Asn, Asp, Glu, Lys, Arg and His and further optionally, the peptide analogue comprises Gln at position 50 and an amino acid substitution at position 53 selected from the group consisting of Arg and Lys.

Optionally, the peptide analogue has enhanced carbohydrate binding specificity for a carbohydrate having a terminal β- or a α-linked galactose over PA-IL of SEQ ID NO: 1 and wherein the peptide analogue comprises an amino acid substitution at position 50 selected from Asn, Leu and Gln.

Optionally, the peptide analogue comprises an amino acid substitution at position 50 selected from Ala, Val, Leu, Phe, Pro, Gly, Ser, Thr, Asn, Gln, Asp, Glu, Lys, and Arg.

Optionally, the peptide analogue comprises Asn at position 50 and an amino acid substitution at position 53 is selected from the group consisting of Ala, Val, Leu, Gly, Ser, Tyr, Asn, Asp, Glu, Lys, Arg and His.

Optionally, the peptide analogue comprises an amino acid substitution at position 53 selected from Glu, Lys and Arg.

Optionally, the peptide analogue comprises Val at position 50 and an amino acid substitution at position 53 selected from the group consisting of Ala, Val, Leu, Gly, Ser, Tyr, Asn, Asp, Glu, Lys, Arg and His.

Optionally, the peptide analogue comprises an amino acid substitution at position 52 selected from the group consisting His, Asn, Cys, Thr and Arg and, further optionally, an amino acid substitution at position 50 selected from the group consisting of Leu, Thr, Val, Asn, Gly and Pro and an amino acid substitution at position 53 selected from the group consisting of Arg, Glu, Ser, Gly, Leu and Asn.

Optionally, the carbohydrate, for which the peptide analogue of the present invention has altered carbohydrate binding specificity, is a carbohydrate or is selected from the group consisting of glycoprotein, glycoconjugate and cell surface. Further optionally, the glycoprotein, glycoconjugate and cell surface comprises an oligosaccharide or a polysaccharide linked to a protein or other conjugate.

In a second embodiment, there is provided a method for detecting changes in the glycosylation of a carbohydrate that is optionally selected from the group consisting of glycoprotein, glycoconjugate and cell surface, the method comprising qualitatively or quantitatively assessing terminal galactosylation using a peptide analogue of any aspect of the first embodiment. These methods find utility for detecting changes in the presence of, or exposure of, terminal α- and β-linked galactose, whether for purification or analytical work, or for diagnostic purposes.

In a third embodiment, there is provided a method of separating and isolating/purifying biomolecules/cells comprising a glycoprotein or glycoconjugate, the method comprising contacting the peptide analogue of any aspect of the first embodiment with a solution or suspension containing biomolecules/cells; separating any biomolecules/cells not bound by the peptide analogue and, optionally, subsequently recovering biomolecules/cells bound by the peptide analogue by disassociating them from the peptide analogue.

LEGENDS TO FIGURES

FIG. 1: Structure of the PA-IL Protein. (A) Tetrameric PA-IL protein with bound iGb3 trisaccharide Gal-α1,3-Gal-β1,3-Glc (PDB code 2VXJ) (23). Each monomer subunit (A, B, C, D) contains a single carbohydrate binding site. A single calcium ion is coordinated within each binding site (grey sphere) and is essential for sugar binding. (B) The PA-IL binding site showing coordination of the calcium ion and binding of iGb3. Amino acid residues Asp100, Thr104, Asn107, Asn108 of the calcium binding loop (residues 100-108), and Tyr36 of the neighbouring loop, are involved in calcium coordination and also form hydrogen bonds (interactions indicated by dash lines) with the non-reducing α-linked galactose. The non-reducing α-linked galactose also participates in coordination of the calcium contributing two interactions with the metal ion. Residues His50 and Gln53 form hydrogen bonds with the non-reducing αGal and Gln53 also interacts with the second galactose in the trisaccharide. Images were generated using Deep View (Swiss Model) (25) and rendered using CCP4MG software (26).

FIG. 2: Qualitative ELLA Screening of Random rPA-ILNm Proteins. Nine rPA-ILNm proteins, identified in initial library screens, were purified and re-assessed for their ability to bind to (A) transferrin and derived transferrin glycoforms and (B) fetuin and derived fetuin glycoforms. The data confirmed the ability of these rPA-ILNm proteins to bind to glycoprotein targets displaying LacNAc (asialotransferrin and asialofetuin) and that binding was dependent on the terminal β1,4-linked galactose (note the loss of signals on agalactotransferrin and agalactofetuin).

FIG. 3: Identification of Amino Acid Substitutions Present in Isolated rPA-ILNm Proteins. Sequence alignment of amino acid residues from Gln45 to His59 in PA-IL with the equivalent residues present in isolated rPA-ILNm proteins. Specific amino acid substitutions were observed to occur with high frequency. Substitutions occurring more than once at each of the positions corresponding to H50, D52 and Q53 in wild type native PA-IL protein are indicated in boxes.

FIG. 4: Lectin Dilution Response Curves against Defined BSA Glycoconjugates. (A) BSA-LacNAc: All of the rPA-ILNm proteins, with the exception of rPA-ILNmA8, displayed strong binding to BSA-LacNAc but the rPA-ILNmE6 exhibited the highest relative affinity to this glycoconjugate, with signal reaching saturation at lectin concentrations above 0.625 μg $mL^{-1}$. As expected, the parental rPA-ILN protein showed little binding to this glycoconjugate, even at relatively high lectin concentrations of 10 μg $L^{-1}$. (B) BSA-αGal: The parental rPA-ILN protein exhibited the strongest binding to the BSA-αGal glycoconjugate, with signals reaching saturation at lectin concentrations above 1.25 μg $mL^{-1}$. Four rPA-ILNm proteins were also observed to bind significantly to this glycoconjugate. The rPA-ILNmB10 and rPA-ILNmF3 proteins displayed similar response curves and a higher relative affinity for this glycoconjugate than rPA-ILNmB4. The rPA-ILNmE6 was also observed to bind comparatively weakly to BSA-αGal and signals did not reach saturation levels over the lectin concentration range examined. (C) Glycan Selectivity: indicated by plotting the ELLA response of each lectin to each glycoconjugate at a lectin concentration of 0.625 μg $mL^{-1}$. This clearly shows that the rPA-ILNmE6 protein exhibits significant preferential binding to BSA-LacNAc while rPA-ILNmF3 appears to exhibit a dual binding specificity for both glycoconjugates.

FIG. 5: Evaluation of rPA-ILNm Binding to Natural Glycoprotein Targets. Lectin dilution response curves were prepared against (A) asialotransferrin and (B) asialofetuin. Biotinylated ECL was included as a positive control in ELLA's. The rPA-ILNmE6 displayed the highest relative affinity to both glycoproteins with signals reaching saturation levels on both glycoproteins at lectin concentrations above 1 μg $mL^{-1}$. The rPA-ILNmC5, rPA-ILNmG3 and rPA-ILNmB4 exhibited strong binding to asialofetuin but displayed significantly reduced relative affinities to asialotransferrin. This indicated an overall lower relative affinity for LacNAc and a greater dependency on glycan display density than the rPA-ILNmE6 protein. ECL displayed a high relative affinity to both glycoprotein targets but responses on asialotransferrin indicate an overall lower relative affinity for this glycoprotein compared to rPA-ILNmE6.

FIG. 6: Determination of Affinity Constants for rPA-ILNm Proteins against BSA-LacNAc. Glycoconjugate dilution response curves were prepared and used to determine the $B_{max}$ and the affinity constant $K_D$ for each of the rPA-ILNm proteins according to the method described by Kirkeby et al 2002 (27). ECL was also included for comparative purposes. Both rPA-ILNmE6 and rPA-ILNmF3 displayed higher relative affinities for BSA-LacNAc than ECL as indicated by their lower calculated $K_D$ values. The rPA-ILNmE6 and rPA-ILNmF3 proteins generated $K_D$ values of 4 ng and 6.3 ng respectively while ECL generated a $K_D$ value of 21 ng. This indicates that the rPA-ILNmE6 has a five fold higher relative affinity for BSA-LacNAc than ECL while the rPA-ILNmF3 has approximately a 3 fold higher relative affinity.

FIG. 7: The Application of rPA-ILNmE6 for the Separation and Selective Purification of Glycoproteins and Glycoforms Displaying Terminal β1,4-Linked Galactose. (A) SDS-PAGE analysis of fractions obtained from lectin pull down assays performed using rPA-ILNmE6 Sepharose. Lane (1) 4 μg asialotransferrin; (2) 4 μg carbonic anhydrase; (3) 4 μg glucose oxidase; (4) 4 μg cytochrome C; (5) molecular weight ladder (NEB wide range protein ladder); (6) 20 μL of a protein mix containing 200 μg $mL^{-1}$ of each of the proteins shown in lanes 1 to 4; (7) 20 μL of unbound protein fraction and (8) 20 μL bound galactose eluted protein fraction. It can be clearly seen that the asialotransferrin was successfully isolated from the protein mixture by the rPA-ILNmE6 Sepharose resin. (B) Separation of glycoprotein glycoforms: a 2 mL sample comprised of a mixture of 1 mg of transferrin and 1 mg of asialotransferrin was applied to a 1 mL rPA-ILNmE6 Sepharose FPLC column. The sample was effectively separated into two fractions: one fraction comprised of unbound protein (U) and one comprised of bound protein (Bd) which was selectively eluted by inclusion of 0.5M galactose in the mobile phase. (C) ELLA analysis of FPLC fractionated transferrin glycoforms. Only the bound fraction elicited strong responses from the galactophilic lectins confirming effective separation and isolation of the asialotransferrin glycoforms.

FIG. 8: Expression Vectors Constructed for Expression of rPA-IL Proteins: Panels (A) and (B) show maps of the constructed pQE30PA-IL and pQE60PA-IL vectors respectively. Panels (C) and (D) show the coding regions of the pQE30PA-IL and pQE60PA-IL expression vectors. Important sequence elements highlighted: the ribosome binding site (RBS), start and stop codons (bold underlined); restriction sites (bold shaded); residues subjected to random mutagenesis (bold italics underlined). Sequences primed for mutagenesis are indicated by arrows; PA-ILmutF (dashed arrow) and PA-ILmutR (solid arrow). Panel (E) The amino acid sequences of rPA-ILN and rPA-ILC. The pQE30PA-IL vector expresses a mature rPA-ILN protein of 133 amino acids (excluding the initiator methionine) with an estimated molecular weight of 14.16 kDa, pI of 6.45 and extinction coefficient of 1.974. The pQE60PA-IL vector expresses a mature rPA-ILC protein of 129 amino acids (excluding the initiator methionine) with an estimated molecular weight of 13.83 kDa, a pI of 6.45 and extinction coefficient of 2.02. Residues targeted for mutagenesis are highlighted in bold underlined.

FIG. 9: SDS-PAGE Analysis of PA-IL Proteins: Panels (A) and (B) show SDS-PAGE analysis of samples from the expression and purification of rPA-ILC and rPA-ILN respectively. In each panel: Lane 1—molecular weight ladder (NEB Wide Range Protein Ladder—sizes are in kDa); Lane 2—soluble cell lysate (CL); Lane 3—final sample of flow through cell lysate (FT); Lane 4—final sample of 80 mM imidazole wash; Lane 5—eluted rPA-IL protein. The rPA-IL proteins (indicated by arrows) ran around 14 kDa as expected. High level expression of both of the rPA-IL proteins in the soluble cell lysate fraction can be clearly seen. Both proteins were effectively captured by IMAC resin resulting in no rPA-IL bands being visible in FT fractions or in high stringency 80 mM imidazole wash fractions. Both of the purified rPA-IL proteins exhibited a very high level of purity. (C) Comparison of purified rPA-IL proteins with commercial untagged PA-IL (PA-ILU). Lane 1—SDS-PAGE protein standards; Lane 2—PA-ILU; Lane 3—rPA-ILN; Lane 4—rPA-ILC. All proteins ran at their expected molecular weights with rPA-ILN and rPA-ILC running slightly larger (14.1 kDa and 13.8 kDa respectively) than PA-ILU (12.7 kDa).

FIG. 10: GPC Analysis of PA-ILU, rPA-ILC and rPA-ILN: GPC was conducted using a Superdex 75 10/300 GL column (GE Healthcare) which had a total volume ($V_t$) of 19 mL and a void volume ($V_o$) of 7.73 mL. Experiments were performed using an AKTA purifier and all samples were run in PBS and therefore under physiological conditions. Elution volumes ($V_e$) were experimentally determined for a series of molecular weight standards. This enabled the calculation of $K_{av}[(V_t-V_e)/(V_t-V_o)]$ values for each of the protein standards and the subsequent preparation of a plot of molecular weight (MW) versus $K_{av}$ which had an $R^2$ value of 0.997. This plot was used to calculate an estimated molecular weight ($MW_e$) for commercially obtained untagged PA-IL protein (PA-ILU) which is known to be a tetramer at physiological pH with a molecular weight of 51 kDa (23). The GPC estimated molecular weight of 41.5 kDa was significantly less than the expected 51 kDa. The discrepancy between the actual and the experimentally determined molecular weights for the PA-ILU protein is likely to be due to conformational differences between the PA-ILU protein and the globular proteins used as standards to generate the $K_{av}$ plot. The rPA-ILC protein had an estimated molecular weight of 40.3 kDa, which was similar to that of the PA-ILU protein, and it was therefore determined to be tetrameric. The rPA-ILN protein was estimated to have a molecular weight of 19.6 kDa, approximately half that of the rPA-ILC protein, and it was therefore proposed to be a dimer.

FIG. 11: Functional Analysis of the rPA-IL Proteins Using the Hemagglutination Assay. (A) Hemagglutination Assays: In each panel, well 1 is a negative control to which no lectin was added. For the PA-ILU and PA-ILC proteins, well 2 had a final lectin concentration of 25 μg $mL^{-1}$ while, for the rPA-ILN protein, the concentration was 50 μg $mL^{-1}$. Subsequent wells had serial 1:2 dilutions of the lectins. Both the PA-ILU and rPA-ILC showed similar hemagglutination profiles displaying full agglutination up to well 9 (195 ng $mL^{-1}$). The rPA-ILN showed a significantly decreased capacity to agglutinate RBC's with complete agglutination visible up to well 5 (6.25 μg $mL^{-1}$). For the PA-ILU and rPA-ILC proteins 1 HU was therefore calculated to be 195 ng $mL^{-1}$ while, for rPA-ILN, it is was calculated to be 6.25 μg $mL^{-1}$. (B) Hemagglutination Inhibition assays: Inhibitions were carried out with three carbohydrates; raffinose (Raf: Gal-α1,6-Glc-β1,2-Fru), melibiose (Mel: Gal-α1,6-Glc) and galactose (Gal) known to be bound by the PA-IL protein (28). In each panel: Lane 1—negative control with no lectin added; Lane 2—positive control containing 2HU of each lectin and no inhibiting carbohydrate. For raffinose and melibiose inhibitions, well 3 had a final carbohydrate concentration of 2.5 mM while, for galactose, it was 6.25 mM. Subsequent wells contained a serial 4:5 dilution series of the carbohydrate. Both the PA-ILU and rPA-ILC proteins showed similar inhibition profiles for all carbohydrates. For both raffinose and melibiose inhibitions, complete inhibition was scored to well 8 (0.82 mM). Galactose was less effective, with full inhibition being scored to well 7 (2.56 mM). The rPA-ILN protein was significantly more sensitive to inhibition with all carbohydrates tested. Melibiose and raffinose were found to completely inhibit in wells 16 (0.18 mM) while galactose was found to fully inhibit in well 19 (0.14 mM).

FIG. 12: Functional Analysis of rPA-IL Proteins by ELLA. (A) The rPA-ILC, rPA-ILN and GSL-I lectins were tested for their ability to bind a BSA-αGal glycoconjugate by ELLA. The glycoconjugate was immobilized at a concentration of 5 μg $mL^{-1}$ and each of the lectins was evaluated over a range of concentrations (5 μg $mL^{-1}$ to 50 ng $mL^{-1}$). Biotinylated GSL-I was detected using an anti-biotin antibody, while bound rPA-IL proteins were detected using an anti-HIS antibody. Of the two rPA-IL proteins, only binding of the rPA-ILN protein could be detected. As rPA-ILC had been demonstrated to be functional via other methods, the failure of this protein to generate signals in ELLA's was due to steric unavailability of the 6HIS tag to binding by the anti-HIS antibody.

FIG. 13: Qualitative ELLA analysis of rPA-ILNm proteins carrying His50 substitutions. The rPA-ILNm mutants are labelled with a single letter code indicative of the His50 substitution they carry. The rPA-ILN protein (WT) and certain of the rPA-ILNm proteins from Example A were included for comparative purposes: rPA-ILNmE6 (E6), rPA-ILNmC5 (C5), rPA-ILNmF3 (F3), rPA-ILNmB4 (B4). A number of plant lectins were also included as controls; ECL (β1,4-linked galactose), GSLI (α-linked galactose), RCA (galactophilic and tolerates capping α2,6 sialic acid), SNA (α2,6 sialic acid) and MALII (α2,3 sialic acid). These confirm the absence of capping sialic acid on asialotransferrin. Results clearly identify a number of His50 substitutions that alter the carbohydrate binding specificity and affinity compared to the rPA-ILN protein. Proteins displaying significant binding to the BSA-LacNAc and BSA-αGal glycoconjugates are indicated by black and white arrows respectively.

FIG. 14: Lectin dose response curves for selected His50 substituted rPA-ILNm proteins. (A) Response curves for selected lectins tested against BSA-LacNAc. Results clearly show the rPA-ILNmE6 (E6) exhibits the highest affinity but this is only slightly greater than that displayed by H50N (N) and H50E (E). H50V (V), H50Q (Q) and H50T (T) proteins displayed significantly and progressively weaker binding affinities to this glycoconjugate. (B) Response curves for selected lectins tested against BSA-αGal. Results clearly show that the H50Q protein exhibited the highest affinity for this glycoconjugate. Although this was greater than its affinity for the BSA-LacNAc glycoconjugate, it was still significantly weaker than that of the parental rPA-ILN protein (WT). The H50K (K) protein displayed a slightly lower affinity than that of the H50Q. The H50N protein also bound to the BSA-αGal glycoconjugate and, while lower than that of H50Q and H50K, it was significantly greater than that displayed by the rPA-ILNmE6 protein.

FIG. 15: Qualitative ELLA analysis of H50N proteins with additional Gln53 substitutions. The rPA-ILNm proteins tested are represented by a two letter code indicating the amino acid substitutions they carry e.g. NG has H50N and Q53G substitutions. The rPA-ILN protein (WT), rPA-IL- Nme6 (E6) and H50N (N) were included for comparative analysis. Results show that substitution of the Gln53 residue with a range of different amino acids only resulted in subtle differences in binding activities towards the two BSA glycoconjugates and the asialotransferrin (AsT). None of the new H50N:Q53 double mutants bound to the BSA-LacNAc or asialotransferrin better than the H50N. Interestingly, the NG protein generated weaker signals on asialotransferrin than the H50N and significantly weaker than those generated by the rPA-ILNmE6 protein. The H50N:Q53E protein exhibited strong signals on the BSA-αGal glycoconjugate which were comparable to, if not slightly stronger than, those of the parental H50N protein but significantly lower than those obtained for the rPA-ILN protein. However unlike the H50N protein it exhibited negligible binding towards asialotransferrin.

FIG. 16: The role of a Q53R substitution in promoting binding to α-linked galactose: (A) Qualitative ELLA screen of selected rPA-ILNm proteins carrying Q53R, Q53K or Q53E substitutions. The rPA-ILN protein (WT), rPA-ILNmE6 (E6) and rPA-ILNmF3 proteins were included for comparative analysis. The rPA-ILNm proteins tested are represented by a two letter code indicating the amino acid substitutions they carry in place of His50 and Gln53 respectively. Results clearly show that introduction of a Q53R substitution into H50V and H50Q (generating VR, and QR respectively) resulted in a slight increase in signals against BSA-αGal proteins. The H50V:Q53R protein also displayed increased binding to terminal β1,4 linked galactose compared to the H50V protein which was in contrast to the H50Q:Q53R protein which exhibited a significant reduction in binding to β1,4 linked galactose compared to the H50Q protein. When a single Q53R substitution was introduced into the parental rPA-ILN protein it again resulted in enhanced binding to BSA-αGal and this was also observed for a conservative Q53E substitution (HR and HE proteins respectively). (B) Lectin dose response curves for selected rPA-ILN proteins with Q53R or Q53E substitutions. Also included are the rPA-ILN (WT), rPA-ILNmF3 (F3) and H50Q proteins for comparative purposes. It can be seen that rPA-ILNm proteins carrying either a single Q53E (HE) or Q53R (HR) substitution exhibited higher relative binding affinities for the BSA-αGal glycoconjugate than the parental wild type rPA-ILN protein. The H50Q:Q53R (QR) protein also exhibited a higher affinity than its parental H50Q (Q) protein. While a parental H50V protein was not observed to bind significantly to the BSA-αGal glycoconjugate, it can be seen that the H50V:Q53R protein exhibited an affinity for the glycoconjugate comparable to that of the rPA-ILNmF3 protein.

FIG. 17: Structural models depicting the probable steric role played by the amino acid at position 50 in determining the linkage specificity of PA-IL proteins. (A) PA-IL in complex with iGb3. (B) PA-IL with lactose modelled into the binding pocket such that the terminal galactose moiety is bound in the configuration observed in crystal structures obtained to date with either bound D-galactose (29) or iGb3 (23). This illustrates that binding of the terminal galactose of a lactose molecule in this configuration would result in the glucose moiety sterically clashing with the His50 residue. (C, D & E). Models showing the possible effects of H50N, H50V and H50Q mutations, respectively, on the conformation of the PA-IL binding site. ELLA analysis demonstrated that replacing His50 with these amino acid residues promoted binding of glycans with terminal β1,4-linked galactose. Models suggest this is partly the result of a more open conformation in the binding pocket thereby allowing glycans with β-linked galactose to enter.

FIG. 18: Structural models of rPA-ILNm lectins with defined His50 substitutions and bound lactose (Gal-β1,4-Glc). (A) H50N: Hydrogen bonds between the Asn50 side chain and both sugar residues may occur. The side chain of Tyr36 may also form a hydrogen bond, with the galactose moiety to stabilize binding to β-linked galactose in each of the H50 mutants. (B) H50V: Val50 cannot form hydrogen bonds with the sugar, although it may form some stabilizing hydrophobic contacts with the glucose moiety. (C) H50Q: It is difficult to predict if a glutamine residue will make contacts with a bound sugar as the side chain may adopt several orientations. However, ELLA results show that this protein is capable of binding strongly to BSA-LacNAc, and the side chain orientation depicted shows that it may enable hydrogen bonding with the substrate. (D) Random mutant rPA-ILNmE6. The Q53G substitution would potentially result in the loss of the hydrogen bond between Gln53 and the terminal galactose sugar moiety.

FIG. 19: Structural models of rPA-ILNm mutants with iGb3 (Gal-α1,3-Gal-β1,4-Glc). (A) H50N, (B) H50V, (C) H50Q and (D) rPA-ILNmE6. The H50Q substitution showed the highest affinity of all of the His50 mutants for BSA-αGal in ELLA's. This is potentially due to the formation of an additional hydrogen bond with the second galactose in the oligosaccharide chain. An Asn50 side chain, also found in rPA-ILNmE6, can possibly interact with the terminal galactose, while Val50, which shows the lowest binding to BSA-αGal, does not make positive contacts with the sugar.

FIG. 20: Amino Acid Sequences of the rPA-ILN Protein and Derived Mutants (rPA-ILNm). Residues incorporated at the N-terminus (the 6HIS affinity purification tag and additional amino acid residues) are boxed. The natural initiator methionine of the PA-IL protein is indicated in black bold. Residues randomly substituted in mutants are bold and underlined. Please note:

a. These correspond to residues His62, Aps64 and Gln65 in the rPA-ILN protein excluding its initiator methionine; or
b. These correspond to residues His50, Asp52 and Gln53 in the wild type PA-IL protein excluding its initiator methionine.

The abbreviations used are: PA-IL, *Pseudomonas aeruginosa* lectin 1; rPA-IL, recombinant PA-IL; ELLA, enzyme linked lectin assay; iGb3, isoglobotriaosylceramide (Gal-α1,3-Gal-β1,4-Glc); PBS, Phosphate Buffered Saline; TBS, Tris Buffered Saline; TBST, Tris Buffered Saline with Tween 20; IPTG, Isopropyl-β-D-thiogalactopyranoside.

The glycoconjugate used as a representative of glycoproteins displaying glycans with terminal β-linked galactose was BSA-LacNAc (Gal-β1,4-GlcNAc-BSA). Lectins representative of those showing binding to a terminal β-linked galactose include ECL (*Erythrina cristagalli* Lectin) and RCA (*Ricinus communis* Agglutinin).

The glycoconjugate used as a representative of glycoproteins displaying glycans with terminal α-linked galactose was BSA-αGal (Gal-α1,3-Gal-BSA). The lectin used as a representative of those showing binding to a terminal α-linked galactose was GSLI (*Griffonia simplicifolia* isolectin B4).

EXAMPLE A

Experimental Procedures

Plasmid Construction—pQE30PA-IL & pQE60PA-IL—

All strains and plasmids used or constructed as part of this study are listed and described in Table A1 set out below. The lecA gene encoding the PA-IL protein was amplified from *Pseudomonas aeruginosa* PAO1 (This strain can be obtained from a wide variety of sources including many cell culture banks) genomic DNA by PCR to facilitate cloning into the pQE series of *E. coli* expression vectors from Qiagen. PCR reactions were carried out using high fidelity Phusion Taq and PCR conditions recommended by the manufacturer (New England BioLabs). The lecA gene was amplified using the PA-IL-F1 and PA-IL-R1 primers (Table A2 below) to generate a product that could be cloned as a BamHI-HindIII fragment into the pQE30 expression vector. The resulting plasmid, pQE30PA-IL (FIG. 8A), expressed an rPA-IL protein with an amino (N-) terminal 6HIS tag (rPA-ILN). The lecA gene was also amplified using the PA-IL-F2 and PA-IL-R2 primers to enable cloning as an NcoI-BglII fragment into the pQE60 vector (Qiagen). The resulting plasmid, pQE60PA-IL (FIG. 8B), expressed an rPA-IL protein with a carboxy (C-) terminal 6HIS tag (rPA-ILC).

TABLE A1

Strains and Plasmids used in Example A.

| Strains | Genotype | Description | Source |
|---|---|---|---|
| | *Escherichia coli* | | |
| JM109 | F'traD36, proAB+ lacI$^q$, ΔlacZ M15, endA1, recA1, hsdR17($r_k$−, $m_k$+), mcrA, supE44, λ-gyrA96, relA1 Δ(lacproAB), thi-1. | All purpose cloning strain, produces stable plasmid DNA. | Promega |
| KRX | [F', traD36, ΔompP, proA+B+, lacI$^q$, Δ(lacZ)M15] ΔompT, endA1, recA1, gyrA96 (Nalr), thi-1, hsdR17 ($r_k$−, $m_k$+), relA1, supE44, Δ(lac-proAB), Δ(rhaBAD)::T7 RNA polymerase. | Protease deficient protein expression host. | Promega (30) |
| | *Pseudomonas aeruginosa* | | |
| PAO1 | Wild Type | | Dr. Keith Poole |

| Plasmids | Features | Description | Source |
|---|---|---|---|
| pQE30 | T5 promoter/lac operator element, rrnB T1 transcriptional termination region, ColE1 origin, β-lactamase gene. | Expresses proteins with an N-terminal RGS-6HIS affinity tag. | Qiagen |
| pQE60 | T5 promoter/lac operator element, rrnB T1 transcriptional termination region, ColE1 origin, β-lactamase gene. | Expresses proteins with a C-terminal 6HIS affinity tag. | Qiagen |
| pQE30PA-IL | pQE30 with cloned *P. aeruginosa* lecA | Expresses rPA-ILN: Wild type PA-IL with an N-terminal RGS-6HIS affinity tag. | Example A |
| PQE60PA-IL | pQE60 with cloned *P. aeruginosa* lecA | Expresses rPA-ILC: Wild type PA-IL with a C-terminal 6HIS affinity tag. | Example A |

| Mutagenized Plasmids | Amino Acid Substitutions | | | Protein Expressed | Source |
|---|---|---|---|---|---|
| pPC30PA-IL-A8 | H50L | D52H | Q53R | rPA-ILNmA8 | Example A |
| pPC30PA-IL-B4 | H50T | D52N | Q53R | rPA-ILNmB4 | Example A |
| pPC30PA-IL-B10 | H50V | D52C | Q53E | rPA-ILNmB10 | Example A |
| pPC30PA-IL-C5 | H50N | D52T | Q53S | rPA-ILNmC5 | Example A |
| pPC30PA-IL-E6 | H50N | D52N | Q53G | rPA-ILNmE6 | Example A |
| pPC30PA-IL-E12 | H50G | D52C | Q53R | rPA-ILNmE12 | Example A |
| pPC30PA-IL-F3 | H50V | D52C | Q53R | rPA-ILNmF3 | Example A |
| pPC30PA-IL-F6 | H50P | D52R | Q53L | rPA-ILNmF6 | Example A |
| pPC30PA-IL-G3 | H50V | D52N | Q53N | rPA-ILNmG3 | Example A |

TABLE A2

Primer Sequences used in Example A

Primers Used for Amplification and Cloning of the *lecA* Gene into pOE Expression Vectors Forward Primers PA-IL-F1 AaaaGGATCCatggcttggaaaggtgagg - SEQ ID NO. 42

PA-IL-F2 aaaaCCATGGcttggaaaggtgaggttctgg - SEQ ID NO. 43

Reverse Primer

PA-IL-R1 aaaaAAGCTTtcacgactgatcctttccaatatt - SEQ ID NO. 44

PA-IL-R2 aaaaAGATCTcgactgatcctttccaatattgacac - SEQ ID NO. 45

TABLE A2-continued

| Primer Sequences used in Example A | |
|---|---|
| Primers Used for Site Specific Mutagenesis of the *lecA* Gene. | |
| Forward Primer | |
| PA-ILmutF | cgttttgtggtgcgctggtcatgaagattggc - SEQ ID NO. 46 |
| Reverse Primer Used for Random Mutagenesis of H50, D52 and Q53 | |
| PA-ILmutR | cgtcgtggcagatcagccc**NNNNNN**cgg**NNN**ctcccgatcgccctg - SEQ ID NO. 47 |

Protein Expression and Purification—

For protein expression plasmids were transformed into the protease deficient *E. coli* strain KRX (30). Expression clones were cultured at 30° C. in Terrific Broth (TB) broth and protein expression induced by addition of IPTG to a final concentration of 50 μM. Cells were harvested by centrifugation and cell pellets resuspended in lysis buffer [10 mM $NaH_2PO_4$, 300 mM NaCl, 40 mM imidazole, pH 8.0). Cell disruption was achieved by high pressure using a Constant Systems™ cell disrupter and cell debris was removed by centrifugation. Clarified cell lysates were applied to 10 mL IMAC™ columns (IMAC Hypercel from Pal) and a high stringency wash buffer with 100 mM imidazole was used to remove non-specifically bound contaminating proteins. The desired 6HIS tagged proteins were ultimately eluted using 250 mM imidazole and eluted proteins were aliquoted and stored at −80° C. in the elution buffer. Typical yields were around 200 mg per 250 mL starting culture. Purified proteins were analysed by SDS-PAGE to assess purity (FIG. 9) and routinely buffer exchanged and concentrated using Vivaspin™ centrifugal membrane devices (Sartorius-Stedim), with a molecular weight cut off of 10 kDa, according to the manufacturer's guidelines.

Gel Permeation Chromatography (GPC)—

The estimated molecular weights of the rPA-IL proteins were determined by GPC, which was performed on a Superdex™ 75 10/300 GL column (GE Healthcare) using an AKTA Purifier 100 FPLC system. The molecular weight of commercially obtained untagged PA-IL (Sigma Aldrich) was also experimentally determined and used for comparison with 6HIS tagged rPA-IL proteins to enable determination of their quaternary structure (FIG. 10).

Hemagglutination Assays—

The hemagglutination assay is widely used to study lectin activity and is dependent on the multi-valency typically displayed by lectins. The assay was essentially performed according to the method described by Garber et al (31). The assay was performed using Papain treated Rat red blood cells (RBC's), obtained from the Bioresource unit at DCU such that the final concentration of cells in reaction wells was 3.5% w/v. Lectins to be tested were prepared in TBS (20 mM Tris, 150 mM NaCl, 1 mM $CaCl_2$, 1 mM $MnCl_2$, 1 mM $MgCl_2$, pH 7.6). Hemagglutination was observed, after 1 hour incubation at 25° C., as a thin film of cells coating the bottom of wells in U-bottomed 96 well plates compared to a concentrated spot of sedimented cells observed in negative controls to which no lectin was added (FIG. 11A). One hemagglutination unit (HU) was defined as the minimum quantity of lectin required to fully agglutinate the RBC solution. Sugar inhibition assays were performed such that the final lectin concentration in reaction wells was equivalent to 2 HU (FIG. 11B).

General Enzyme Linked Lectin Assay (ELLA) Method—

The Gal-α1,3-Gal-BSA (BSA-αGal) and Gal-β1,4-GlcNAc-BSA (BSA-LacNAc) glycoconjugates used were from Dextra Laboratories. Biotinylated plant lectins GSLI (*Griffonia simplicifolia* isolectin B4), ECL (*Erythrina cristagalli* Lectin), RCA (*Ricinus communis* Agglutinin), SNA (*Sambucus nigra* Agglutinin), MALII (*Maackia amurensis* Lectin) and LCA (*Lens culinaris* Agglutinin) were from Vector Laboratories. The glycoproteins fetuin, asialofetuin and invertase were from Sigma Aldrich while asialotransferrin, agalactotransferrin and agalactofetuin were generated by treatment using glycosidases, neuraminidase (*Clostridium perfingens*) and β1,4-galactosidase (*Bacteroides fragilis*), in accordance with manufacturer's guidelines (New England Biolabs). ELLA's were essentially performed according to the method described by Thompson et al (2011) (33). More specifically, glycoproteins were prepared in PBS and typically immobilized at a concentration of 5 μg $mL^{-1}$. For qualitative ELLA's, lectins were assayed at a concentration of 10 μg $mL^{-1}$ in TBST (20 mM Tris, 150 mM NaCl, 0.05% Tween-20, 1 mM $CaCl_2$, 1 mM $MnCl_2$, 1 mM $MgCl_2$, pH 7.6). For lectin dose response experiments, each lectin was evaluated at a range of concentrations prepared by serial 1:2 dilution of an initial lectin solution of 10 μg $mL^{-1}$ to a final concentration of 156 ng $mL^{-1}$. Binding of 6HIS tagged rPA-IL proteins was detected after 1 hour incubation at 25° C. using a HRP conjugated anti-HIS antibody diluted 1:10,000 in TBST (Sigma Aldrich). Biotinylated plant lectins were detected using a HRP conjugated anti-biotin antibody diluted 1:10,000 in TBST (Sigma Aldrich).

Lectin Affinity Constant Determination by ELLA—

Affinity constants were determined according to the method described by Kirkeby et al 2002 (27). ELLA's were performed using a constant concentration of 2 μg $mL^{-1}$ for the rPA-ILNm proteins and 4 μg $mL^{-1}$ of ECL to ensure all lectins were evaluated at equimolar concentrations. Each lectin was evaluated against BSA-LacNAc glycoconjugate immobilized at a range of concentrations from 10 μg $mL^{-1}$ to 19.5 ng $mL^{-1}$ (prepared by serial 1:2 dilution of a 10 μg $mL^{-1}$ stock). The resulting glycoconjugate dose response curve obtained enabled the calculation of $B_{max}$ and the affinity constant $K_D$ for each lectin against BSA-LacNAc. $B_{max}$ is defined as being the maximum plateau value of absorption and represents the maximum number of lectin binding sites expressed in the units of the Y-axis (AU). $K_D$ is defined as being the glycoconjugate concentration required to fill half of the available lectin binding sites at equilibrium. $K_D$ is therefore the glycoconjugate concentration that generates a signal equivalent to half $B_{max}$ and the unit for $K_D$ is nanograms of glycoconjugate. These values are specific for the defined experimental conditions used.

Site Directed Random Mutagenesis of the rPA-ILN Protein—

PCR based site directed mutagenesis of the lecA gene was achieved through whole vector amplification in which the pPC30PA-IL vector was used as the parental template DNA. Whole vector amplification was achieved using the primers PA-ILmutF and PA-ILmutR (Table A2 above). These primers were 5' phosphorylated and designed to anneal within the lecA sequence with their 5' ends exactly next to each other.

The reverse primers were designed to overlap the region to be mutagenized enabling the introduction of mutations through manipulation of reverse primer sequences (FIG. 8C). Successful PCR reactions were purified and subjected to digestion with the restriction enzyme DpnI to selectively digest the parental template vector DNA. Digestions were ultimately run on agarose gels and PCR products corresponding to the expected size of linear vector were gel extracted. The final purified PCR products, with blunt phosphorylated ends, were re-circularised by simple self ligation and the ligated DNA transformed into *E. coli* strain KRX. Transformants were picked into sterile deep well (2 mL) 96 well plates to generate master arrays of clones capable of expressing mutated rPA-ILN proteins (rPA-ILNm). Master plates were used to inoculate fresh 96 well plates containing 600 μL of LB media supplemented with ampicillin (100 μg $mL^{-1}$) and IPTG (50 μM) to induce expression of rPA-ILNm proteins. After overnight incubation at 30° C. cells were harvested by centrifugation and subsequently disrupted chemically by resuspending cell pellets in 1× Cell Lytic B solution (Sigma Aldrich) by repeated gentle pipetting. Plates were then incubated at room temperature for 1 hour or overnight at 4° C. to allow disruption of cells. Cell debris was removed by centrifugation and cell lysates were diluted 10 fold using TBST prior to being used in ELLA screens.

Fabrication of Lectin Affinity Resins— lectin affinity resins were prepared by immobilization onto cyanogen bromide (CNBr) activated Sepharose 4B prepared according to the manufactures guidelines (GE Healthcare). Lectin to be immobilized was buffer exchanged into coupling buffer (20 mM $NaH_2PO_4$, 500 mM NaCl, pH 8.5) and the lectin solution mixed with the CNBr Sepharose at a concentration of approximately 30 mg mL of resin. This mixture was then left mixing by inversion overnight at 4° C. Unbound protein was then decanted and un-reacted CNBr groups on the resin were capped with 1 M ethanolamine in coupling buffer and pH 8.5. This was left mixing by inversion at room temperature for 4 hours. Finally non-specifically bound protein was removed by 4 successive washes with coupling buffer and acetate buffer (100 mM NaOAc, 500 mM NaCl, pH 4.0). Resins were ultimately washed with TBS and for long term storage sodium azide was added to a final concentration of 2 mM.

Evaluation of Lectin Affinity Resins— lectin affinity resins were evaluated by performing small scale pull down assays in 1.5 mL eppendorf tubes or by packing into 1 mL FPLC cartridges (FliQ Column Housings, Generon) to enable easy connection to FPLC systems. For pull down assays, 50 μL of lectin affinity resin was mixed with 100 μL of a test protein mixture and mixed by inversion for 1 hour. Unbound protein was then removed using a pipette and the resin washed with three 1 mL aliquots of TBST. Bound protein was eluted by addition of 100 μL of TBST with 0.5 M galactose followed by incubation for 1 hour. Lectin affinity FPLC columns were connected to an AKTA Purifier 100 FPLC system. Columns were equilibrated using TBS and typically run at a flow rate of 0.5 mL per minute. Samples were prepared in TBS and 2 mL sample volumes were injected onto the 1 mL lectin affinity columns. Bound glycoproteins were eluted using 0.5M galactose prepared in TBS.

Results

Production of Affinity Tagged Recombinant PA-IL (rPA-IL)—

Commercially available untagged PA-IL (PA-ILU) is typically purified by exploiting its natural affinity for Sepharose 4B (23,34) but alteration of the protein's carbohydrate binding specificity could prevent purification in this manner. One of the first steps required for this study was, therefore, the incorporation of an affinity tag that would enable simple and rapid purification of recombinant PA-IL (rPA-IL) proteins independently of glycan binding specificity. The lecA gene, encoding the wild type PA-IL protein, was therefore cloned into two *E. coli* plasmid expression vectors to enable expression of rPA-IL with either an N-terminal (rPA-ILN) or C-terminal (rPA-ILC) polyhistidine (6HIS) tag and thereby enabling purification by IMAC. Both proteins were expressed to relatively high levels in the soluble cytoplasmic fraction of *E. coli* KRX, from which they were subsequently purified by IMAC. Assessment of the proteins by SDS-PAGE verified that both exhibited very high levels of purity (FIG. 9) and yields were typically around 800 mg $L^{-1}$ of culture.

Structural and Functional Assessment of Poly-Histidine Tagged rPA-IL Proteins—

Incorporation of a poly-histidine tag into any protein can have an impact on the structure, activity and other physiochemical properties (solubility, stability) of the protein. We therefore assessed the impact of the incorporated 6HIS tags on the quaternary structure and functionality of the rPA-IL proteins. Gel permeation chromatography (GPC) was used to experimentally determine the molecular weight of commercially obtained untagged PA-IL (PA-ILU), which is known to be a tetramer of four identical subunits under physiological conditions (FIG. 1) (23,29). This was used as a reference for comparison with the rPA-IL proteins to determine their quaternary structure. The rPA-ILC protein was determined to be a tetramer, like the PA-ILU protein, but the rPA-ILN protein was determined to exist as a dimer, indicating that the incorporation of the 6HIS affinity tag at the N-terminus of the protein had disrupted the quaternary structure of the protein to some extent (FIG. 10). The functionality of the rPA-IL proteins was assessed and compared to that of the PA-ILU protein using the hemagglutination assay. The rPA-ILC protein was found to have comparable activity to PA-ILU in hemagglutination assays with both proteins fully agglutinating Papain treated rat red blood cells (RBC's) at a lectin concentration of 195 ng $mL^{-1}$ (FIG. 11A). Both proteins also showed comparable inhibition profiles for all sugars assessed in sugar inhibition assays (FIG. 11B). The rPA-ILN protein was significantly less effective at agglutinating RBC's, requiring a concentration of 6.25 μg $mL^{-1}$ to produce full agglutination. This was also more readily inhibited by all of the sugars evaluated in sugar inhibition assays. Hemagglutination assays confirmed that both of the rPA-IL proteins were functional and that differences in their comparative performance reflected the differences in their respective quaternary structures where the rPA-ILN protein only has half the valency of the rPA-ILC protein. The ability of the rPA-ILN protein to agglutinate RBC's also provided evidence that the quaternary structure of the rPA-ILN protein was likely to be that of a dimer with an A-D subunit configuration (FIG. 1) because a dimer with an A-B subunit configuration would be unlikely to be capable of cross linking cell surfaces.

Selection of a Target rPA-IL Molecule for Mutagenesis Studies—

The steric accessibility of the 6HIS tags within the quaternary structures of the rPA-IL proteins was assessed by ELLA. Both of the rPA-IL proteins were tested for their ability to bind an immobilized BSA-αGal glycoconjugate with subsequent detection of the bound lectins using an anti-HIS antibody (33). Biotinylated GSL-I, a plant lectin with a binding specificity for terminal α-galactose (27,35), was included in the assays as a positive control. Binding of both rPA-ILN and GSLI could be detected in ELLA's with high sensitivity but binding of the rPA-ILC could not be detected using an anti- HIS antibody, even at relatively high lectin concentrations of 10 μg $mL^{-1}$ (not shown in FIG. 12A). As the functionality of both of the rPA-IL proteins had already been confirmed, this was therefore due to steric unavailability of the 6HIS tags within the rPA-ILC tetramer to binding by the anti-HIS antibody. This was further confirmed by direct immobilization of the rPA-ILC protein in ELISA plates and probing with anti-HIS antibody which failed to generate signals (data not shown). While incorporation of a 6HIS tag at the N-terminus of the rPA-IL was shown to disrupt the natural tetrameric structure of the PA-IL protein, the resulting dimeric molecules were demonstrated to be functional and could be readily detected, with high sensitivity, in ELLA's using an anti-HIS antibody. The pQE30PA-IL vector was therefore selected as the target DNA molecule for mutagenesis because the production of mutagenized rPA-IL proteins with N-terminally positioned 6HIS tags (rPA-ILNm) would not only facilitate their simple purification but also enable analysis of their carbohydrate binding activities through the use of ELLA assays without the need for any prior in vitro labelling steps. As all of the mutagenized proteins would ultimately be compared to the parental rPA-ILN protein, and would therefore have equivalent quaternary structures, comparative analysis could be performed by ELLA to identify proteins with altered carbohydrate binding properties.

Random Mutagenesis of the rPA-ILN Protein—

Residues from three separate parts of the PA-IL monomer are involved in coordinating calcium and binding of the iGb3 trisaccharide Gal-α1,3-Gal-β1,3-Glc (23) (FIG. 1). Amino acid residues involved in the coordination of the essential calcium ion were not selected for mutagenesis since alteration of these residues would likely result in loss of calcium coordination and consequently result in loss of carbohydrate binding. As residues His50 and Gln53 are only involved in making contacts with the carbohydrate, these residues were selected as target amino acid residues for mutagenesis. The intervening Pro51 and Asp52 residues were not thought to be directly involved in carbohydrate binding but modification of these residues could alter the spatial arrangement of the His50 and Gln53 residues relative to each other in the binding site and consequently impact carbohydrate binding. Proline residues introduce kinks and rigidity into polypeptide strands. Alteration of this residue might therefore be expected to result in dramatic structural changes in the carbohydrate binding site to negatively impact carbohydrate binding and so this residue was not selected for mutagenesis. However, substitution of the Asp52 residue might have more subtle affects and so this residue was selected for inclusion in the mutagenesis study.

The pQE30PA-IL plasmid was mutagenized using a PCR based method that resulted in the introduction of random simultaneous substitutions at positions corresponding to residues His50, Asp52 and Gln53 in the wild type native PA-IL protein. An array of mutant clones, containing 154 individual mutants, was prepared and cell lysates from these clones were analysed by ELLA. A number of different glycoproteins were used as immobilized targets in ELLA screens to identify clones expressing mutated rPA-ILN proteins (rPA-ILNm) exhibiting altered binding specificities compared to the parental rPA-ILN protein. Glycoproteins tested included fetuin (3 N-linked and 3 O-linked glycan structures highly sialylated with terminal α2,3 and α2,6-Neu5Ac) (36), asialofetuin (terminal LacNAc and terminal β1,3-Gal) and invertase (high mannose structures) (37). PA-IL is known not to bind strongly to these glycoprotein targets (28) and so any rPA-ILNm proteins identified as generating altered responses to these targets were considered to have altered carbohydrate binding properties. Of the 154 clones screened, none of the rPA-ILNm proteins displayed binding to invertase or significant binding to fetuin but a number of rPA-ILNm proteins were observed to exhibit altered binding to asialofetuin (data not shown). Nine of the rPA-ILNm proteins that exhibited the highest signals against these glycoproteins in the ELLA screen were selected and recovered from the array for further analysis. The selected rPA-ILNm proteins were named according to the well from which they were recovered in the original mutant array (i.e. rPA-ILNmE6 was recovered from row E and column 6).

The initial ELLA mutant library screen had been performed using soluble fractions of cell lysates and therefore differences observed in ELLA responses may have been impacted by differences in the expression levels of specific rPA-ILNm proteins or differences in the overall concentrations of cell lysates. To validate the results of the initial ELLA screen, the selected rPA-ILNm proteins were first purified by IMAC and then re-evaluated in qualitative ELLA's against an expanded set of glycoproteins and specifically generated glycoprotein glycoforms (FIG. 2). Transferrin is a commercially available glycoprotein that has two N-linked biantennary complex glycans (36). While none of the rPA-ILNm proteins were detected binding to transferrin, they were all found to bind to asialotransferrin (FIG. 2A). This demonstrated that, unlike the parental rPA-ILN protein, the selected rPA-ILNm proteins exhibited specificity for LacNAc, which displays terminal β1,4-linked galactose, exposed on the antenna of N-linked glycans as a result of the removal of terminal sialic acid. Removal of the terminal β1,4-linked galactose through treatment with β1,4-galactosidase, generating agalactotransferrin, eliminated binding of the rPA-ILNm proteins (FIG. 2A). This confirmed that binding was dependent on the terminal β1,4-linked galactose. A similar response pattern was observed for fetuin, asialofetuin and agalactofetuin glycoforms (FIG. 2B). The residual signals observed against agalactofetuin, generated by treatment of asialofetuin with β1,4-galactosidase, could have been due to binding to terminal β1,3-linked galactose displayed by de-sialylated O-linked Thomsen-Friedenreich (T) antigen structures on this glycoprotein (36). However, the plant lectin ECL was also found to generate residual signals against agalactofetuin. This lectin is known to be specific for terminal β1,4-linked galactose and does not bind significantly to terminal β1,3-linked galactose (38). This suggested incomplete removal of terminal β1,4-linked galactose was the likely source of the residual binding signals.

Identification of Amino Acid Substitutions in Selected rPA-ILNm Proteins—

Plasmid DNA from each of the rPA-ILNm expressing clones was isolated and sequenced to determine the nature of the amino substitutions present in each protein (FIG. 3). It can be clearly seen that the functional ELLA screening process resulted in the identification of a collection of rPA-ILNm proteins in which specific amino acid substitutions occurred with high frequency at each of the mutagenized positions. Of the nine rPA-ILNm proteins isolated, three were found to have a H50V substitution and two had a H50N substitution. Examining the Asp52 position, it can be seen that three rPA-ILNm proteins were found to have a D52C substitution while another three had a D52N substitution. Also, arginine was found to be substituted for Gln53 in four rPA-ILNm proteins. We undertook more detailed analysis of this collection of rPA-ILNm proteins to ascertain the potential significance of these amino acid substitutions Lectin Dose Response Curves Against Defined Glycoconjugate Targets—

The specificity of the selected rPA-ILNm proteins was further assessed by generating lectin dose response curves against two specific glycoconjugate targets; BSA-LacNAc and BSA-αGal (FIGS. 4A & B). These glycoconjugates enable detection of potentially weak interactions (39), due to multivalent and high density display of glycans, and assessment of the impact of substitutions on carbohydrate binding selectivity i.e. binding to glycans with terminal α-linked versus β-linked galactose (FIG. 4C). As all of the lectins molecules to be assessed had an equivalent quaternary structure, these lectin dose response curves enabled comparative analysis of the relative affinities of each of the rPA-ILNm lectins for each of the glycoconjugates.

The parental rPA-ILN protein only showed very weak binding to the BSA-LacNAc glycoconjugate, even at relatively high lectin concentrations of 10 μg $mL^{-1}$ (not shown in FIG. 4A). This was expected since the PA-IL protein is known not to bind significantly to glycans with terminal β1,4-linked galactose (23,28). Conversely, all of the rPA-ILNm proteins, with the exception of the rPA-ILNmA8, displayed strong binding to the BSA-LacNAc glycoconjugate. Of particular note was the rPA-ILNmE6 protein, which displayed a very high relative affinity to BSA-LacNAc, indicated by a very rapid increase in signal strength with increasing lectin concentration, and signals ultimately reached saturation at a lectin concentration of 0.625 μg $mL^{-1}$. The rPA-ILNmB10 and rPA-ILNmF3 proteins also showed a high relative affinity for the BSA-LacNAc followed by rPA-ILNmC5>G3-F6>B4. The parental rPA-ILN protein was observed to bind to the BSA-αGal glycoconjugate with a higher relative affinity than any of the rPA-ILNm proteins (FIG. 4B). However, four of the rPA-ILNm proteins also displayed a capacity to bind strongly to the BSA-αGal glycoconjugate. Of these, the rPA-ILNmF3 and rPA-ILNmB10 proteins displayed the highest relative affinity to the BSA-αGal glycoconjugate, exhibiting similar dose response curves, while the rPA-ILNmB4 protein displayed a lower binding capability. The rPA-ILNmE6 protein also showed some capacity to bind the BSA-αGal conjugate but only at relatively high concentrations of the lectin and signal strengths did not reach saturation over the lectin concentration range examined. The remaining rPA-ILNm proteins, in particular rPA-ILNmC5 and rPA-ILNmF6 proteins, showed very little binding to BSA-αGal even at relatively high lectin concentrations of 10 μg $mL^{-1}$ (data not shown). The data against the two glycoconjugates clearly showed that while some of the rPA-ILNm proteins, like rPA-ILNmE6 and rPA-ILNmC5, exhibited selectivity towards BSA-LacNAc; others, like rPA-ILNmF3, exhibited dual binding specificities for α- and β-linked galactose by binding both glycoconjugates (FIG. 4C).

Lectin Dose Response Curves on Natural Glycoproteins Glycoforms—

Lectin dose response curves were also generated against asialotransferrin and asialofetuin (FIGS. 5A & 5B). These natural glycoproteins display glycans at significantly lower densities than the glycoconjugates. Data obtained using these targets therefore gives a greater, and more biologically relevant, insight into the binding activities and dependencies of the rPA-ILNm proteins. The rPA-ILNmE6 protein displayed a very high relative affinity for both asialotransferrin and asialofetuin with lectin dose response curves reaching saturation for both glycoproteins at lectin concentrations above 1 μg $mL^{-1}$. The rPA-ILNmF3 and rPA-ILNmB10 proteins also displayed high relative affinities to both asialotransferrin and asialofetuin, albeit not as high as rPA-ILNmE6. While the rPA-ILNmC5 was observed to bind strongly to asialofetuin, it only bound relatively weakly to asialotransferrin. This indicated that binding of this protein to LacNAc is potentially more dependent on the density or distribution of glycans, and possibly more reliant on avid binding, than rPA-ILNmE6. The rPA-ILNmG3 protein showed similar responses to both glycoproteins as rPA-ILNmC5. The rPA-ILNmF6 protein displayed a higher relative affinity for both asialotransferrin and asialofetuin than either the rPA-ILNmC5 or rPA-ILNmG3 proteins and generated a lectin dose response curve against asialofetuin comparable to that of the rPA-ILNmF3 and rPA-ILNmB10 proteins. This indicates that the rPA-ILNmF6 is potentially less dependent on high density display of target ligands for effective binding and has a higher affinity for terminal β-linked galactose than rPA-ILNmC5 or rPA-ILNmG3.

Determination of Affinity Constants for rPA-ILNm Proteins—

A relative affinity constant, $K_D$, was calculated for selected rPA-ILNm proteins against the BSA-LacNAc glycoconjugate according the method described by Kirkeby et al 2002. $K_D$ is defined as being the concentration of the glycoconjugate required to fill half of the available lectin binding sites at equilibrium. If a lectin has a high affinity for the glycoconjugate, then the $K_D$ will be low as it will take a lower concentration of glycoconjugate to bind half of the lectin molecules. The calculated $K_D$ for rPA-ILNmE6, rPA-ILNmF3 and ECL for BSA-LacNAc were 4 ng, 6.3 ng and 21 ng, respectively (FIG. 6) indicating that the rPA-ILNmE6 protein had approximately a 5 fold greater affinity for the BSA-LacNAc glycoconjugate than ECL while rPA-ILNmF3 had a 3 fold greater affinity.

Application of Immobilized rPA-ILNmE6 for Glycoprotein and Glycoform Isolation— to evaluate the ability of rPA-ILNmE6 to be used for selective glycoprotein and glycoform isolation and purification. The lectin was immobilized onto CNBr activated Sepharose 4B. The lectin readily immobilized at high densities and lectin immobilization densities of approximately 20 mg $mL^{-1}$ of resin were reproducibly achieved. To evaluate the ability of this lectin affinity resin to isolate glycoproteins displaying terminal LacNAc, we first performed simple lectin pull down assays in eppendorf tubes using a test protein mixture prepared by mixing asialotransferrin, glucose oxidase (displays high mannose), cytochrome C and carbonic anhydrase (both non-glycosylated). Fractions of unbound and bound protein were ultimately evaluated by SDS-PAGE (FIG. 7A). As can be seen from FIG. 7A, the rPA-ILNmE6 Sepharose resin selectively extracted the asialotransferrin from the protein mixture and the protein was effectively recovered by the incorporation of free galactose into elution buffers. The rPA-ILNmE6 Sepharose resin was also packed into 1 mL FPLC column housings to enable easy attachment to FPLC systems. We evaluated the ability of this column to efficiently separate glycoforms of transferrin. A test sample containing equal amounts of transferrin and asialotransferrin was injected onto the FPLC column and was separated into two clear fractions, one unbound protein fraction and one galactose eluted bound protein fraction (FIG. 7B). Both the bound and unbound fractions were assessed by ELLA to evaluate their glycoprotein composition (FIG. 7C). In ELLA's transferrin was shown to generate strong responses from the sialic acid specific lectin SNA but did not respond significantly with either of the galactophilic lectins ECL or rPA-ILNmE6. Asialotransferrin showed a reduced response to the SNA but significantly increased responses to both of the galactophilic lectins. While this confirmed the presence of terminal β1,4-linked galactose and it also indicated that the neuraminidase treatment used in the preparation of the asialotransferrin had in fact generated partially desialylated glycoforms. When the FPLC fractionated material was assessed only the bound fraction was found to elicit responses from the galactophilic lectins. This indicated that the rPA-ILNmE6 Sepharose column had efficiently separated the transferrin and asialotransferrin glycoforms into two distinct populations and that it had effectively isolated the partially desialylated transferrin glycoforms.

Discussion

In the present study, we have demonstrated how the carbohydrate binding specificity of the α-galactophilic PA-IL protein could be significantly altered through random mutagenesis of specific amino acid residues in its binding site. We identified a number of novel RPL's exhibiting specificity and high affinity for glycoproteins displaying LacNAc and an affinity for this glycan epitope significantly greater than that of commercially available plant lectin ECL (FIG. 6). While some of the rPA-ILNm proteins displayed distinct selectivity towards LacNAc (rPA-ILNmE6 and rPA-ILNmC5), others displayed dual specificity binding to both LacNAc and glycans with terminal α-linked galactose (rPA-ILNmF3 and PA-ILNmB10) (FIG. 4C). In addition to this, there were clear differences in the relative affinities of rPA-ILNm proteins for different glycoprotein targets. Through the functional characterisation of this collection of mutants, and identification of the specific amino acid substitutions in each, we were able to identify specific substitutions at each of the mutagenized positions in the parental rPA-ILN protein that were linked with specific carbohydrate binding activities.

The Role of Specific Amino Acid Substitutions in Dictating Carbohydrate Binding Properties—

Of the rPA-ILNm proteins identified, the rPA-ILNmE6 protein appeared to exhibit a very high relative affinity for BSA-LacNAc. While this protein also showed some capacity to bind to the BSA-αGal glycoconjugate, it only did so relatively weakly when compared to its response to the BSA-LacNAc glycoconjugate (FIG. 4C). The rPA-ILNmC5 also appeared to bind well to BSA-LacNAc, albeit not as well as rPA-ILNmE6 (FIG. 4B), but was not observed to bind to the BSA-αGal conjugate (FIG. 4A). When these two proteins were examined against asialofetuin and asialotransferrin, it became clear that the rPA-ILNmE6 potentially had a significantly higher affinity for LacNAc than the rPA-ILNmC5 protein, which appeared to be more dependant of the density of glycan display (FIG. 5). The rPA-ILNmC5 protein carries the same H50N substitution present in rPA-ILNmE6 but carries different substitutions at the Asp52 and Gln53 positions. These results indicate that, while the H50N substitution may be associated with high affinity binding to LacNAc, the D52N and Q53G substitutions present in rPA-ILNmE6 play a role in further modulating its carbohydrate binding properties resulting in its significantly higher relative binding affinities for LacNAc compared to rPA-ILNmC5.

The responses of another group of rPA-ILNm proteins indicated that a H50V substitution could also support high affinity binding to LacNAc. This substitution was present in rPA-ILNmF3, rPA-ILNmB10 and rPA-ILNmG3 and all of these proteins were observed to bind strongly to the BSA-LacNAc glycoconjugate. Analysis against asialofetuin and asialotransferrin again indicated however that the rPA-ILNmB10 and rPA-ILNmF3 proteins displayed a higher relative affinity for LacNAc than the rPA-ILNmG3, although not as high as that displayed by the rPA-ILNmE6 protein. The rPA-ILNmF3 and rPA-ILNmB10 proteins also displayed strong binding to the BSA-αGal, albeit not as strong as the parental rPA-ILN protein, and this was not observed for the rPA-ILNmG3 protein. As these three proteins only differ from each other by possessing different substitutions at positions 52 and 53, this again demonstrates that amino acids at these positions play a role in further defining the specificity and affinity of the rPA-ILNm proteins. The rPA-ILNmB10 and rPA-ILNmF3 proteins actually only differ from each other at one position, carrying a Q53E and a Q53R substitution respectively. The Q53R substitution was also present in rPA-ILNmB4 which also binds well to the BSA-αGal. These data indicated that substitution of Gln53 with a basic (Arg) or acidic (Glu) residue could be linked with a higher affinity for α-linked galactose.

Another interesting observation was that, while the lectin dose response curves for rPA-ILNmF3 and rPA-ILNmB10 proteins on asialotransferrin did not increase as rapidly as that of rPA-ILNmE6, indicative of a lower relative affinity, they ultimately reached a higher absorbance plateau indicating a greater final density of these proteins bound to the surface. However, we had observed that both of these proteins had a tendency to form aggregates when high protein concentration stock solutions, stored at −80° C., were being defrosted. These aggregates generally went back into solution when samples were fully thawed but all samples were centrifuged to ensure removal of any residual protein aggregates prior to use. These proteins occasionally also generated high signals in negative control wells. This was also observed for the rPA-ILNmE12 protein, albeit more consistently, leading to it being excluded from further analysis. The one common feature of all three of these proteins was the occurrence of a D52C substitution and it is possible that this residue could mediate protein aggregation at high lectin concentrations through disulfide bond formation. As a result, the higher saturation signals obtained for these lectins on asialotransferrin may be the result of binding of protein aggregates formed at high lectin concentrations.

Novel Glycoanalytical Tools for Applications in the Life Sciences—

Lectins have found widespread applications within the field of glycobiology and have been implemented in a diverse range of formats to characterise the glycosylation status, and to detect changes in glycosylation, of biomolecules. Changes in the glycosylation of proteins or cell surfaces can be concurrent with, and indicative of, a change in the physiological status of a cell or the development of a disease state and can therefore be used as a means of diagnosis (1-5). LacNAc is an important glycan epitope commonly displayed on cell surfaces and as part of the antenna of complex N-linked glycan structures of glycoproteins. For example, serum IgG's, unlike many other serum glycoproteins, are not heavily sialylated and the N-linked glycans present in the Fc region of the glycoproteins usually bear biantennary glycans terminating in LacNAc (11,24). A reduction in terminal β1,4 galactosylation of these N-linked glycans has been diagnostically linked with a number of autoimmune disorders including rheumatoid arthritis while increased galactosylation indicates remission of the disease (11-14,40). The RPL's we have developed were clearly demonstrated to be capable of sensitively detecting glycoproteins displaying terminal LacNAc and of being capable of differentiating between different glycoprotein glycoforms (FIG. 2). Lectin affinity chromatography (LAC) is also widely used for the separation and isolation of glycoproteins. With more than 50% of proteins being glycosylated LAC is a particularly powerful tool for glycoproteomic analysis. Proteomic samples are highly complex and glycoproteins in biological materials are often only present in very small quantities and efficient isolation and pre-concentration of these molecules is essential for their identification and characterisation. LAC is often also used as an initial step to pre-concentrate oligosaccharides, glycopeptides, or to separate glycoforms, prior to MS based glycoanalysis (39,41-43). We clearly demonstrated that the novel galactophilic RPL's reported here could be immobilized at high densities onto solid support matrices, such as Sepharose, to generate highly effective bioaffinity matrices enabling efficient separation and selective purification of glycoproteins and glycoforms displaying terminal β1,4-linked galactose (FIG. 7). The RPL's reported here could therefore find widespread applications in the fields of functional glycomics and proteomics.

Many biopharmaceutical products are glycosylated molecules and variations in glycosylation of bio-therapeutics can have a very significant impact on a products physiochemical properties, efficacy, and immunogenicity (11,44-47). Sialylation of some bio-therapeutics, such as Erythropoietin (EPO), can have a significant impact on their physiochemical properties, blood retention and overall efficacy (44,46,48,49). Monitoring of sialylation of these products is often an important determinant in the production of these products and methods using lectins, such as ECL, to monitor for changes in sialylation have been reported in the literature (48,50). Monoclonal antibodies (MAb's) represent a very significant and rapidly growing class of biotherapeutics (11,24). The N-linked glycans in the Fc region of MAb's are usually terminated in galactose and these glycans are essential for the ability of MAb's to elicit ADCC (Antibody Dependent Cellular Cytotoxicity) and CDC (Complement Dependent Cytotoxicity) effector functions vital for their efficacy (11,12,24, 40,51). As with the analysis of other glycoproteins, LAC can enable more efficient analysis and characterisation of glycosylated biotherapeutics. With their specificity for LacNAc, the RPL's reported here could be particularly useful in the analysis of MAb's to determine the extent of terminal galactosylation which is often a major source of heterogeneity in these products (12). In addition to the many potential analytical scale applications, the ability to readily scale the production of our novel RPL's, could also enable them to ultimately overcome the many barriers that have limited the application of other eukaryotic lectins and enable them to be applied at a production scale, in a way analogous to Protein A, for the selective purification of optimal biotherapeutic glycoforms to produce safer more efficacious drugs.

EXAMPLE B

Experimental Procedures

Site Directed Mutagenesis—

PCR based site directed mutagenesis of the lecA gene, which encodes the PA-IL protein, was achieved as described in Example A. The pQE30PA-IL vector is an *Escherichia coli* expression vector which expresses the rPA-ILN protein (recombinant PA-IL protein with an N-terminally positioned hexa-histidine (6HIS) affinity purification tag) and this was used as a template for whole vector amplification (See Example A—Table A1). Whole vector amplification was achieved using 5' phosphorylated primers designed to anneal within the lecA sequence with their 5' ends exactly next to each other. The reverse primers were designed to overlap the region to be mutagenized. This enabled the introduction of mutations through manipulation of reverse primer sequences while the sequence of the forward primer, PA-ILmutF, was kept constant (Table B2). Successful PCR reactions were purified and subjected to digestion with the restriction enzyme DpnI to selectively digest the parental template vector DNA. Digestions were ultimately run on agarose gels and PCR products corresponding to the expected size of linear vector were gel extracted. The final purified PCR products, with blunt phosphorylated ends, were re-circularised by simple self-ligation and the ligated DNA transformed into *E. coli* strain KRX. Typically three transformants were picked into overnight 10 mL Terrific Broth (TB) cultures supplemented with 50 μM IPTG and expression of mutant rPA-ILN proteins (rPA-ILNm) confirmed by SDS-PAGE analysis of total cellular protein. Plasmid DNA was isolated from clones expressing proteins of the expected size and successful introduction of the desired mutations confirmed by DNA sequencing (MWG-Eurofins). All of the plasmids used in this study are described in Table B1 and all of the primers used are described in Table B2.

TABLE B1

Plasmids Constructed in Example B.
Plasmids Encoding Mutagenised rPA-ILN (rPA-ILNm) Proteins

| Plasmid Name | Protein Expressed | Amino Acid Substitutions | Source |
|---|---|---|---|
| H50 Single Mutants | | | |
| pPC30PA-IL-A | H50A | H50A | Example B |
| pPC30PA-IL-V | H50V | H50V | Example B |
| pPC30PA-IL-L | H50L | H50L | Example B |
| pPC30PA-IL-F | H50F | H50F | Example B |
| pPC30PA-IL-P | H50P | H50P | Example B |
| pPC30PA-IL-S | H50S | H50S | Example B |
| pPC30PA-IL-T | H50T | H50T | Example B |
| pPC30PA-IL-N | H50N | H50N | Example B |
| pPC30PA-IL-Q | H50Q | H50Q | Example B |
| pPC30PA-IL-D | H50D | H50D | Example B |
| pPC30PA-IL-E | H50E | H50E | Example B |
| pPC30PA-IL-K | H50K | H50K | Example B |
| pPC30PA-IL-R | H50R | H50R | Example B |
| H50N:Q53 Double Mutants | | | |
| pPC30PA-IL-NA | H50N:Q53A | H50N:Q53A | Example B |
| pPC30PA-IL-NV | H50N:Q53V | H50N:Q53V | Example B |
| pPC30PA-IL-NL | H50N:Q53L | H50N:Q53L | Example B |
| pPC30PA-IL-NG | H50N:Q53G | H50N:Q53G | Example B |
| pPC30PA-IL-NS | H50N:Q53S | H50N:Q53S | Example B |
| pPC30PA-IL-NY | H50N:Q53Y | H50N:Q53Y | Example B |
| pPC30PA-IL-NN | H50N:Q53N | H50N:Q53N | Example B |
| pPC30PA-IL-ND | H50N:Q53D | H50N:Q53D | Example B |
| pPC30PA-IL-NE | H50N:Q53E | H50N:Q53E | Example B |
| pPC30PA-IL-NK | H50N:Q53K | H50N:Q53K | Example B |
| pPC30PA-IL-NR | H50N:Q53R | H50N:Q53R | Example B |
| pPC30PA-IL-NH | H50N:Q53H | H50N:Q53H | Example B |
| Additional H50:Q53 Double Mutants | | | |
| pPC30PA-IL-VK | H50V:Q53K | H50V:Q53K | Example B |
| pPC30PA-IL-VR | H50V:Q53R | H50V:Q53R | Example B |
| pPC30PA-IL-QK | H50Q:Q53K | H50Q:Q53K | Example B |
| pPC30PA-IL-QR | H50Q:Q53R | H50Q:Q53R | Example B |
| Q53 Single Mutants | | | |
| pPC30PA-IL-HK | Q53K | Q53K | Example B |
| pPC30PA-IL-HR | Q53R | Q53R | Example B |
| pPC30PA-IL-HE | Q53E | Q53E | Example B |

TABLE B2

| Primer Sequences Used in Example B for Site Directed Mutagenesis of rPA-ILN. | |
|---|---|
| Forward Primer | |
| PA-ILmutF | Cgttttgtggtgcgctggtcatgaagattggc - SEQ ID NO. 48 |
| Reverse Primers Used for Generation of Specific H51 Mutants | |
| H50A | cgtcgtggcagatcagcccttggtccgg**TGC**ctcccgatcgccctg - SEQ ID NO. 49 |
| H50V | cgtcgtggcagatcagcccttggtccgg**TAC**ctcccgatcgccctg - SEQ ID NO. 50 |
| H50L | cgtcgtggcagatcagcccttggtccgg**CAG**ctcccgatcgccctg - SEQ ID NO. 51 |
| H50F | cgtcgtggcagatcagcccttggtccgg**AAA**ctcccgatcgccctg - SEQ ID NO. 52 |
| H50P | cgtcgtggcagatcagcccttggtccgg**CGG**ctcccgatcgccctg - SEQ ID NO. 53 |
| H50S | cgtcgtggcagatcagcccttggtccgg**AGA**ctcccgatcgccctg - SEQ ID NO. 54 |
| H50T | cgtcgtggcagatcagcccttggtccgg**GGT**ctcccgatcgccctg - SEQ ID NO. 55 |
| H50N | cgtcgtggcagatcagcccttggtccgg**ATT**ctcccgatcgccctg - SEQ ID NO. 56 |
| H50Q | cgtcgtggcagatcagcccttggtccgg**TTG**ctcccgatcgccctg - SEQ ID NO. 57 |
| H50D | cgtcgtggcagatcagcccttggtccgg**ATC**ctcccgatcgccctg - SEQ ID NO. 58 |
| H50E | cgtcgtggcagatcagcccttggtccgg**TTC**ctcccgatcgccctg - SEQ ID NO. 59 |
| H50K | cgtcgtggcagatcagcccttggtccgg**TTT**ctcccgatcgccctg - SEQ ID NO. 60 |
| H50R | cgtcgtggcagatcagcccttggtccgg**TCT**ctcccgatcgccctg - SEQ ID NO. 61 |
| Reverse Primers Used for Generation of Specific Double Mutants | |
| H50N:Q53A | cgtcgtggcagatcagccc**CGC**atccgg**GTT**ctcccgatcgccctg - SEQ ID NO. 62 |
| H50N:Q53V | cgtcgtggcagatcagccc**CAC**atccgg**GTT**ctcccgatcgccctg - SEQ ID NO. 63 |
| H50N:Q53L | cgtcgtggcagatcagccc**CAG**atccgg**GTT**ctcccgatcgccctg - SEQ ID NO. 64 |
| H50N:Q53G | cgtcgtggcagatcagccc**GCC**atccgg**GTT**ctcccgatcgccctg - SEQ ID NO. 65 |
| H50N:Q53S | cgtcgtggcagatcagccc**GCT**atccgg**GTT**ctcccgatcgccctg - SEQ ID NO. 66 |
| H50N:Q53Y | cgtcgtggcagatcagccc**ATA**atccgg**GTT**ctcccgatcgccctg - SEQ ID NO. 67 |
| H50N:Q53N | cgtcgtggcagatcagccc**GTT**atccgg**GTT**ctcccgatcgccctg - SEQ ID NO. 68 |
| H50N:Q53D | cgtcgtggcagatcagccc**ATC**atccgg**GTT**ctcccgatcgccctg - SEQ ID NO. 69 |
| H50N:Q53E | cgtcgtggcagatcagccc**TTC**atccgg**GTT**ctcccgatcgccctg - SEQ ID NO. 70 |
| H50N:Q53K | cgtcgtggcagatcagccc**TTT**atccgg**GTT**ctcccgatcgccctg - SEQ ID NO. 71 |
| H50N:Q53R | cgtcgtggcagatcagccc**GCG**atccgg**GTT**ctcccgatcgccctg - SEQ ID NO. 72 |
| H50N:Q53H | cgtcgtggcagatcagccc**ATG**atccgg**GTT**ctcccgatcgccctg - SEQ ID NO. 73 |
| H50V:Q53K | cgtcgtggcagatcagccc**TTT**atccgg**CAC**ctcccgatcgccctg - SEQ ID NO. 74 |
| H50V:Q53R | cgtcgtggcagatcagccc**GCG**atccgg**CAC**ctcccgatcgccctg - SEQ ID NO. 75 |
| H50Q:Q53K | cgtcgtggcagatcagccc**TTT**atccgg**CTG**ctcccgatcgccctg - SEQ ID NO. 76 |
| H50Q:Q53R | cgtcgtggcagatcagccc**GCG**atccgg**CTG**ctcccgatcgccctg - SEQ ID NO. 77 |
| Reverse Primers Used for Generation of Specific Q53 Mutants | |
| Q53K | cgtcgtggcagatcagccc**TTT**atccggatgctcccgatcgccctg - SEQ ID NO. 78 |
| Q53R | cgtcgtggcagatcagccc**GCG**atccggatgctcccgatcgccctg - SEQ ID NO. 79 |
| Q53E | cgtcgtggcagatcagccc**TTC**atccggatgctcccgatcgccctg - SEQ ID NO. 80 |

Protein Expression and Purification—

For protein expression, plasmids were transformed into the protease deficient *E. coli* strain KRX (30). Expression clones were cultured in Terrific Broth (TB). Cultures were grown at 37° C. with shaking at 200 rpm until an optical density of 0.6 at 600 nm was reached and then induced by addition of IPTG to a final concentration of 50 μM. Cultures were then placed at 30° C. with shaking at 200 rpm for overnight incubation. Cells were harvested by centrifugation and cell pellets resuspended in lysis buffer (10 mM $NaH_2PO_4$, 300 mM NaCl, 40 mM imidazole, pH 8.0). Cell disruption was achieved by high pressure using a Constant Systems cell disrupter and cell debris was removed by centrifugation. Clarified cell lysates were applied to 10 mL IMAC columns (IMAC Hypercel from Pal) and a high stringency wash buffer with 100 mM imidazole was used to remove non-specifically bound contaminating proteins. The desired 6HIS tagged proteins were ultimately eluted using 250 mM immidizole and eluted proteins were aliquoted and stored at −80° C. in the elution buffer. Typical yields were around 200 mg per 250 mL starting culture. Purified proteins were analysed by SDS-PAGE to assess purity and routinely buffer exchanged and concentrated using Vivaspin centrifugal membrane devices (Sartorius-Stedim), with a molecular weight cut off of 10 kDa, according to the manufacturer's guidelines.

General Enzyme Linked Lectin Assay (ELLA) Method—

The Gal-α1,3-Gal-BSA (BSA-αGal) and Gal-β1,4-GlcNAc-BSA (BSA-LacNAc) glycoconjugates used were from Dextra Laboratories and presented on average 20 glycan moieties per BSA molecule. Biotinylated plant lectins GSL-I (*Griffonia simplicifolia* isolectin B4), ECL (*Erythrina crista-galli* Lectin), RCA (*Ricinus communis* Agglutinin), SNA (*Sambucus nigra* Agglutinin) and MALII (*Maackia amurensis* Lectin) were from Vector Laboratories. Human transferrin was from Sigma Aldrich and asialotransferrin (AsT) was generated by treatment using neuraminidase (*Clostridium perfingens*) in accordance with manufacturer's guidelines (New England Biolabs). ELLA's were essentially performed according to the method described by Thompson et al (2011) (33). More specifically, glycoproteins were prepared in PBS and typically immobilized at a concentration of 5 μg $mL^{-1}$. For qualitative ELLA's lectins were assayed at a concentration of 2 μg $mL^{-1}$ in TBST (20 mM Tris, 150 mM NaCl, 0.05% Tween-20, 1 mM $CaCl_2$, 1 mM $MnCl_2$, 1 mM $MgCl_2$, pH 7.6). For lectin dose response experiments, each lectin was evaluated at a range of concentrations prepared by serial 1:2 dilution of an initial lectin solution of 2 μg $mL^{-1}$ to a final concentration of 31 ng $mL^{-1}$. Binding of 6HIS tagged rPA-IL proteins was detected after 1 hour incubation at 25° C. using a HRP conjugated anti-HIS antibody diluted 1:10,000 in TBST (Sigma Aldrich). Biotinylated plant lectins were detected using a HRP conjugated anti-biotin antibody diluted 1:10,000 in TBST (Sigma Aldrich).

Protein Structural Modelling and Image Rendering—

In silico analysis of the PA-IL protein and its carbohydrate binding site was carried out using the PDB file 2VXJ (23). Structural models were generated using Deep View (Swiss Model) (25) and models generated were ultimately rendered using the CCP4MG software (26).

Results

In Example A, we constructed an expression vector, pQE30PA-IL, enabling the expression of rPA-IL with an N-terminally positioned poly-histidine tag (rPA-ILN). This poly-histidine (6HIS) tag enabled rapid and simple purification of the rPA-ILN protein by IMAC and therefore independently of its carbohydrate binding specificity. Positioning of the poly-histidine tag at the N-terminus of the rPA-IL protein was found to disrupt the quaternary structure of the protein resulting in the formation of homodimers rather than the native tetrameric configuration adopted by the wild type untagged PA-IL protein. Despite this, the rPA-ILN protein, and derived rPA-ILNm proteins, were demonstrated in Example A to be active and binding could be detected with high sensitivity in ELLA's against defined glycoprotein targets. The pQE30PA-IL vector was therefore selected as the target DNA molecule for mutagenesis studies undertaken in this work. As all of the rPA-ILNm generated would exhibit an equivalent quaternary structure to the parental rPA-ILN protein, comparative analysis of carbohydrate binding specificity and affinity could be performed by ELLA to assess the impact of specific amino acid substitutions.

The His50 Residue is Critical for Dictating the Binding Specificity of rPA-ILN—

Work conducted in Example A indicated that the His50 residue in the binding pocket of the PA-IL protein played a critical role in determining the carbohydrate binding specificity of the protein. To independently examine the role of this amino acid residue, it was substituted with 13 alternative amino acids selected to be representative of the full spectrum of potential amino acid prosperities (Table B1 above). All of the resulting rPA-ILNm proteins were successfully expressed *in E. coli* and purified by IMAC with the exception of one carrying a H50D mutation, which was found to be insoluble. An rPA-ILNm protein carrying a H50P substitution was observed to express weakly in *E. coli* and, when purified protein was assessed by SDS-PAGE, it generated multiple high molecular weight bands indicating that it potentially formed aggregates (data not shown). The carbohydrate binding properties of each of the remaining 12 successfully purified His50 substituted rPA-ILNm proteins was qualitatively assessed by performing ELLA's against two specific BSA glycoconjugate targets; Gal-α1,3-Gal-BSA (BSA-αGal) and Gal-β1,4-GlcNAc-BSA (BSA-LacNAc) (FIG. 13). The glycoprotein asialotransferrin (AsT) was also included in this initial screen. This glycoprotein has only two N-linked glycans (36) and therefore displays a significantly lower density of glycans with terminal LacNAc than the BSA-LacNAc glycoconjugate. We had observed in Example A that, while BSA-LacNAc was useful for detecting weak binding events, AsT was more useful in detecting subtle differences in the relative binding affinities of proteins where binding might be more dependent on the surface distribution and/or density of glycan moieties. Several of the random mutants generated in Example A (Table A1 above), and a number of commercially available plant lectins, were also included in these qualitative assays for comparative purposes. These screens identified a number of amino acid substitutions that significantly altered the carbohydrate binding properties of the parental rPA-ILN protein, including some that generated rPA-ILNm proteins exhibiting significant binding to LacNAc (FIG. 13). This clearly demonstrated that substitution of the His50 residue alone was sufficient to alter carbohydrate binding properties.

Specific His50 Substitutions Result in High Affinity Binding to Terminal β1,4-Linked Galactose Initial screens identified a number of His50 substitutions that generated rPA-ILNm proteins exhibiting strong binding to BSA-LacNAc (FIG. 13). Interestingly, these included H50N, H50V and H50T substitutions that had been observed in randomly mutated rPA-ILNm proteins identified in Example A as exhibiting high affinity for glycoproteins displaying terminal β1,4-linked galactose (Table A1). In addition to these substitutions, H50E and H50Q substitutions were also observed to generate proteins exhibiting strong binding to BSA-LacNAc. While an rPA-ILNm protein carrying a H50P substitution was observed binding to BSA-LacNAc, it was also observed to form aggregates when run on SDS-PAGE. The true affinity of this protein for LacNAc would therefore be difficult to interpret and to compare to that of the other rPA-ILNm proteins, so further analysis of this protein was not conducted. A protein carrying a H50L substitution was also observed to bind to BSA-LacNAc but the signal obtained was weaker than that observed for the H50V or H50T proteins. Lectin dose response curves were generated for each of the five His50 substituted rPA-ILNm proteins that generated the strongest signals against BSA-LacNAc in the initial ELLA screens (FIG. 14A). This enabled a more quantitative comparison of the relative affinities of these proteins for the glycoconjugate and a more quantitative assessment of the impact of each of the specific His50 substitutions on the carbohydrate binding properties of the rPA-ILN protein.

Of all of the His50 substitutions made, the H50N protein exhibited the highest relative affinity for BSA-LacNAc. This was only slightly weaker than that observed for the random mutant rPA-ILNmE6 protein which carries the same H50N substitution but also carries two additional D52N and Q53G amino acid substitutions (FIG. 14A). However, the H50N generated significantly lower signals on AsT, approximately half that observed for the rPA-ILNmE6 protein (FIG. 13), indicating that it had a significantly lower relative affinity for glycans with terminal LacNAc and that binding was more dependent on the surface density and the context in which glycans were displayed. This behaviour was also observed for another random mutant, rPA-ILNmC5, which also carried a H50N substitution along with D52T and Q53S substitutions (FIG. 13). The H50E protein was also observed to bind strongly to BSA-LacNAc displaying a relative binding affinity that was only slightly weaker than that observed for the H50N protein (FIG. 14A). However, it failed to bind significantly to AsT (FIG. 13) indicating that it potentially had an even lower relative affinity for LacNAc, and an even greater dependency on the density of glycan display, than the H50N protein. The H50V protein generated binding signals against BSA-LacNAc comparable to that of the random mutant, rPA-ILNmF3, which carries the same H50V substitution along with D52C and Q53R substitutions. However, in contrast to the rPA-ILNmF3 protein, H50V failed to bind significantly to AsT, indicating it had a lower relative higher affinity for glycans with terminal β1,4-linked galactose (FIG. 13). Lectin dose response curves demonstrated that the relative binding affinity of H50V for BSA-LacNAc was significantly lower than that observed for either the H50N or the H50E proteins but greater than that observed for the H50Q and H50T proteins (FIG. 14A).

His50 Substitutions Result in Reduced Binding Affinities for α-Linked Galactose—

All of the His50 substitutions negatively impacted on the ability of rPA-ILNm proteins to bind to the BSA-αGal glycoconjugate. Proteins carrying either a H50Q or a H50K substitution exhibited the strongest binding to the BSA-αGal glycoconjugate (FIG. 13) but their relative affinities for this conjugate were still significantly lower than that of the parental rPA-ILN protein (FIG. 14B). The H50K protein, like the parental rPA-ILN protein, bound relatively strongly to BSA-αGal but did not bind to BSA-LacNAc (FIG. 13). The H50Q protein, however, exhibited dual specificity exhibiting relatively strong binding signals on BSA-LacNAc and the strongest binding of all of the His50 mutants toward the BSA-αGal glycoconjugate (FIG. 13).

The H50N protein generated significant binding signals against BSA-αGal (FIG. 13) and lectin dose response curves showed that it had a significantly higher affinity for this glycoconjugate than that observed for the rPA-ILNmE6 protein (FIG. 14B). Therefore, while this protein still exhibited significant preferential binding to BSA-LacNAc, it was not as selective as the rPA-ILNmE6 protein. While the H50V protein had been observed to bind with relatively high affinity to BSA-LacNAc, it did not exhibit significant binding to the BSA-αGal glycoconjugate. This was in contrast to the rPA-ILNmF3 protein that was observed to bind relatively strongly to both BSA glycoconjugates (FIG. 13). Similarly, the H50T protein bound to BSA-LacNAc with comparable strength to that observed for the rPA-ILNmB4 protein but, unlike the rPA-ILNmB4 protein, it exhibited negligible binding to the BSA-αGal glycoconjugate (FIG. 13).

The Q53 and D52 Residues Play a Role in Modulating Carbohydrate Binding Specificity and Affinity—

Analysis of the rPA-ILNm proteins with single His50 substitutions, and comparison with the sugar binding properties of closely related randomly mutated rPA-ILN proteins, clearly indicated that the Gln53 and D52 residues played a role in further modulating the carbohydrate binding properties of the rPA-ILNm proteins. We first examined the impact of Gln53 substitutions when made in conjunction with a H50N substitution. The plasmid encoding the H50N protein was mutagenized using primers specifically designed to introduce an additional specific amino acid substitution in place of the Gln53 residue (Table B2 above). This generated twelve new expression vectors, each expressing an rPA-ILNm protein with the H50N substitution in combination with one of 12 different amino acid substitutions in place of the Gln53 residue (Table B1). One of the resulting proteins, H50N:Q53Y, was found to be insoluble and was not characterised further. The remaining 11 mutants were evaluated as before by performing ELLA analysis against BSA-LacNAc, BSA-αGal and AsT (FIG. 15). All of the H50N:Q53 double mutants exhibited comparable activity when tested against BSA-LacNAc. Examination of binding signals towards AsT revealed subtle differences in binding affinity with most substitutions resulting in a slight reduction in binding signals. This was particularly unexpected in the case of the H50N:Q53G double substitution. Based on the carbohydrate binding properties of the rPA-ILNmE6 protein, one might have expected that the introduction of a Q53G substitution would result in some enhancement in binding to AsT and a closer approximate activity to that of the rPA-ILNmE6 protein. Instead binding was actually weaker than that of the H50N protein and was less than half the strength of the signal observed for the rPA-ILNmE6 protein. Most Gln53 substitutions also resulted in a significant reduction in binding to the BSA-αGal glycoconjugate compared to the parental H50N protein. While binding to the BSA-αGal glycoconjugate was generally reduced to levels comparable to that of the rPA-ILNmE6 protein, most of the proteins also bound more weakly to AsT suggesting that this apparent increase in selectivity was in fact due to an overall reduction in the affinity of carbohydrate binding. However, one protein of note was the H50N:Q53E protein which displayed significantly reduced binding to AsT compared to the parental H50N but displayed comparable, and potentially slightly stronger, binding to the BSA-αGal. This suggests that the Q53E substitution might preferentially promote binding to terminal α-linked galactose over β-linked galactose.

Q53R Substitutions Promote Binding to α-Linked Galactose—

Comparison of the binding specificities of the H50T and H50V proteins with that of the rPA-ILNmB4 and rPA-ILNmF3 proteins respectively, suggested that a Q53R substitution might promote binding to terminal α-linked galactose. We therefore introduced a Q53R substitution into the H50V protein and the resulting H50V:Q53R protein was observed to bind more strongly to the BSA-αGal glycoconjugate (FIG. 16A). Lectin dose response curves showed that this double mutant exhibited a comparable relative affinity for BSA-αGal to that of the rPA-ILNmF3 protein (FIG. 16B). The H50V:Q53R protein also showed significantly stronger binding to AsT than the parental H50V and this was also comparable to that observed for the rPA-ILNmF3 protein (FIG. 16A). Substitution of the Gln53 residue with a larger lysine residue generated the H50V:Q53K protein which displayed an overall reduced carbohydrate binding activity compared to the parental H50V protein (FIG. 16A). We introduced these same Gln53 substitutions into the H50Q protein to see if there would be a similar impact on carbohydrate binding properties. While the H50Q:Q53R protein was observed to bind with a slightly higher relative affinity to the BSA-αGal glycoconjugate compared to the parental H50Q protein (FIG. 16B), binding to the BSA-LacNAc glycoconjugate was abolished (FIG. 16A).

The above results suggested that a Q53R substitution could promote binding to glycans with terminal α-linked galactose. However, neither the H50Q:Q53R protein nor the H50V:Q53R proteins bound to the BSA-αGal glycoconjugate as strongly as the rPA-ILN protein due to substitution of the His50 residue (FIG. 16B). We therefore introduced the Q53R substitution into the original rPA-ILN protein to determine if it would result in a protein with enhanced affinity for the BSA-αGal glycoconjugate. As expected, the resulting Q53R protein was observed to display a higher relative affinity for the BSA-αGal than the parental rPA-ILN protein and it did not bind to BSA-LacNAc (FIGS. 16A & B). Introduction of a Q53K substitution resulted in almost a complete abolition of binding to either the BSA-LacNAc or BSA-αGal glycoconjugates (FIG. 16A). Based on earlier results observed for a H50N:Q53E double mutant, we also evaluated the impact of introducing a conservative Q53E substitution into the parental rPA-ILN protein. The resulting Q53E protein was found to exhibit an even further enhanced relative affinity for BSA-αGal then the previously made Q53R protein (FIG. 16B).

Discussion

In Example B, we set out to independently assess the roles of the His50, Asp52 and Gln53 residues in the carbohydrate binding site of the rPA-ILN protein in dictating and modulating its carbohydrate binding properties. This was achieved through extensive site directed mutagenesis to introduce specific amino acid substitutions in place of these residues and subsequent evaluation of the carbohydrate binding specificity and affinity of each of the resulting proteins. In doing so, we also aimed to identify specific amino acid substitutions that promoted specifically enhanced carbohydrate binding activities.

The Role of His50 in Defining the α-Galactophilic Selectivity of the PA-IL Protein—

The PA-IL protein has been shown to be α-galactophilic with a preference for glycans displaying α1,4-linked terminal galactose (23). X-ray crystal structures of the protein have been obtained with bound D-galactose and α-galactophilic ligands (23,29). In all of the structures obtained to date, the terminal galactose is bound in the same orientation and this is likely due to the large number of interactions between it, the coordinated calcium and specific amino acid side chains in the binding pocket (FIG. 1B). The PA-IL protein does not bind significantly to glycans with terminal β-linked galactose and consequently no crystal structures with such ligands have been obtained (23). If in silico structural models are generated by overlaying lactose into the carbohydrate binding pocket, placing the terminal β1,4-linked galactose in the orientation observed in crystal structures obtained to date, it can be seen that the second sugar moiety in the oligosaccharide chain would potentially sterically clash with the His50 residue (FIG. 17B). This implies that the His50 residue is likely to be the critical determinant defining the selectivity of the PA-IL protein for glycans with terminal α-linked galactose by sterically inhibiting binding of glycans with terminal β1,4-linked galactose.

The Impact of His50 Substitutions on the Carbohydrate Binding Specificity and Affinity of rPA-ILN—

Our earlier work herein had indicated that substitution of the His50 residue was particularly critical in generating lectins capable of binding with high affinity to glycans displaying LacNAc and terminal β1,4-linked galactose. In Example B, we assessed the role of this residue in dictating carbohydrate binding properties by introducing 13 independent specific amino acid substitutions in its place. Initial qualitative screens of these rPA-ILNm proteins verified that substitution of this residue alone could significantly alter the carbohydrate binding specificity and affinity of the protein. Our results also demonstrated that observed changes in carbohydrate binding activities were not simply due to the alleviation of steric restraints imposed by the His50 residue in the carbohydrate binding site as they were dependent on the His50 substitutions made. Some amino acid substitutions simply had a deleterious impact on the overall carbohydrate binding activity of proteins. However, a number of specific amino acid substitutions generated proteins capable of binding with high affinity to glycans with terminal β1,4-linked galactose. Among these were proteins carrying H50N and H50V substitutions which had also been observed in rPA-ILNm proteins we generated through random mutagenesis in our earlier study herein. Also of particular interest was the H50Q protein, which exhibited a dual specificity binding to both BSA-αGal and BSA-LacNAc glycoconjugates. Through the generation of in silico structural models of these proteins, we explored the potential structural basis for the observed carbohydrate binding specificities of these proteins.

The Carbohydrate Binding Properties of the H50N Protein—

The H50N protein exhibited the highest relative affinity for the BSA-LacNAc glycoconjugate of all of the His50 substitutions made (FIG. 14A) and was also the only His50 substituted protein to bind significantly to AsT (FIG. 13). Examination of a predictive structural model of the PA-IL carbohydrate binding site with a H50N substitution and bound lactose suggests that such a substitution would not only eliminate steric restraints (FIG. 17C), that prevent lactose accessing the wild type PA-IL binding site, but that the asparagine side chain could also potentially participate in forming a number of productive interactions with the bound lactose (FIG. 18A). The hydrophilic side chain of the asparagine could potentially contribute one hydrogen bond with the terminal β1,4-linked galactose moiety, thereby compensating for the loss of at least one of the two hydrogen bonds that would otherwise be contributed by histidine with terminal galactose moieties in the wild type PA-IL. However, it could also contribute two additional hydrogen bonds with the second glucose residue (FIG. 18A). It can also be seen that the Tyr36 side chain could also engage in the formation of hydrogen bonds with the second glucose residue of lactose. The multiple productive interactions between the Asn50 and Tyr36 side chains with the glucose moiety of lactose might explain the relatively high affinity that the H50N protein displays for glycans with LacNAc that we observed in ELLA's. The H50N protein also bound to the BSA-αGal glycoconjugate although with significantly lower relative affinity than that observed against BSA-LacNAc (FIGS. 13 & 14). Examination of the crystal structure of the wild type PA-IL binding site with the iGb3 (Gal-α1,3-Gal-β1,4-Glc) oligosaccharide in the binding site shows that the His50 residue contributes two hydrogen bonds with the terminal α1,3-linked galactose and one with the penultimate galactose residue (FIG. 1B). In a model in which the His50 residue is substituted by asparagine, these productive interactions are lost and there is potentially only one productive interaction between the asparagine side chain and the terminal galactose (FIG. 19A). This might therefore account for the significant reduction in the relative affinity of the H50N protein for BSA-αGal compared to that of the rPA-ILN protein observed in ELLA's.

The Carbohydrate Binding Properties of the H50V Protein—

The H50V protein was also observed to bind strongly to BSA-LacNAc albeit not as strongly as H50N (FIGS. 13 and 14A). Examination of in silico structural models of the PA-IL binding site with a H50V substitution shows that this substitution would make the binding site accessible to lactose (FIG. 17D). However, unlike the asparagine side chain, the smaller hydrophobic side chain of valine would not be able to contribute to the formation of hydrogen bonds with lactose (FIG. 18B). This would explain the lower relative affinity of the H50V protein for BSA-LacNAc than the H50N protein (FIG. 14A) and consequently why, unlike the H50N protein, it failed to bind significantly to AsT (FIG. 13). The valine side chain could however contribute to the stabilization of lactose binding through the formation of hydrophobic interactions with the second glucose residue although these interactions would be likely to be weaker than the hydrogen bonds formed by the asparagine side chain in H50N. As observed in the H50N model, binding of lactose could also be further stabilized by interactions between the side chain of Tyr36 and the glucose residue. While binding of the H50V protein to the BSA-αGal glycoconjugate could be detected, it was very weak. A H50V substitution would result in the loss of the productive interactions contributed by the His50 residue in the PA-IL protein and these would not be compensated for by the replacement valine residue (FIG. 19B). This would also explain why the affinity of H50V for the BSA-αGal was lower than that of H50N where the asparagine side chain could at least contribute to binding through the formation of a hydrogen bond with the terminal α-linked galactose.

The Carbohydrate Binding Properties of the H50Q Protein—

The H50Q protein displayed strong binding to the BSA-LacNAc but it had a significantly lower relative affinity for this glycoconjugate than either the H50N or H50V proteins (FIG. 14A). In structural models of the H50Q binding site, the H50Q substitution would again alleviate the steric constraints imposed by the His50 residue (FIG. 17E). In FIG. 18C, the glutamine side chain is depicted in an orientation where it could contribute two hydrogen bonds with the terminal galactose residue of lactose thereby compensating for those normally contributed by His50 in wild type PA-IL. However, in this orientation it would not engage in productive interactions with the glucose residue. Such interactions with the glucose residue in the lactose disaccharide, observed in models of both the H50N and H50V binding site, may again play a greater role in stabilizing the binding of lactose than the formation of additional hydrogen bonds with a terminal galactose residue already well anchored through extensive interactions with amino acid side chains and the calcium ion. While the Tyr36 side chain could again engage in the formation of positive interactions with the glucose moiety, the inability of the glutamine side chain itself to engage in such interactions might account for the higher relative affinity displayed by both H50N, and H50V, for BSA-LacNAc in ELLA's when compared to that of H50Q. The glutamine side chain is larger than that of asparagine, and significantly larger than that of the hydrophobic valine, and could adopt a number of orientations other than that depicted in FIG. 18C. In silico analysis of alternative models of the H50Q binding site suggested that in some orientations the glutamine side chain may not be able to contribute any productive interactions with the lactose moiety and this could therefore also explain its lower relative affinity for BSA-LacNAc (data not shown). Some of the potential side chain orientations could in fact sterically block lactose from accessing the binding site but, since the H50Q protein was observed to bind the BSA-LacNAc glycoconjugate in ELLA's, these orientations were discounted.

The H50Q protein exhibited stronger binding to BSA-αGal in ELLA's than any of the other proteins with single His50 substitutions (FIG. 13), but its affinity for this glycoconjugate was still significantly weaker than that of the parental rPA-ILN (FIG. 14B). In a model of the H50Q binding site with bound iGb3, it can be seen that the glutamine side chain could potentially contribute to the formation of a hydrogen bond with the second galactose residue in the oligosaccharide (FIG. 19C). This is in contrast to the H50V model where the side chain of valine might not be capable of contributing any productive interactions and this would explain the higher relative affinity of H50Q for BSA-αGal in ELLA's compared to that of H50V. In the H50N model, the asparagine side chain could contribute to binding through formation of a hydrogen bond with the iGb3 oligosaccharide but this would be formed with the terminal α1-3 linked galactose. Again it may therefore be the case that interactions with the second sugar moiety, or subsequent sugars residues in an oligosaccharide chain, have a greater stabilizing effect on oligosaccharide binding than the formation of additional interactions with the terminal galactose. This would account for the higher affinity exhibited by the H50Q protein for BSA-αGal compared to that of the H50N protein (FIG. 14B).

The Role of Gln53 and Asp52 in Modulating Carbohydrate Binding Activities—

Characterisation of the H50N, H50V and H50T proteins, and comparison with the carbohydrate binding activities of rPA-ILNmE6 (and rPA-ILNmC5), rPA-ILNmF3 and rPA-ILNmB4 respectively, clearly indicated that that additional Asp52 and Gln53 substitutions play a role in further modulating binding carbohydrate binding specificities and affinities. The Asp52 residue does not participate in forming productive interactions with bound iGb3 in the wild type PA-IL binding site (FIG. 1B) and so attention was first focused on the Gln53 residue. The H50N protein was used as a parental molecule into which 12 specific Gln53 substitutions were introduced. Characterisation of the resulting rPA-ILNm revealed only subtle differences in their binding properties and most simply exhibited weaker overall binding against the BSA glycoconjugates and AsT. Of particular interest were the results obtained for the H50N:Q53G protein. This protein exhibited slightly lower binding signals against AsT compared to H50N and slightly lower binding to the BSA-αGal glycoconjugate. This might be expected since a Q53G substitution would result in the loss of the productive interactions between the glutamine side chain and either bound lactose (FIG. 18D) or iGb3 (FIG. 19D). Despite this, the rPA-IL-NmE6 exhibits significantly stronger binding to AsT than either the H50N or H50N:Q53G proteins, generating signals approximately three fold greater, indicative of a higher affinity for glycoproteins displaying terminal β1,4-linked galactose. The rPA-ILNmE6 also exhibited greater selectivity for β-linked galactose over α-linked galactose generating signals nearly two fold lower than those observed for the H50N:Q53G protein. As the H50N:Q53G and rPA-ILNmE6 proteins only differ by a single D52N substitution, this additional substitution must be responsible for the enhanced affinity of the rPA-ILNmE6 protein for LacNAc and its greater selectivity. As the side chain of the substituted Asn52 resent in the rPA-ILNmE6 protein would not be expected to interact directly with the bound carbohydrate moiety, it is likely that the D52N substitution exerts its effect by inducing conformational changes in the carbohydrate binding site or by impacting on the organisation of water molecules within the binding pocket. Structural changes may result in a re-orientation of the Asn50 residue so that it interacts more favourably with glycans with LacNAc. In this respect, the substitution could potentially be synergistic with the Q53G substitution as the incorporation of a glycine residue would increase structural flexibility in the binding site.

Comparison of the binding properties of the H50V and H50T proteins with those of the rPA-ILNmF3 and rPA-ILNmB4 respectively implied that a Q53R substitution could promote binding to glycans with terminal α-linked galactose. To explore this, we introduced a Q53R substitution into the H50V protein to generate a H50V:Q53R double mutant that therefore only differed from the rPA-ILNmF3 protein by a single D52C substitution. ELLA analysis demonstrated that the resulting H50V:Q53R double mutant did bind to BSA-αGal and that its affinity for this glycoconjugate was comparable to that of the rPA-ILF3 protein (FIG. 16B). Interestingly the double mutant also displayed enhanced affinity for terminal β1,4-linked galactose compared to the parental H50V protein. It bound to AsT generating responses slightly greater than those of the rPA-ILNmF3 and actually generated significantly higher signals on BSA-LacNAc than either the H50V or rPA-ILNmF3 proteins. We subsequently introduced a Q53R substitution into the H50Q protein and the resulting H50Q:Q53R double mutant also displayed an enhanced affinity for the BSA-αGal glycoconjugate (FIG. 16B). However, more surprising was the fact that H50Q:Q53R double mutant did not bind to the BSA-LacNAc glycoconjugate (FIG. 16A). This clearly indicates that the impact of Gln53 substitutions on carbohydrate binding properties is dependent on the amino acid substitution at the His50 position. As none of the mutants we had constructed exhibited stronger binding to the BSA-αGal glycoconjugate than the parental rPA-ILN protein, we decided to introduce independent Q53R and Q53E substitutions into the rPA-ILN protein. As predicted, the resulting Q53R protein displayed an enhanced affinity for the BSA-αGal glycoconjugate and the Q53E protein was found to display a slightly higher relative affinity (FIG. 16B).

Final Conclusions—

This work successfully demonstrated the critical role that the His50 residue plays in dictating the specificity of the PA-IL protein. We clearly demonstrated that substitution of this residue alone was sufficient to significantly alter the carbohydrate binding properties of the protein. The observation that only specific amino acid substitutions promoted high affinity binding to glycans with LacNAc, and terminal β1,4-linked galactose, demonstrated that this was not simply due to alleviation of steric restraints that might be imposed by the His50 residue in the carbohydrate binding site of the protein. Through the use of structural models generated in silico, we were able to explore the potential structural basis for the carbohydrate binding specificities and affinities displayed by a number of rPA-ILNm proteins. We also demonstrated that both Gln53 and Asp53 substitutions played significant roles in further modulating the binding specificities and affinities of proteins. Predictive structural models could not explain the differences in the carbohydrate binding properties of the rPA-ILNmE6 protein compared to those of the H50N and H50N:Q53G proteins. These may be due to conformational changes in structure of the carbohydrate site induced by substitution of the Asn52 and Gln53 residues that could not be predicted and so verification of this will require future solving of the structure of these proteins. However, it is also clear from the results obtained that the final carbohydrate binding properties of rPA-ILNm proteins is the result of the combined effects of substitutions at His50, Asn52 and Gln53.

Many of the novel lectins generated in this study will be of use for glycoanalytical applications. While proteins like rPA-ILNmE6 would be of use for the detection of terminal β1,4 linked galactose, and LacNAc, others like the H50E protein could provide further biologically relevant information about a sample as binding is potentially dependant on the density and spatial distribution of glycans. The H50Q, with its dual specificity for terminal α-linked or β-linked galactose, could be used for general detection of terminal galactose while the Q53R and Q53E proteins, which display enhanced affinity for terminal α-linked galactose could be used to detect the presence of this potentially immunogenic sugar moiety. Inclusion of these novel recombinant prokaryotic lectins (RPL's) into any of the currently evolving glycoanalytical platforms, such as lectin microarrays, would significantly expand the utility of these platforms. If immobilized to solid support matrices, these RPL's may also facilitate enhanced glycoselective separations and the purification of glycoproteins and biotherapeutic molecules.

The invention is not limited to the embodiments described herein but can be amended or modified without departing from the scope of the present invention.

REFERENCES

1. Dwek, R. A. (1996). Glycobiology:toward understanding the function of sugars. *Chemical Reviews.* 96, 683-720
2. Drickamer, K., and Taylor, M. E. (2006) *Introduction To Glycobiology,* 2nd Edn Ed., Oxford University Press
3. Katrlik, J., Švitel, J., Gemeiner, P., Kožár, T., and Tkac, J. (2010). Glycan and lectin microarrays for glycomics and medicinal applications. *Medicinal Research Reviews.* 30, 394-418
4. Mislovičová, D., Gemeiner, P., Kozarova, A., and Kožár, T. (2009). Lectinomics I. Relevance of exogenous plant lectins in biomedical diagnostics. *Biologia.* 64, 1-19
5. Gemeiner, P., Mislovicová, D., Tkác, J., Svitel, J., Pätoprstý, V., Hrabárová, E., Kogan, G., and Kozár, T. (2009). Lectinomics: II. A highway to biomedical/clinical diagnostics. *Biotechnology Advances.* 27, 1-15
6. Ohtsubo, K., and Marth, J. D. (2006). Glycosylation in cellular mechanisms of health and disease. *Cell.* 126, 855-867
7. Chen, S., Zheng, T., Shortreed, M. R., Alexander, C., and Smith, L. M. (2007). Analysis of cell surface carbohydrate expression patterns in normal and tumorigenic human breast cell lines using lectin arrays. *Analytical Chemistry.* 79, 5698-5702
8. Dwek, M. V., Lacey, H. A., and Leathem, A. J. C. (1998). Breast cancer progression is associated with a reduction in the diversity of sialylated and neutral oligosaccharides. *Clinica Chimica Acta.* 271, 191-202
9. Zhao, J., Patwa, T. H., Qiu, W., Shedden, K., Hinderer, R., Misek, D. E., Anderson, M. A., Simeone, D. M., and Lubman, D. M. (2007). Glycoprotein microarrays with multi-lectin detection: unique lectin binding patterns as a tool for classifying normal, chronic pancreatitis and pancreatic cancer sera. *Journal of Proteome Research.* 6, 1864-1874
10. Dwek, M. V., Jenks, A., and Leathem, A. J. C. (2010). A sensitive assay to measure biomarker glycosylation demonstrates increased fucosylation of prostate specific antigen (PSA) in patients with prostate cancer compared with benign prostatic hyperplasia. *Clinica Chimica Acta.* 411, 1935-1939
11. Jefferis, R. (2009). Glycosylation as a strategy to improve antibody-based therapeutics. *Nat Rev Drug Discov.* 8, 226-234
12. Raju, T. S. (2008). Terminal sugars of Fc glycans influence antibody effector functions of IgGs. *Current Opinion in Immunology.* 20, 471-478
13. Burton, D. R., and Dwek, R. A. (2006). Sugar determines antibody activity. *Science.* 313, 627-628
14. Marth, J. D., and Grewal, P. K. (2008). Mammalian glycosylation in immunity. *Nat Rev Immunol.* 8, 874-887
15. Stancombe, P. R., Alexander, F. C. G., Ling, R., Matheson, M. A., Shone, C. C., and Chaddock, J. A. (2003). Isolation of the gene and large-scale expression and purification of recombinant *Erythrina cristagalli* lectin. *Protein Expression and Purification.* 30, 283-292
16. Oliveira, C., Teixeira, J. A., and Domingues, L. (2012). Recombinant lectins: an array of tailor-made glycan-interaction biosynthetic tools. *Critical Reviews in Biotechnology.* 0, 1-15
17. Imberty, A., Mitchell, E. P., and Wimmerova, M. (2005). Structural basis of high-affinity glycan recognition by bacterial and fungal lectins. *Carbohydrates and glycoconjugates/Biophysical methods.* 15, 525-534
18. Hu, D., Tateno, H., Kuno, A., Yabe, R., and Hirabayashi, J. (2012). Directed evolution of lectins with sugar-binding specificity for 6-sulfo-galactose. *Journal of Biological Chemistry.* 287, 20313-20320
19. Yabe, R., Suzuki, R., Kuno, A., Fujimoto, Z., Jigami, Y., and Hirabayashi, J. (2007). Tailoring a novel sialic acid-binding lectin from a ricin-B chain-like galactose-binding protein by natural evolution-mimicry. *J Biochem.* 141, 389-399
20. Romano, P. R., Mackay, A., Vong, M., deSa, J., Lamontagne, A., Comunale, M. A., Hafner, J., Block, T., Lec, R., and Mehta, A. (2011). Development of recombinant *Aleuria aurantia* lectins with altered binding specificities to fucosylated glycans. *Biochemical and Biophysical Research Communications.* 414, 84-89
21. Gilboa-Garber, N., and Ginsburg, V. (1982) *Pseudomonas aeruginosa* lectins. In. *Methods in Enzymology*, Academic Press
22. Imberty, A., Wimmerova, M., Mitchell, E. P., and Gilboa-Garber, N. (2004). Structures of the lectins from *Pseudomonas aeruginosa*: insights into the molecular basis for host glycan recognition. *Microbes and Infection.* 6, 221-228
23. Blanchard, B., Nurisso, A., Hollville, E., Tétaud, C., Wiels, J., Pokorná, M., Wimmerová, M., Varrot, A., and Imberty, A. (2008). Structural basis of the preferential binding for globo-series glycosphingolipids displayed by *Pseudomonas aeruginosa* Lectin I. *Journal of Molecular Biology.* 383, 837-853
24. Beck, A., Wagner-Rousset, E., Bussat, M.-C., Lokteff, M., and Klinguer-Hamour. (2008). Trends in glycosylation, glycoanalysis and glycoengineering of therapeutic antibodies and Fc-fusion proteins. *Current Pharmaceutical Biotechnology.* 9, 482-501
25. Arnold, K., Bordoli, L., Kopp, J., and Schwede, T. (2006). The SWISS-MODEL workspace: a web-based environment for protein structure homology modelling. *Bioinformatics.* 22, 195-201
26. McNicholas, S., Potterton, E., Wilson, K. S., and Noble, M. E. M. (2011). Presenting your structures: the CCP4mg molecular-graphics software. *Acta Crystallographica Section D.* 67, 386-394
27. Kirkeby, S., and Moe, D. (2002). Lectin interactions with α-galactosylated xenoantigens. *Xenotransplantation.* 9, 260-267
28. Chen, C. P., Song, S. C., Gilboa-Garber, N., Chang, K. S., and Wu, A. M. (1998). Studies on the binding site of the galactose-specific agglutinin PA-IL from *Pseudomonas aeruginosa. Glycobiology.* 8, 7-16
29. Cioci, G., Mitchell, E. P., Gautier, C., Wimmerova, M., Sudakevitz, D., Perez, S., Gilboa-Garber, N., and Imberty, A. (2003). Structural basis of calcium and galactose recognition by the lectin PA-IL of *Pseudomonas aeruginosa. FEBS Letters.* 555, 297-301
30. Litterer, L., and Schagat, T. (2007). Protein expression in less time: a short induction protocol for KRX. *Promega Notes.* 96, 20-21
31. Gilboa-Garber, N., and Sudakevitz, D. (1999). The hemagglutinating activities of *Pseudomonas aeruginosa* lectins PA-IL and PA-IIL exhibit opposite temperature profiles due to different receptor types. *FEMS Immunol Med Microbiol.* 25, 365-369
32. Hearty, S., Leonard, P., Quinn, J., and O'Kennedy, R. (2006). Production, characterisation and potential application of a novel monoclonal antibody for rapid identification of virulent *Listeria monocytogenes. Journal of Microbiological Methods.* 66, 294-312
33. Thompson, R., Creavin, A., O'Connell, M., O'Connor, B., and Clarke, P. (2011). Optimization of the enzyme-linked lectin assay for enhanced glycoprotein and glycoconjugate analysis. *Analytical Biochemistry.* 413, 114-122
34. Gilboa-Garber, N., Mizrahi, L., and Garber, N. (1972). Purification of the galactose-binding hemagglutinin of *Pseudomonas aeruginosa* by affinity column chromatography using sepharose. *FEBS Letters.* 28, 93-95
35. Wu, A. M., Song, S. C., Wu, J. H., and Kabat, E. A. (1995). Affinity of Bandeiraea (*Griffonia*) simplicifolia Lectin-I, Isolectin-B4 (BSI-B4) for Galα1-4Gal Ligand. *Biochemical and Biophysical Research Communications.* 216, 814-820
36. Iskratsch, T., Braun, A., Paschinger, K., and Wilson, I. B. H. (2009). Specificity analysis of lectins and antibodies using remodeled glycoproteins. *Analytical Biochemistry.* 386, 133-146
37. Trimble, R. B., and Atkinson, P. H. (1992). Structural heterogeneity in the $Man_{8-13}GlcNAc$ oligosaccharides from log-phase Saccharomyces yeast: a one- and two-dimensional 1H NMR spectroscopic study. *Glycobiology.* 2, 57-75
38. Wu, A., Wu, J., Tsai, M.-S., Yang, Z., Sharon, N., and Herp, A. (2007). Differential affinities of *Erythrina cristagalli* lectin (ECL) toward monosaccharides and polyvalent mammalian structural units. *Glycoconjugate Journal.* 24, 591-604
39. Wu, A., Lisowska, E., Duk, M., and Yang, Z. (2008). Lectins as tools in glycoconjugate research. *Glycoconjugate Journal.* 26, 899-913
40. Shields, R. L., Lai, J., Keck, R., O'Connell, L. Y., Hong, K., Meng, Y. G., Weikert, S. H. A., and Presta, L. G. (2002). Lack of fucose on human IgG1 N-linked oligosaccharide improves binding to human FcγRIII and antibody-dependent cellular toxicity. *Journal of Biological Chemistry.* 277, 26733-26740
41. Qiu, R., and Regnier, F. E. (2005). Use of multidimensional lectin affinity chromatography in differential glycoproteomics. *Anal. Chem.* 77, 2802-2809

42. Geyer, H., and Geyer, R. (2006). Strategies for analysis of glycoprotein glycosylation. *Biochimica et Biophysica Acta (BBA)—Proteins & Proteomics.* 1764, 1853-1869

43. Yang, Z., and Hancock, W. S. (2005). Monitoring glycosylation pattern changes of glycoproteins using multi-lectin affinity chromatography. *Journal of Chromatography A.* 1070, 57-64

44. Walsh, G., and Jefferis, R. (2006). Post-translational modifications in the context of therapeutic proteins. *Nat Biotech.* 24, 1241-1252

45. Walsh, G. (2006). Biopharmaceutical benchmarks 2006. *Nat Biotech.* 24, 769-776

46. Sinclair, A. M., and Elliott, S. (2005). Glycoengineering: The effect of glycosylation on the properties of therapeutic proteins. *Journal of Pharmaceutical Sciences.* 94, 1626-1635

47. Werner, R. G., Kopp, K., and Schlueter, M. (2007). Glycosylation of therapeutic proteins in different production systems. *Acta Paediatrica.* 96, 17-22

48. Kim, H. J., Lee, S. J., and Kim, H.-J. (2008). Antibody-based enzyme-linked lectin assay (ABELLA) for the sialylated recombinant human erythropoietin present in culture supernatant. *Journal of Pharmaceutical and Biomedical Analysis.* 48, 716-721

49. Kobata, A. (2000). A journey to the world of glycobiology. *Glycoconjugate Journal.* 17, 443

50. Xu, W., Chen, J., Yamasaki, G., Murphy, J., and Mei, B. (2010). Lectin Binding Assays for In-Process Monitoring of Sialylation in Protein Production. *Molecular Biotechnology.* 45, 248-256

51. Scallon, B. J., Tam, S. H., McCarthy, S. G., Cai, A. N., and Raju, T. S. (2007). Higher levels of sialylated Fc glycans in immunoglobulin G molecules can adversely impact functionality. *Molecular Immunology.* 44, 1524-1534

The invention claimed is:

1. A peptide analogue of PA-IL of SEQ ID NO: 1, wherein the peptide analogue comprises an amino acid substitution at positions 50, 52 and 53, wherein the amino acid substitution at position 50 is Asn, the amino acid substitution at position 52 is Asn; and the amino acid substitution at position 53 is Gly.

2. A method for detecting changes in the glycosylation of a glycoprotein, a glycoconjugate or a cell surface, the method comprising qualitatively or quantitatively assessing terminal galactosylation by exposing the glycoprotein, the glycoconjugate or the cell surface to the peptide analogue of claim 1, determining affinity of the glycoprotein, the glycoconjugate or the cell surface for the peptide, and comparing the affinity to a reference, wherein a difference in the affinity of the glycoprotein, the glycoconjugate or the cell surface relative to the reference indicates a change in glycosylation of the glycoprotein, the glycoconjugate or the cell surface.

3. A method of separating and isolating biomolecules, cells or a combination thereof, comprising a glycoprotein or a glycoconjugate, the method comprising contacting the peptide analogue of claim 1 with a solution or suspension containing the biomolecules, cells or the combination thereof; and separating the biomolecules, the cells or the combination thereof not bound by the peptide analogue.

* * * * *

SEQUENCE LISTING

```
<160> NUMBER OF SEQ ID NOS: 94

<210> SEQ ID NO 1
<211> LENGTH: 134
<212> TYPE: PRT
<213> ORGANISM: Artificial Sequence
<220> FEATURE:
<223> OTHER INFORMATION: rPA-ILN

<400> SEQUENCE: 1

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu His Pro
    50                  55                  60

Asp Gln Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 2
<211> LENGTH: 134
<212> TYPE: PRT
<213> ORGANISM: Artificial Sequence
<220> FEATURE:
<223> OTHER INFORMATION: rPA-ILNma8 (H50L:D52H:Q53R)

<400> SEQUENCE: 2

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45
```

```
Tyr Gly Pro Thr Gln Lys Trp Gly Pro Gln Gly Asp Arg Glu Leu Pro
    50                  55                  60

His Arg Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 3
<211> LENGTH: 134
<212> TYPE: PRT
<213> ORGANISM: Artificial Sequence
<220> FEATURE:
<223> OTHER INFORMATION: rPA-ILNmB4(H50T:D52N:Q53R)

<400> SEQUENCE: 3

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Thr Pro
    50                  55                  60

Asn Arg Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 4
<211> LENGTH: 134
<212> TYPE: PRT
<213> ORGANISM: Artificial Sequence
<220> FEATURE:
<223> OTHER INFORMATION: rPA-ILNmB10(H50V:D52C:Q53E)

<400> SEQUENCE: 4

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Val Pro
    50                  55                  60

Cys Glu Gly Leu Ile Cys His Asp Ala Phe Cys Gly Ala Leu Val Met
65                  70                  75                  80
```

```
Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 5
<211> LENGTH: 134
<212> TYPE: PRT
<213> ORGANISM: Artificial Sequence
<220> FEATURE:
<223> OTHER INFORMATION: rPA-ILNmC5 (H50N:D52T:Q53S)

<400> SEQUENCE: 5

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Thr Ser Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 6
<211> LENGTH: 134
<212> TYPE: PRT
<213> ORGANISM: Artificial Sequence
<220> FEATURE:
<223> OTHER INFORMATION: rPA-ILNmE6 (H50N:D52N:Q53G)

<400> SEQUENCE: 6

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asn Gly Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
```

```
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 7
<211> LENGTH: 134
<212> TYPE: PRT
<213> ORGANISM: Artificial Sequence
<220> FEATURE:
<223> OTHER INFORMATION: rPA-ILNmE12 (H50G:D52C:Q53R)

<400> SEQUENCE: 7

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Gly Pro
    50                  55                  60

Cys Arg Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 8
<211> LENGTH: 134
<212> TYPE: PRT
<213> ORGANISM: Artificial Sequence
<220> FEATURE:
<223> OTHER INFORMATION: rPA-ILNmF3(H50V:D52C:Q53R)

<400> SEQUENCE: 8

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Val Pro
    50                  55                  60

Cys Arg Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125
```

-continued

```
Ile Gly Lys Asp Gln Ser
    130


<210> SEQ ID NO 9
<211> LENGTH: 134
<212> TYPE: PRT
<213> ORGANISM: Artificial Sequence
<220> FEATURE:
<223> OTHER INFORMATION: rPA-ILNmF6(H50P:D52R:Q53L)

<400> SEQUENCE: 9

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Pro Pro
    50                  55                  60

Arg Leu Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 10
<211> LENGTH: 134
<212> TYPE: PRT
<213> ORGANISM: Artificial Sequence
<220> FEATURE:
<223> OTHER INFORMATION: rPA-ILNmG3(H50V:D52N:Q53N)

<400> SEQUENCE: 10

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Val Pro
    50                  55                  60

Asn Asn Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 11
```

<211> LENGTH: 134
<212> TYPE: PRT
<213> ORGANISM: Artificial Sequence
<220> FEATURE:
<223> OTHER INFORMATION: H50A

<400> SEQUENCE: 11

Met Arg Gly Ser His His His His His His Gly Ser Met Ala Trp Lys
1 5 10 15

Gly Glu Val Leu Ala Asn Asn Glu Ala Gly Gln Val Thr Ser Ile Ile
20 25 30

Tyr Asn Pro Gly Asp Val Ile Thr Ile Val Ala Ala Gly Trp Ala Ser
35 40 45

Tyr Gly Pro Thr Gln Lys Trp Gly Pro Gln Gly Asp Arg Glu Ala Pro
50 55 60

Asp Gln Gly Leu Ile Cys His Asp Ala Phe Cys Gly Ala Leu Val Met
65 70 75 80

Lys Ile Gly Asn Ser Gly Thr Ile Pro Val Asn Thr Gly Leu Phe Arg
85 90 95

Trp Val Ala Pro Asn Asn Val Gln Gly Ala Ile Thr Leu Ile Tyr Asn
100 105 110

Asp Val Pro Gly Thr Tyr Gly Asn Asn Ser Gly Ser Phe Ser Val Asn
115 120 125

Ile Gly Lys Asp Gln Ser
130

<210> SEQ ID NO 12
<211> LENGTH: 134
<212> TYPE: PRT
<213> ORGANISM: Artificial Sequence
<220> FEATURE:
<223> OTHER INFORMATION: H50V

<400> SEQUENCE: 12

Met Arg Gly Ser His His His His His His Gly Ser Met Ala Trp Lys
1 5 10 15

Gly Glu Val Leu Ala Asn Asn Glu Ala Gly Gln Val Thr Ser Ile Ile
20 25 30

Tyr Asn Pro Gly Asp Val Ile Thr Ile Val Ala Ala Gly Trp Ala Ser
35 40 45

Tyr Gly Pro Thr Gln Lys Trp Gly Pro Gln Gly Asp Arg Glu Val Pro
50 55 60

Asp Gln Gly Leu Ile Cys His Asp Ala Phe Cys Gly Ala Leu Val Met
65 70 75 80

Lys Ile Gly Asn Ser Gly Thr Ile Pro Val Asn Thr Gly Leu Phe Arg
85 90 95

Trp Val Ala Pro Asn Asn Val Gln Gly Ala Ile Thr Leu Ile Tyr Asn
100 105 110

Asp Val Pro Gly Thr Tyr Gly Asn Asn Ser Gly Ser Phe Ser Val Asn
115 120 125

Ile Gly Lys Asp Gln Ser
130

<210> SEQ ID NO 13
<211> LENGTH: 134
<212> TYPE: PRT
<213> ORGANISM: Artificial Sequence
<220> FEATURE:
<223> OTHER INFORMATION: H50L -continued

<400> SEQUENCE: 13

```
Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Leu Pro
    50                  55                  60

Asp Gln Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130
```

<210> SEQ ID NO 14
<211> LENGTH: 134
<212> TYPE: PRT
<213> ORGANISM: Artificial Sequence
<220> FEATURE:
<223> OTHER INFORMATION: H50F

<400> SEQUENCE: 14

```
Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Phe Pro
    50                  55                  60

Asp Gln Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130
```

<210> SEQ ID NO 15
<211> LENGTH: 134
<212> TYPE: PRT
<213> ORGANISM: Artificial Sequence
<220> FEATURE:
<223> OTHER INFORMATION: H50P

<400> SEQUENCE: 15

```
Met Arg Gly Ser His His His His His His Gly Ser Met Ala Trp Lys
1               5                   10                  15
```

Gly Glu Val Leu Ala Asn Asn Glu Ala Gly Gln Val Thr Ser Ile Ile
20 25 30

Tyr Asn Pro Gly Asp Val Ile Thr Ile Val Ala Ala Gly Trp Ala Ser
35 40 45

Tyr Gly Pro Thr Gln Lys Trp Gly Pro Gln Gly Asp Arg Glu Pro Pro
50 55 60

Asp Gln Gly Leu Ile Cys His Asp Ala Phe Cys Gly Ala Leu Val Met
65 70 75 80

Lys Ile Gly Asn Ser Gly Thr Ile Pro Val Asn Thr Gly Leu Phe Arg
85 90 95

Trp Val Ala Pro Asn Asn Val Gln Gly Ala Ile Thr Leu Ile Tyr Asn
100 105 110

Asp Val Pro Gly Thr Tyr Gly Asn Asn Ser Gly Ser Phe Ser Val Asn
115 120 125

Ile Gly Lys Asp Gln Ser
130

<210> SEQ ID NO 16
<211> LENGTH: 134
<212> TYPE: PRT
<213> ORGANISM: Artificial Sequence
<220> FEATURE:
<223> OTHER INFORMATION: H50S

<400> SEQUENCE: 16

Met Arg Gly Ser His His His His His His Gly Ser Met Ala Trp Lys
1 5 10 15

Gly Glu Val Leu Ala Asn Asn Glu Ala Gly Gln Val Thr Ser Ile Ile
20 25 30

Tyr Asn Pro Gly Asp Val Ile Thr Ile Val Ala Ala Gly Trp Ala Ser
35 40 45

Tyr Gly Pro Thr Gln Lys Trp Gly Pro Gln Gly Asp Arg Glu Ser Pro
50 55 60

Asp Gln Gly Leu Ile Cys His Asp Ala Phe Cys Gly Ala Leu Val Met
65 70 75 80

Lys Ile Gly Asn Ser Gly Thr Ile Pro Val Asn Thr Gly Leu Phe Arg
85 90 95

Trp Val Ala Pro Asn Asn Val Gln Gly Ala Ile Thr Leu Ile Tyr Asn
100 105 110

Asp Val Pro Gly Thr Tyr Gly Asn Asn Ser Gly Ser Phe Ser Val Asn
115 120 125

Ile Gly Lys Asp Gln Ser
130

<210> SEQ ID NO 17
<211> LENGTH: 134
<212> TYPE: PRT
<213> ORGANISM: Artificial Sequence
<220> FEATURE:
<223> OTHER INFORMATION: H50T

<400> SEQUENCE: 17

Met Arg Gly Ser His His His His His His Gly Ser Met Ala Trp Lys
1 5 10 15

Gly Glu Val Leu Ala Asn Asn Glu Ala Gly Gln Val Thr Ser Ile Ile
20 25 30

Tyr Asn Pro Gly Asp Val Ile Thr Ile Val Ala Ala Gly Trp Ala Ser

```
        35                  40                  45

Tyr Gly Pro Thr Gln Lys Trp Gly Pro Gln Gly Asp Arg Glu Thr Pro
    50                  55                  60

Asp Gln Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 18
<211> LENGTH: 134
<212> TYPE: PRT
<213> ORGANISM: Artificial Sequence
<220> FEATURE:
<223> OTHER INFORMATION: H50N

<400> SEQUENCE: 18

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asp Gln Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 19
<211> LENGTH: 134
<212> TYPE: PRT
<213> ORGANISM: Artificial Sequence
<220> FEATURE:
<223> OTHER INFORMATION: H50Q

<400> SEQUENCE: 19

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Gln Pro
    50                  55                  60
```

Asp Gln Gly Leu Ile Cys His Asp Ala Phe Cys Gly Ala Leu Val Met
65 70 75 80

Lys Ile Gly Asn Ser Gly Thr Ile Pro Val Asn Thr Gly Leu Phe Arg
85 90 95

Trp Val Ala Pro Asn Asn Val Gln Gly Ala Ile Thr Leu Ile Tyr Asn
100 105 110

Asp Val Pro Gly Thr Tyr Gly Asn Asn Ser Gly Ser Phe Ser Val Asn
115 120 125

Ile Gly Lys Asp Gln Ser
130

<210> SEQ ID NO 20
<211> LENGTH: 134
<212> TYPE: PRT
<213> ORGANISM: Artificial Sequence
<220> FEATURE:
<223> OTHER INFORMATION: H50D

<400> SEQUENCE: 20

Met Arg Gly Ser His His His His His His Gly Ser Met Ala Trp Lys
1 5 10 15

Gly Glu Val Leu Ala Asn Asn Glu Ala Gly Gln Val Thr Ser Ile Ile
20 25 30

Tyr Asn Pro Gly Asp Val Ile Thr Ile Val Ala Ala Gly Trp Ala Ser
35 40 45

Tyr Gly Pro Thr Gln Lys Trp Gly Pro Gln Gly Asp Arg Glu Asp Pro
50 55 60

Asp Gln Gly Leu Ile Cys His Asp Ala Phe Cys Gly Ala Leu Val Met
65 70 75 80

Lys Ile Gly Asn Ser Gly Thr Ile Pro Val Asn Thr Gly Leu Phe Arg
85 90 95

Trp Val Ala Pro Asn Asn Val Gln Gly Ala Ile Thr Leu Ile Tyr Asn
100 105 110

Asp Val Pro Gly Thr Tyr Gly Asn Asn Ser Gly Ser Phe Ser Val Asn
115 120 125

Ile Gly Lys Asp Gln Ser
130

<210> SEQ ID NO 21
<211> LENGTH: 134
<212> TYPE: PRT
<213> ORGANISM: Artificial Sequence
<220> FEATURE:
<223> OTHER INFORMATION: H50E

<400> SEQUENCE: 21

Met Arg Gly Ser His His His His His His Gly Ser Met Ala Trp Lys
1 5 10 15

Gly Glu Val Leu Ala Asn Asn Glu Ala Gly Gln Val Thr Ser Ile Ile
20 25 30

Tyr Asn Pro Gly Asp Val Ile Thr Ile Val Ala Ala Gly Trp Ala Ser
35 40 45

Tyr Gly Pro Thr Gln Lys Trp Gly Pro Gln Gly Asp Arg Glu Glu Pro
50 55 60

Asp Gln Gly Leu Ile Cys His Asp Ala Phe Cys Gly Ala Leu Val Met
65 70 75 80

Lys Ile Gly Asn Ser Gly Thr Ile Pro Val Asn Thr Gly Leu Phe Arg
85 90 95

```
Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 22
<211> LENGTH: 134
<212> TYPE: PRT
<213> ORGANISM: Artificial Sequence
<220> FEATURE:
<223> OTHER INFORMATION: H50K

<400> SEQUENCE: 22

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Lys Pro
    50                  55                  60

Asp Gln Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 23
<211> LENGTH: 134
<212> TYPE: PRT
<213> ORGANISM: Artificial Sequence
<220> FEATURE:
<223> OTHER INFORMATION: H50R

<400> SEQUENCE: 23

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Arg Pro
    50                  55                  60

Asp Gln Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
```

```
        115                 120                 125

Ile Gly Lys Asp Gln Ser
    130


<210> SEQ ID NO 24
<211> LENGTH: 134
<212> TYPE: PRT
<213> ORGANISM: Artificial Sequence
<220> FEATURE:
<223> OTHER INFORMATION: H50N:Q53A

<400> SEQUENCE: 24

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asp Ala Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 25
<211> LENGTH: 134
<212> TYPE: PRT
<213> ORGANISM: Artificial Sequence
<220> FEATURE:
<223> OTHER INFORMATION: H50N:Q53V

<400> SEQUENCE: 25

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asp Val Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130
```

<210> SEQ ID NO 26
<211> LENGTH: 134
<212> TYPE: PRT
<213> ORGANISM: Artificial Sequence
<220> FEATURE:
<223> OTHER INFORMATION: H50N:Q53L

<400> SEQUENCE: 26

```
Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asp Leu Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130
```

<210> SEQ ID NO 27
<211> LENGTH: 134
<212> TYPE: PRT
<213> ORGANISM: Artificial Sequence
<220> FEATURE:
<223> OTHER INFORMATION: H50N:Q53G

<400> SEQUENCE: 27

```
Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asp Gly Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130
```

<210> SEQ ID NO 28
<211> LENGTH: 134
<212> TYPE: PRT
<213> ORGANISM: Artificial Sequence

```
<220> FEATURE:
<223> OTHER INFORMATION: H50N:Q53Y

<400> SEQUENCE: 28

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asp Tyr Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 29
<211> LENGTH: 134
<212> TYPE: PRT
<213> ORGANISM: Artificial Sequence
<220> FEATURE:
<223> OTHER INFORMATION: H50N:Q53N

<400> SEQUENCE: 29

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asp Asn Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 30
<211> LENGTH: 134
<212> TYPE: PRT
<213> ORGANISM: Artificial Sequence
<220> FEATURE:
<223> OTHER INFORMATION: H50N:Q53D

<400> SEQUENCE: 30
```

-continued

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asp Asp Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130

<210> SEQ ID NO 31
<211> LENGTH: 134
<212> TYPE: PRT
<213> ORGANISM: Artificial Sequence
<220> FEATURE:
<223> OTHER INFORMATION: H50N:Q53E

<400> SEQUENCE: 31

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asp Glu Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130

<210> SEQ ID NO 32
<211> LENGTH: 134
<212> TYPE: PRT
<213> ORGANISM: Artificial Sequence
<220> FEATURE:
<223> OTHER INFORMATION: H50N:Q53K

<400> SEQUENCE: 32

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

```
Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asp Lys Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 33
<211> LENGTH: 134
<212> TYPE: PRT
<213> ORGANISM: Artificial Sequence
<220> FEATURE:
<223> OTHER INFORMATION: H50N:Q53R

<400> SEQUENCE: 33

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
    50                  55                  60

Asp Arg Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 34
<211> LENGTH: 134
<212> TYPE: PRT
<213> ORGANISM: Artificial Sequence
<220> FEATURE:
<223> OTHER INFORMATION: H50N:Q53H

<400> SEQUENCE: 34

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Asn Pro
```

```
    50                  55                  60

Asp His Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 35
<211> LENGTH: 134
<212> TYPE: PRT
<213> ORGANISM: Artificial Sequence
<220> FEATURE:
<223> OTHER INFORMATION: H50V:Q53R

<400> SEQUENCE: 35

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Val Pro
    50                  55                  60

Asp Arg Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 36
<211> LENGTH: 134
<212> TYPE: PRT
<213> ORGANISM: Artificial Sequence
<220> FEATURE:
<223> OTHER INFORMATION: H50V:Q53K

<400> SEQUENCE: 36

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Val Pro
    50                  55                  60

Asp Lys Gly Leu Ile Cys His Asp Ala Phe Cys Gly Ala Leu Val Met
65                  70                  75                  80
```

-continued

```
Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 37
<211> LENGTH: 134
<212> TYPE: PRT
<213> ORGANISM: Artificial Sequence
<220> FEATURE:
<223> OTHER INFORMATION: H50Q:Q53R

<400> SEQUENCE: 37

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Gln Pro
    50                  55                  60

Asp Arg Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 38
<211> LENGTH: 134
<212> TYPE: PRT
<213> ORGANISM: Artificial Sequence
<220> FEATURE:
<223> OTHER INFORMATION: H50Q:Q53K

<400> SEQUENCE: 38

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu Gln Pro
    50                  55                  60

Asp Lys Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110
```

```
Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 39
<211> LENGTH: 134
<212> TYPE: PRT
<213> ORGANISM: Artificial Sequence
<220> FEATURE:
<223> OTHER INFORMATION: Q53R

<400> SEQUENCE: 39

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu His Pro
    50                  55                  60

Asp Arg Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 40
<211> LENGTH: 134
<212> TYPE: PRT
<213> ORGANISM: Artificial Sequence
<220> FEATURE:
<223> OTHER INFORMATION: Q53K

<400> SEQUENCE: 40

Met Arg Gly Ser His His His His His His Gly Ser Met Ala Trp Lys
1               5                   10                  15

Gly Glu Val Leu Ala Asn Asn Glu Ala Gly Gln Val Thr Ser Ile Ile
            20                  25                  30

Tyr Asn Pro Gly Asp Val Ile Thr Ile Val Ala Ala Gly Trp Ala Ser
        35                  40                  45

Tyr Gly Pro Thr Gln Lys Trp Gly Pro Gln Gly Asp Arg Glu His Pro
    50                  55                  60

Asp Lys Gly Leu Ile Cys His Asp Ala Phe Cys Gly Ala Leu Val Met
65                  70                  75                  80

Lys Ile Gly Asn Ser Gly Thr Ile Pro Val Asn Thr Gly Leu Phe Arg
                85                  90                  95

Trp Val Ala Pro Asn Asn Val Gln Gly Ala Ile Thr Leu Ile Tyr Asn
            100                 105                 110

Asp Val Pro Gly Thr Tyr Gly Asn Asn Ser Gly Ser Phe Ser Val Asn
        115                 120                 125

Ile Gly Lys Asp Gln Ser
```

130

<210> SEQ ID NO 41
<211> LENGTH: 134
<212> TYPE: PRT
<213> ORGANISM: Artificial Sequence
<220> FEATURE:
<223> OTHER INFORMATION: Q53K

<400> SEQUENCE: 41

Met Arg Gly Ser His His His His His His Gly Ser Met Ala Trp Lys
1 5 10 15

Gly Glu Val Leu Ala Asn Asn Glu Ala Gly Gln Val Thr Ser Ile Ile
20 25 30

Tyr Asn Pro Gly Asp Val Ile Thr Ile Val Ala Ala Gly Trp Ala Ser
35 40 45

Tyr Gly Pro Thr Gln Lys Trp Gly Pro Gln Gly Asp Arg Glu His Pro
50 55 60

Asp Glu Gly Leu Ile Cys His Asp Ala Phe Cys Gly Ala Leu Val Met
65 70 75 80

Lys Ile Gly Asn Ser Gly Thr Ile Pro Val Asn Thr Gly Leu Phe Arg
85 90 95

Trp Val Ala Pro Asn Asn Val Gln Gly Ala Ile Thr Leu Ile Tyr Asn
100 105 110

Asp Val Pro Gly Thr Tyr Gly Asn Asn Ser Gly Ser Phe Ser Val Asn
115 120 125

Ile Gly Lys Asp Gln Ser
130

<210> SEQ ID NO 42
<211> LENGTH: 29
<212> TYPE: DNA
<213> ORGANISM: Artificial Sequence
<220> FEATURE:
<223> OTHER INFORMATION: primer

<400> SEQUENCE: 42
aaaaggatcc atggcttgga aaggtgagg 29

<210> SEQ ID NO 43
<211> LENGTH: 31
<212> TYPE: DNA
<213> ORGANISM: Artificial Sequence
<220> FEATURE:
<223> OTHER INFORMATION: primer

<400> SEQUENCE: 43
aaaaccatgg cttggaaagg tgaggttctg g 31

<210> SEQ ID NO 44
<211> LENGTH: 34
<212> TYPE: DNA
<213> ORGANISM: Artificial Sequence
<220> FEATURE:
<223> OTHER INFORMATION: primer

<400> SEQUENCE: 44
aaaaaagctt tcacgactga tcctttccaa tatt 34

<210> SEQ ID NO 45
<211> LENGTH: 36
<212> TYPE: DNA

-continued

<213> ORGANISM: Artificial Sequence
<220> FEATURE:
<223> OTHER INFORMATION: primer

<400> SEQUENCE: 45
aaaaagatct cgactgatcc tttccaatat tgacac 36

<210> SEQ ID NO 46
<211> LENGTH: 32
<212> TYPE: DNA
<213> ORGANISM: Artificial Sequence
<220> FEATURE:
<223> OTHER INFORMATION: primer

<400> SEQUENCE: 46
cgttttgtgg tgcgctggtc atgaagattg gc 32

<210> SEQ ID NO 47
<211> LENGTH: 46
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(25)
<223> OTHER INFORMATION: n is a, c, g, or t
<220> FEATURE:
<221> NAME/KEY: misc_feature
<222> LOCATION: (29)..(31)
<223> OTHER INFORMATION: n is a, c, g, or t

<400> SEQUENCE: 47
cgtcgtggca gatcagcccn nnnnncggnn nctcccgatc gccctg 46

<210> SEQ ID NO 48
<211> LENGTH: 32
<212> TYPE: DNA
<213> ORGANISM: Artificial Sequence
<220> FEATURE:
<223> OTHER INFORMATION: primer

<400> SEQUENCE: 48
cgttttgtgg tgcgctggtc atgaagattg gc 32

<210> SEQ ID NO 49
<211> LENGTH: 46
<212> TYPE: DNA
<213> ORGANISM: Artificial Sequence
<220> FEATURE:
<223> OTHER INFORMATION: primer

<400> SEQUENCE: 49
cgtcgtggca gatcagccct tggtccggtg cctcccgatc gccctg 46

<210> SEQ ID NO 50
<211> LENGTH: 46
<212> TYPE: DNA
<213> ORGANISM: Artificial Sequence
<220> FEATURE:
<223> OTHER INFORMATION: primer

<400> SEQUENCE: 50
cgtcgtggca gatcagccct tggtccggta cctcccgatc gccctg 46

<210> SEQ ID NO 51
<211> LENGTH: 46

-continued

<212> TYPE: DNA
<213> ORGANISM: Artificial Sequence
<220> FEATURE:
<223> OTHER INFORMATION: primer

<400> SEQUENCE: 51
cgtcgtggca gatcagccct tggtccggca gctcccgatc gccctg 46

<210> SEQ ID NO 52
<211> LENGTH: 46
<212> TYPE: DNA
<213> ORGANISM: Artificial Sequence
<220> FEATURE:
<223> OTHER INFORMATION: primer

<400> SEQUENCE: 52
cgtcgtggca gatcagccct tggtccggaa actcccgatc gccctg 46

<210> SEQ ID NO 53
<211> LENGTH: 46
<212> TYPE: DNA
<213> ORGANISM: Artificial Sequence
<220> FEATURE:
<223> OTHER INFORMATION: primer

<400> SEQUENCE: 53
cgtcgtggca gatcagccct tggtccggcg gctcccgatc gccctg 46

<210> SEQ ID NO 54
<211> LENGTH: 46
<212> TYPE: DNA
<213> ORGANISM: Artificial Sequence
<220> FEATURE:
<223> OTHER INFORMATION: primer

<400> SEQUENCE: 54
cgtcgtggca gatcagccct tggtccggag actcccgatc gccctg 46

<210> SEQ ID NO 55
<211> LENGTH: 46
<212> TYPE: DNA
<213> ORGANISM: Artificial Sequence
<220> FEATURE:
<223> OTHER INFORMATION: primer

<400> SEQUENCE: 55
cgtcgtggca gatcagccct tggtccgggg tctcccgatc gccctg 46

<210> SEQ ID NO 56
<211> LENGTH: 46
<212> TYPE: DNA
<213> ORGANISM: Artificial Sequence
<220> FEATURE:
<223> OTHER INFORMATION: primer

<400> SEQUENCE: 56
cgtcgtggca gatcagccct tggtccggat tctcccgatc gccctg 46

<210> SEQ ID NO 57
<211> LENGTH: 46
<212> TYPE: DNA
<213> ORGANISM: Artificial Sequence
<220> FEATURE:
<223> OTHER INFORMATION: primer

<400> SEQUENCE: 57

-continued

```
cgtcgtggca gatcagccct tggtccggtt gctcccgatc gccctg                    46


<210> SEQ ID NO 58
<211> LENGTH: 46
<212> TYPE: DNA
<213> ORGANISM: Artificial Sequence
<220> FEATURE:
<223> OTHER INFORMATION: primer

<400> SEQUENCE: 58

cgtcgtggca gatcagccct tggtccggat cctcccgatc gccctg                    46


<210> SEQ ID NO 59
<211> LENGTH: 46
<212> TYPE: DNA
<213> ORGANISM: Artificial Sequence
<220> FEATURE:
<223> OTHER INFORMATION: primer

<400> SEQUENCE: 59

cgtcgtggca gatcagccct tggtccggtt cctcccgatc gccctg                    46


<210> SEQ ID NO 60
<211> LENGTH: 46
<212> TYPE: DNA
<213> ORGANISM: Artificial Sequence
<220> FEATURE:
<223> OTHER INFORMATION: primer

<400> SEQUENCE: 60

cgtcgtggca gatcagccct tggtccggtt tctcccgatc gccctg                    46


<210> SEQ ID NO 61
<211> LENGTH: 46
<212> TYPE: DNA
<213> ORGANISM: Artificial Sequence
<220> FEATURE:
<223> OTHER INFORMATION: primer

<400> SEQUENCE: 61

cgtcgtggca gatcagccct tggtccggtc tctcccgatc gccctg                    46


<210> SEQ ID NO 62
<211> LENGTH: 46
<212> TYPE: DNA
<213> ORGANISM: Artificial Sequence
<220> FEATURE:
<223> OTHER INFORMATION: primer

<400> SEQUENCE: 62

cgtcgtggca gatcagcccc gcatccgggt tctcccgatc gccctg                    46


<210> SEQ ID NO 63
<211> LENGTH: 46
<212> TYPE: DNA
<213> ORGANISM: Artificial Sequence
<220> FEATURE:
<223> OTHER INFORMATION: primer

<400> SEQUENCE: 63

cgtcgtggca gatcagcccc acatccgggt tctcccgatc gccctg                    46


<210> SEQ ID NO 64
<211> LENGTH: 46
<212> TYPE: DNA
<213> ORGANISM: Artificial Sequence
```

<220> FEATURE:
<223> OTHER INFORMATION: primer

<400> SEQUENCE: 64
cgtcgtggca gatcagcccc agatccgggt tctcccgatc gccctg 46

<210> SEQ ID NO 65
<211> LENGTH: 46
<212> TYPE: DNA
<213> ORGANISM: Artificial Sequence
<220> FEATURE:
<223> OTHER INFORMATION: primer

<400> SEQUENCE: 65
cgtcgtggca gatcagcccg ccatccgggt tctcccgatc gccctg 46

<210> SEQ ID NO 66
<211> LENGTH: 46
<212> TYPE: DNA
<213> ORGANISM: Artificial Sequence
<220> FEATURE:
<223> OTHER INFORMATION: primer

<400> SEQUENCE: 66
cgtcgtggca gatcagcccg ctatccgggt tctcccgatc gccctg 46

<210> SEQ ID NO 67
<211> LENGTH: 46
<212> TYPE: DNA
<213> ORGANISM: Artificial Sequence
<220> FEATURE:
<223> OTHER INFORMATION: primer

<400> SEQUENCE: 67
cgtcgtggca gatcagccca taatccgggt tctcccgatc gccctg 46

<210> SEQ ID NO 68
<211> LENGTH: 46
<212> TYPE: DNA
<213> ORGANISM: Artificial Sequence
<220> FEATURE:
<223> OTHER INFORMATION: primer

<400> SEQUENCE: 68
cgtcgtggca gatcagcccg ttatccgggt tctcccgatc gccctg 46

<210> SEQ ID NO 69
<211> LENGTH: 46
<212> TYPE: DNA
<213> ORGANISM: Artificial Sequence
<220> FEATURE:
<223> OTHER INFORMATION: primer

<400> SEQUENCE: 69
cgtcgtggca gatcagccca tcatccgggt tctcccgatc gccctg 46

<210> SEQ ID NO 70
<211> LENGTH: 46
<212> TYPE: DNA
<213> ORGANISM: Artificial Sequence
<220> FEATURE:
<223> OTHER INFORMATION: primer

<400> SEQUENCE: 70
cgtcgtggca gatcagccct tcatccgggt tctcccgatc gccctg 46

<210> SEQ ID NO 71
<211> LENGTH: 46
<212> TYPE: DNA
<213> ORGANISM: Artificial Sequence
<220> FEATURE:
<223> OTHER INFORMATION: primer

<400> SEQUENCE: 71
cgtcgtggca gatcagccct ttatccgggt tctcccgatc gccctg 46

<210> SEQ ID NO 72
<211> LENGTH: 46
<212> TYPE: DNA
<213> ORGANISM: Artificial Sequence
<220> FEATURE:
<223> OTHER INFORMATION: primer

<400> SEQUENCE: 72
cgtcgtggca gatcagcccg cgatccgggt tctcccgatc gccctg 46

<210> SEQ ID NO 73
<211> LENGTH: 46
<212> TYPE: DNA
<213> ORGANISM: Artificial Sequence
<220> FEATURE:
<223> OTHER INFORMATION: primer

<400> SEQUENCE: 73
cgtcgtggca gatcagccca tgatccgggt tctcccgatc gccctg 46

<210> SEQ ID NO 74
<211> LENGTH: 46
<212> TYPE: DNA
<213> ORGANISM: Artificial Sequence
<220> FEATURE:
<223> OTHER INFORMATION: primer

<400> SEQUENCE: 74
cgtcgtggca gatcagccct ttatccggca cctcccgatc gccctg 46

<210> SEQ ID NO 75
<211> LENGTH: 46
<212> TYPE: DNA
<213> ORGANISM: Artificial Sequence
<220> FEATURE:
<223> OTHER INFORMATION: primer

<400> SEQUENCE: 75
cgtcgtggca gatcagcccg cgatccggca cctcccgatc gccctg 46

<210> SEQ ID NO 76
<211> LENGTH: 46
<212> TYPE: DNA
<213> ORGANISM: Artificial Sequence
<220> FEATURE:
<223> OTHER INFORMATION: primer

<400> SEQUENCE: 76
cgtcgtggca gatcagccct ttatccggct gctcccgatc gccctg 46

<210> SEQ ID NO 77
<211> LENGTH: 46
<212> TYPE: DNA
<213> ORGANISM: Artificial Sequence
<220> FEATURE:
<223> OTHER INFORMATION: primer

<400> SEQUENCE: 77
cgtcgtggca gatcagcccg cgatccggct gctcccgatc gccctg 46

<210> SEQ ID NO 78
<211> LENGTH: 46
<212> TYPE: DNA
<213> ORGANISM: Artificial Sequence
<220> FEATURE:
<223> OTHER INFORMATION: primer

<400> SEQUENCE: 78
cgtcgtggca gatcagccct ttatccggat gctcccgatc gccctg 46

<210> SEQ ID NO 79
<211> LENGTH: 46
<212> TYPE: DNA
<213> ORGANISM: Artificial Sequence
<220> FEATURE:
<223> OTHER INFORMATION: primer

<400> SEQUENCE: 79
cgtcgtggca gatcagcccg cgatccggat gctcccgatc gccctg 46

<210> SEQ ID NO 80
<211> LENGTH: 46
<212> TYPE: DNA
<213> ORGANISM: Artificial Sequence
<220> FEATURE:
<223> OTHER INFORMATION: primer

<400> SEQUENCE: 80
cgtcgtggca gatcagccct tcatccggat gctcccgatc gccctg 46

<210> SEQ ID NO 81
<211> LENGTH: 14
<212> TYPE: PRT
<213> ORGANISM: Artificial Sequence
<220> FEATURE:
<223> OTHER INFORMATION: rPA-ILN

<400> SEQUENCE: 81

Gln Gly Asp Arg Glu His Pro Asp Gln Gly Leu Ile Cys His
1 5 10

<210> SEQ ID NO 82
<211> LENGTH: 14
<212> TYPE: PRT
<213> ORGANISM: artificial sequence
<220> FEATURE:
<223> OTHER INFORMATION: rPA-ILNmE12

<400> SEQUENCE: 82

Gln Gly Asp Arg Glu Gly Pro Cys Arg Gly Leu Ile Cys His
1 5 10

<210> SEQ ID NO 83
<211> LENGTH: 14
<212> TYPE: PRT
<213> ORGANISM: artificial sequence
<220> FEATURE:
<223> OTHER INFORMATION: rPA-ILNmF3

<400> SEQUENCE: 83

Gln Gly Asp Arg Glu Val Pro Cys Arg Gly Leu Ile Cys His
1 5 10

<210> SEQ ID NO 84
<211> LENGTH: 14
<212> TYPE: PRT
<213> ORGANISM: artificial sequence
<220> FEATURE:
<223> OTHER INFORMATION: rPA-ILNmB10

<400> SEQUENCE: 84

Gln Gly Asp Arg Glu Val Pro Cys Glu Gly Leu Ile Cys His
1 5 10

<210> SEQ ID NO 85
<211> LENGTH: 14
<212> TYPE: PRT
<213> ORGANISM: artificial sequence
<220> FEATURE:
<223> OTHER INFORMATION: rPA-ILNmG3

<400> SEQUENCE: 85

Gln Gly Asp Arg Glu Val Pro Asn Asn Gly Leu Ile Cys His
1 5 10

<210> SEQ ID NO 86
<211> LENGTH: 14
<212> TYPE: PRT
<213> ORGANISM: artificial sequence
<220> FEATURE:
<223> OTHER INFORMATION: rPAILNmB4

<400> SEQUENCE: 86

Gln Gly Asp Arg Glu Thr Pro Asn Arg Gly Leu Ile Cys His
1 5 10

<210> SEQ ID NO 87
<211> LENGTH: 14
<212> TYPE: PRT
<213> ORGANISM: artificial sequence
<220> FEATURE:
<223> OTHER INFORMATION: rPAILNmE6

<400> SEQUENCE: 87

Gln Gly Asp Arg Glu Asn Pro Asn Gly Gly Leu Ile Cys His
1 5 10

<210> SEQ ID NO 88
<211> LENGTH: 14
<212> TYPE: PRT
<213> ORGANISM: artificial sequence
<220> FEATURE:
<223> OTHER INFORMATION: rPA-ILNmC5

<400> SEQUENCE: 88

Gln Gly Asp Arg Glu Asn Pro Thr Ser Gly Leu Ile Cys His
1 5 10

<210> SEQ ID NO 89
<211> LENGTH: 14
<212> TYPE: PRT
<213> ORGANISM: artificial sequence
<220> FEATURE:
<223> OTHER INFORMATION: rPA-ILNmA8

<400> SEQUENCE: 89

Gln Gly Asp Arg Glu Leu Pro His Arg Gly Leu Ile Cys His
1 5 10

<210> SEQ ID NO 90
<211> LENGTH: 14
<212> TYPE: PRT
<213> ORGANISM: artificial sequence
<220> FEATURE:
<223> OTHER INFORMATION: rPA-ILNmF6

<400> SEQUENCE: 90

Gln Gly Asp Arg Glu Pro Pro Arg Leu Gly Leu Ile Cys His
1 5 10

<210> SEQ ID NO 91
<211> LENGTH: 254
<212> TYPE: DNA
<213> ORGANISM: artificial sequence
<220> FEATURE:
<223> OTHER INFORMATION: Coding Region of pQE30PA-IL (Figure 8 C)

<400> SEQUENCE: 91
gaattcatta aagaggagaa attaactatg agaggatcgc atcaccatca ccatcacgga 60
tccatggctt ggaaaagaaa tgggggccgc agggcgatcg ggagcatccg gaccaagggc 120
tgatctgcca cgatgcgttt tgtggtgcgc tggtcatgaa gattggcaac agcggaacca 180
ttccggtcaa taccgggttg ttccgttggg gctcgttcag tgtcaatatt ggaaaggatc 240
agtcctgaaa gctt 254

<210> SEQ ID NO 92
<211> LENGTH: 122
<212> TYPE: DNA
<213> ORGANISM: artificial sequence
<220> FEATURE:
<223> OTHER INFORMATION: Coding Region of pQE60PA-IL (Figure 8D)

<400> SEQUENCE: 92
gaattcatta aagaggagaa attaaccatg gcttggaaag gtgaggttct ggctaataac 60
gaagcagggc aggtaatcag tccagatctc atcaccatca ccatcactaa gcttaattag 120
ct 122

<210> SEQ ID NO 93
<211> LENGTH: 134
<212> TYPE: PRT
<213> ORGANISM: artificial sequence
<220> FEATURE:
<223> OTHER INFORMATION: rPA-ILN

<400> SEQUENCE: 93

Met Arg Gly Ser His His His His His His Gly Ser Met Ala Trp Lys
1 5 10 15

Gly Glu Val Leu Ala Asn Asn Glu Ala Gly Gln Val Thr Ser Ile Ile
20 25 30

Tyr Asn Pro Gly Asp Val Ile Thr Ile Val Ala Ala Gly Trp Ala Ser
35 40 45

Tyr Gly Pro Thr Gln Lys Trp Gly Pro Gln Gly Asp Arg Glu His Pro
50 55 60

Asp Gln Gly Leu Ile Cys His Asp Ala Phe Cys Gly Ala Leu Val Met
65 70 75 80

Lys Ile Gly Asn Ser Gly Thr Ile Pro Val Asn Thr Gly Leu Phe Arg
85 90 95

Trp Val Ala Pro Asn Asn Val Gln Gly Ala Ile Thr Leu Ile Tyr Asn
100 105 110

-continued

```
Asp Val Pro Gly Thr Tyr Gly Asn Asn Ser Gly Ser Phe Ser Val Asn
        115                 120                 125

Ile Gly Lys Asp Gln Ser
    130


<210> SEQ ID NO 94
<211> LENGTH: 130
<212> TYPE: PRT
<213> ORGANISM: artificial sequence
<220> FEATURE:
<223> OTHER INFORMATION: rPA-ILC

<400> SEQUENCE: 94

Met Ala Trp Lys Gly Glu Val Leu Ala Asn Asn Glu Ala Gly Gln Val
1               5                   10                  15

Thr Ser Ile Ile Tyr Asn Pro Gly Asp Val Ile Thr Ile Val Ala Ala
            20                  25                  30

Gly Trp Ala Ser Tyr Gly Pro Thr Gln Lys Trp Gly Pro Gln Gly Asp
        35                  40                  45

Arg Glu His Pro Asp Gln Gly Leu Ile Cys His Asp Ala Phe Cys Gly
    50                  55                  60

Ala Leu Val Met Lys Ile Gly Asn Ser Gly Thr Ile Pro Val Asn Thr
65                  70                  75                  80

Gly Leu Phe Arg Trp Val Ala Pro Asn Asn Val Gln Gly Ala Ile Thr
                85                  90                  95

Leu Ile Tyr Asn Asp Val Pro Gly Thr Tyr Gly Asn Asn Ser Gly Ser
            100                 105                 110

Phe Ser Val Asn Ile Gly Lys Asp Gln Ser Arg Ser His His His His
        115                 120                 125

His His
    130
```